United States Patent
Franchini et al.

(10) Patent No.: US 10,398,772 B2
(45) Date of Patent: Sep. 3, 2019

(54) RAS PATHWAYS AS MARKERS OF PROTECTION AGAINST HIV AND METHODS TO IMPROVE VACCINE EFFICACY

(71) Applicant: THE UNITED STATES OF AMERICA, as represented by the Secretary, Department of Health and Human Services, Bethesda, MD (US)

(72) Inventors: Genoveffa Franchini, Washington, DC (US); Rafick-Pierre Sekaly, Port Saint Lucie, FL (US); Slim Fourati, Cleveland, OH (US); Mark Cameron, Shaker Heights, OH (US); Monica Vaccari, Washington, DC (US); Luca Schifanella, Bethesda, MD (US); Shari Gordon, Research Triangle Park, NC (US); Melvin Doster, Beltsville, MD (US); Namal Malimbada Liyanage, Rockville, MD (US)

(73) Assignees: The United States of America, as represented by the Secretary, Department of Health and Human Services, Bethesda, MD (US); Oregon Health & Science University, Portland, OR (US)

( * ) Notice: Subject to any disclaimer, the term of this patent is extended or adjusted under 35 U.S.C. 154(b) by 0 days.

(21) Appl. No.: 15/110,400

(22) PCT Filed: Jan. 8, 2015

(86) PCT No.: PCT/US2015/010664
§ 371 (c)(1),
(2) Date: Jul. 7, 2016

(87) PCT Pub. No.: WO2015/106003
PCT Pub. Date: Jul. 16, 2015

(65) Prior Publication Data
US 2016/0331830 A1 Nov. 17, 2016

Related U.S. Application Data

(60) Provisional application No. 61/925,154, filed on Jan. 8, 2014.

(51) Int. Cl.
| | |
|---|---|
| *A61K 48/00* | (2006.01) |
| *C07K 14/47* | (2006.01) |
| *C12N 15/85* | (2006.01) |
| *A61K 9/127* | (2006.01) |
| *A61K 38/17* | (2006.01) |
| *A61K 39/21* | (2006.01) |
| *G01N 33/569* | (2006.01) |
| *A61K 39/12* | (2006.01) |

(Continued)

(52) U.S. Cl.
CPC .............. *A61K 39/21* (2013.01); *A61K 39/12* (2013.01); *A61K 45/06* (2013.01); *C12Q 1/702* (2013.01); *C12Q 1/703* (2013.01); *G01N 33/56988* (2013.01); *G01N 33/6887* (2013.01); *G01N 33/6893* (2013.01); *A61K 2039/53* (2013.01); *A61K 2039/55505* (2013.01); *A61K 2039/55516* (2013.01); *A61K 2039/55566* (2013.01); *A61K 2039/70* (2013.01); *C12N 2710/24042* (2013.01); *C12N 2740/15034* (2013.01); *C12N 2740/16134* (2013.01); *C12N 2740/16234* (2013.01); *C12Q 2600/106* (2013.01); *G01N 2333/91102* (2013.01); *G01N 2333/91205* (2013.01); *G01N 2800/52* (2013.01)

(58) Field of Classification Search
CPC .............. C07K 14/535; A61K 31/7115; A61K 48/0066; A61K 38/193; C12P 21/00
See application file for complete search history.

(56) References Cited

U.S. PATENT DOCUMENTS

| | | | |
|---|---|---|---|
| 6,969,609 B1 * | 11/2005 | Schlom ............ | C07K 14/70503 424/85.1 |
| 2005/0058658 A1 | 3/2005 | Rosenberg | |
| 2006/0264451 A1 | 11/2006 | Shim et al. | |

FOREIGN PATENT DOCUMENTS

| | | |
|---|---|---|
| EP | 2446898 | 5/2012 |
| WO | WO 1993/000109 | 1/1993 |

(Continued)

OTHER PUBLICATIONS

Belisle et al., "Long-term programming of antigen-specific immunity from gene expression signatures in the PBMC of rhesus macaques immunized with an SIV DNA vaccine," *PLoS One* 6:e19681, 2011.

(Continued)

*Primary Examiner* — Barry A Chestnut
(74) *Attorney, Agent, or Firm* — Klarquist Sparkman, LLP

(57) ABSTRACT

Compositions including a therapeutically effective amount of an HIV immunogen in combination with an agent that stimulates the Ras pathway, wherein the agent is not an aluminum salt, are disclosed. Methods are also disclosed for inducing an immune response to HIV, and/or to inhibit or treat HIV infection, in a subject, using an HIV immunogen and an agent that stimulates the Ras pathway. Methods also are disclosed for determining if an immunogenic composition will induce a protective response, and/or to determine if an immunogenic composition is of use to prevent or treat an HIV infection. The methods including determining if the immunogenic composition increases the level of one or more components of the Ras signaling pathway.

25 Claims, 52 Drawing Sheets

Figure 2A:
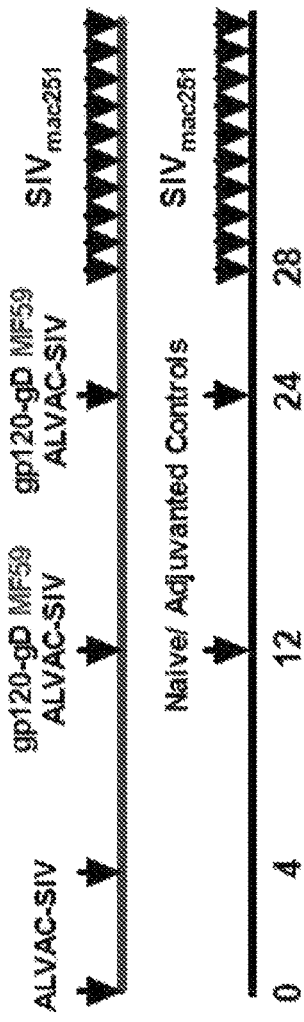

Specification includes a Sequence Listing.

(51) Int. Cl.
- A61K 45/06 (2006.01)
- C12Q 1/70 (2006.01)
- G01N 33/68 (2006.01)
- A61K 39/00 (2006.01)

(56) References Cited

FOREIGN PATENT DOCUMENTS

| WO | WO 2001/024822 | | 4/2001 |
|---|---|---|---|
| WO | WO 2002/006303 | | 1/2002 |
| WO | WO2009021971 | * | 2/2009 |
| WO | WO2009137632 | * | 11/2009 |
| WO | WO 2012/041981 | | 4/2012 |

OTHER PUBLICATIONS

Donia et al., "Potential use of rapamycin in HIV infection," *Br. J. Clin. Pharmacol.* 70: 784-793, 2010.

Finidori et al., "Regulators of growth hormone signalling," *Vitam. Horm.* 59: 71-97, 2000.

Fourati et al., "Modulation of RAS pathways as a biomarker of protection against HIV and as a means to improve vaccine efficacy," *AIDS Res Hum. Retroviruses* 30:A99, 2014.

Haynes et al., "Immune-correlates analysis of an HIV-1 vaccine efficacy trial," *N Engl J Med.* 366:1275-1286, 2012.

Herasimtschuk, et al. "Effects of recombinant human growth hormone on HIV-1-specific T-cell responses, thymic output and proviral DNA in patients on HAART: 48-week follow-up." *Journal of Immune Based Therapies and Vaccines* 6, No. 1, 2008.

Hiscott, et al. "Hostile takeovers: viral appropriation of the NF-kB pathway." *The Journal of Clinical Investigation* 107, No. 2: 143-151, 2001.

Kaslow et al., "Polymorphisms in HLA class I genes associated with both favorable prognosis of human immunodeficiency virus (HIV) type 1 infection and positive cytotoxic T-lymphocyte responses to ALVAC-HIV recombinant canarypox vaccines," *J Virol.* 75: 8681-8689, 2001.

Li and Panza, "Critical roles for Akt kinase in controlling HIV envelope-mediated depletion of CD4 T cells," *Retrovirology* 10: 60, 2013.

Mellado et al., "HIV-1 envelope protein gp120 triggers a Th2 response in mice that shifts to Th1 in the presence of human growth hormone," *Vaccine* 16: 111-5, 1998.

Muthumani et al., "HIV mediated PI3K/Akt activation in antigen presenting cells leads to PD-1 ligand upregulation and suppression of HIV specific CD8 T-cells," *J. Immunol.* 187: 2932-2943, 2011.

Nakaya and Pulendran, "Systems vaccinology: its promise and challenge for HIV vaccine development," *Curr Opin. HIV AIDS* 7: 24-31, 2012.

Nitayaphan et al., "A phase I/II trial of HIV SF2 gp120/MF59 vaccine in seronegative thais.AFRIMS-RIHES Vaccine Evaluation Group. Armed Forces Research Institute of Medical Sciences and the Research Institute for Health Sciences," *Vaccine* 18: 1448-1455, 2000.

Pal et al., "Systemic immunization with an ALVAC-HIV-1/protein boost vaccine strategy protects rhesus macaques from CD4+ T-cell loss and reduces both systemic and mucosal simian-human immunodeficiency virus SHIVKU2 RNA levels," *J Virol.* 80: 3732-3742, 2006.

Pal et al., "A baculovirus-expressed dicistrovirus that is infectious to aphids," *J Virol.* 81: 9339-9345, 2007.

Pegu et al., "Antibodies with high avidity to the gp120 envelope protein in protection from simian immunodeficiency virus SIV(mac251) acquisition in an immunization regimen that mimics the RV-144 Thai trial," *J Virol.* 87: 1708-1719, 2013.

Petersenn et al., "Transcriptional activation of the human growth hormone gene by ras oncogene," *Mol. Cell. Endocrinol.* 129: 47-54, 1997.

Rerks-Ngarm, et al., "Vaccination with ALVAC and AIDSVAX to prevent HIV-1 infection in Thailand," *N. Engl. J. Med.* 361: 2209-2220, 2009.

Vaccari et al., "Protection afforded by an HIV vaccine candidate in macaques depends on the dose of SIVmac251 at challenge exposure," *J Virol.* 87: 3538-3548, 2013.

Vahey et al., "$CD4^+$T-cell decline after the interruption of antiretroviral therapy in ACTG A5170 is predicted by differential expression of genes in the ras signaling pathway," *AIDS Res Hum. Retroviruses* 24: 1047-1066, 2008.

Van Rompay et al., "Attenuated poxvirus-based simian immunodeficiency virus (SIV) vaccines given in infancy partially protect infant and juvenile macaques against repeated oral challenge with virulent SIV," *J Acquir Immune Defic Syndr.* 38: 124-134, 2005.

Witte, et al. "Induction of HIV transcription by Nef involves Lck activation and protein kinase Cθ raft recruitment leading to activation of ERK1/2 but not NFκB." *The Journal of Immunology* 181, No. 12: 8425-8432, 2008.

PCT/US2015/010664 International Search Report dated Apr. 1, 2015 (5 pages).

PCT/US2015/010664 Written Opinion dated Apr. 1, 2015 (10 pages).

Bissa et al., "Modulation of DNA/ALVAC/gp120 vaccine immune-response by vaccination with Insulin-Like Growth Factor 1 (IGF-1)," *Journal of Immunology* 198(1 Supplement): 225.17 (May 1, 2017) (Abstract).

* cited by examiner

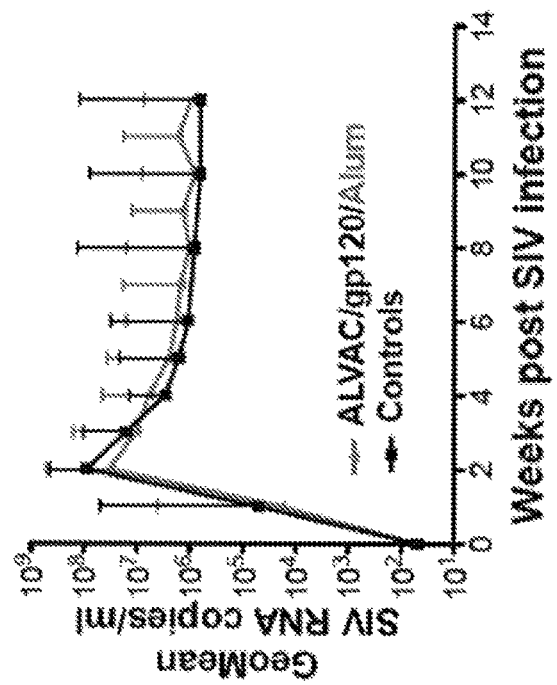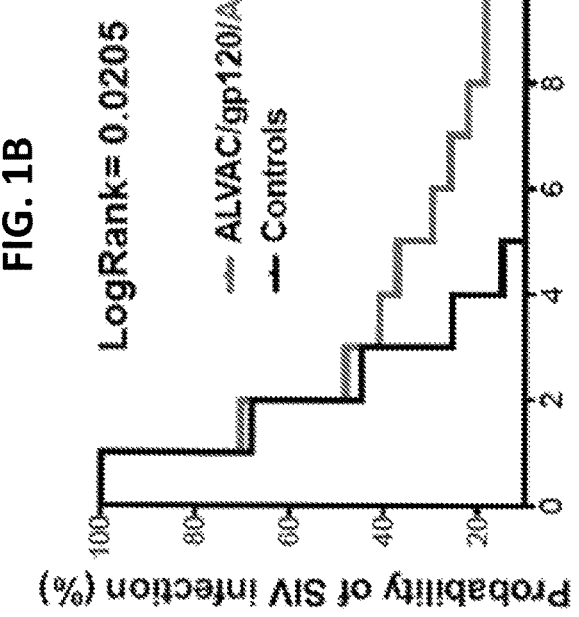
FIG. 1A
FIG. 1B
FIG. 1C

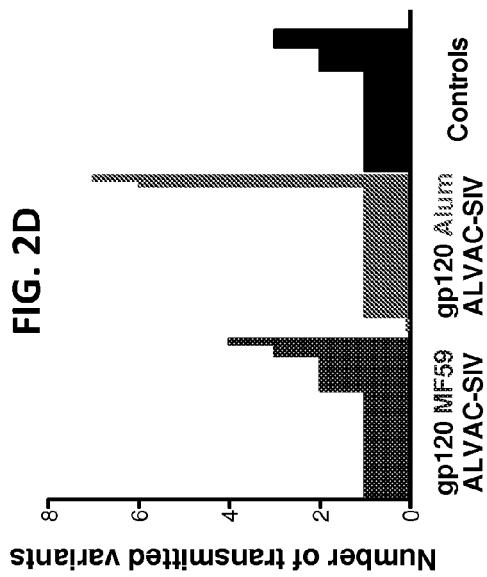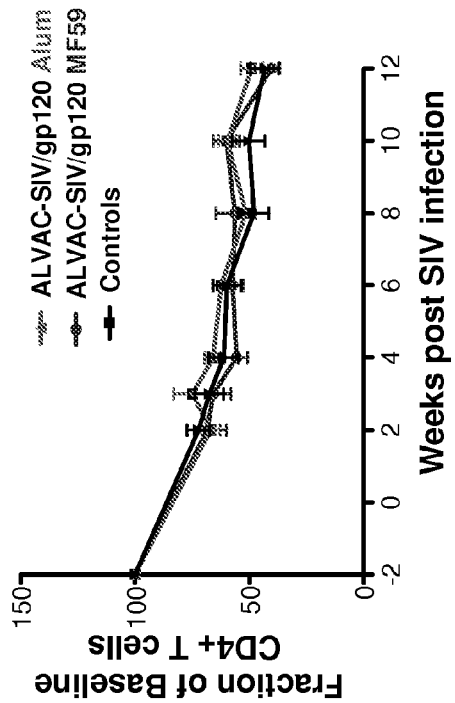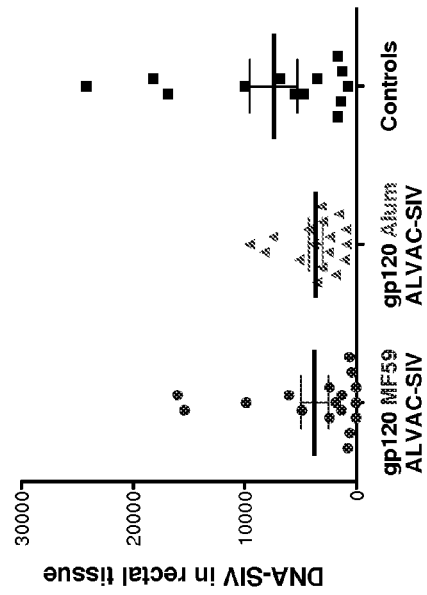

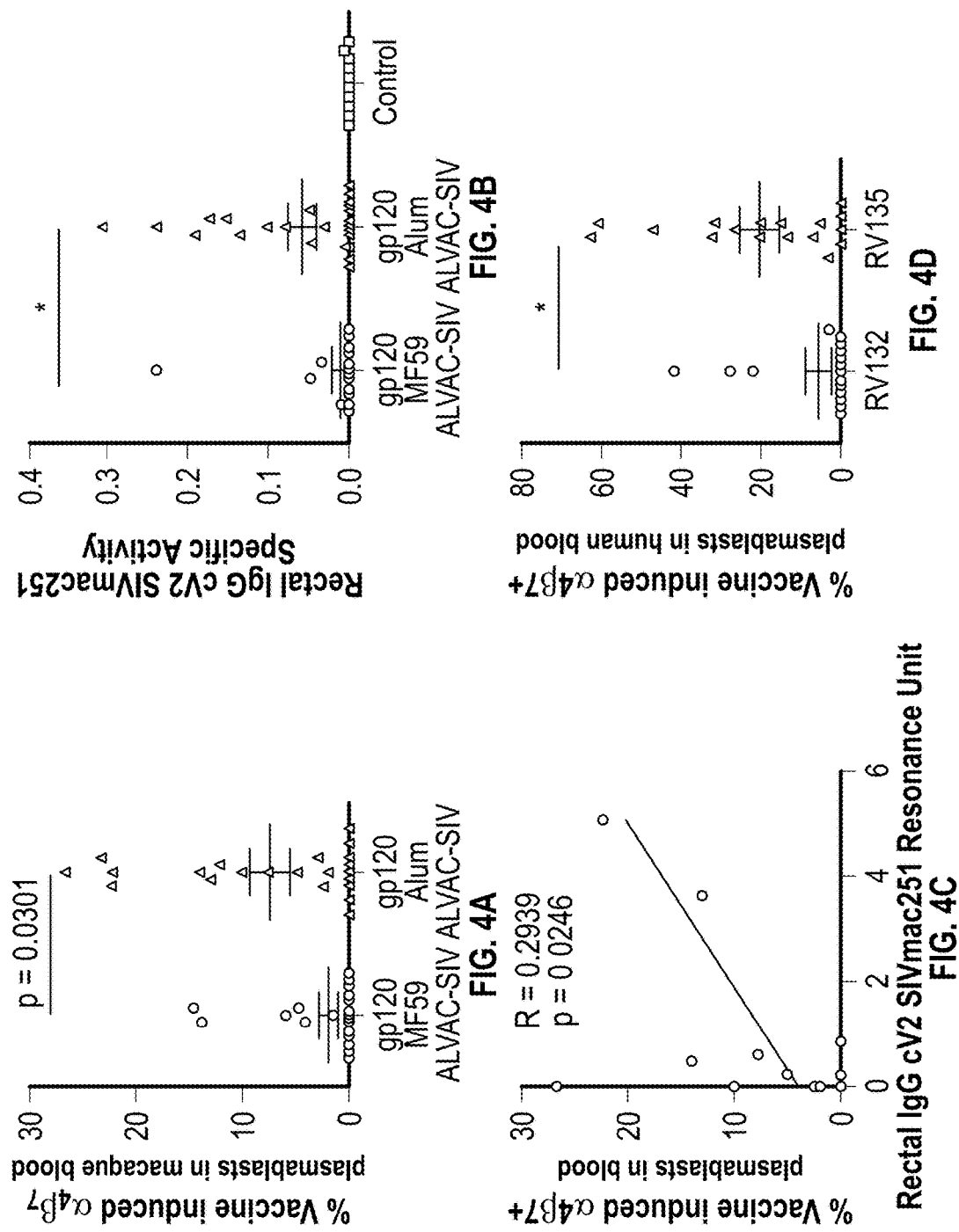

| cluster | #hubs | tag |
|---|---|---|
| 1 | CACN(A1,A2,B2,G6), PRKAR(1B,2B), CATSPER2 | Calcium signaling |
| 2 | MAP2K(1,2), SOS1, SHC1 | RAS regulation |
| 3 | WNT(11,4,16), FZD(1,10), TCF7L2, CTNNB1 | WNT signaling |
| 4 | ALDH(1A1, 3A2), ACAT1 | Aldehyde dehydrogenase |
| 5 | MAPK1,CATSPER(2,4), CACN (A1, A2, B1, D1, D2, G3, G6) | Calcium signaling |

V2 Peptides used in Serum

| | Peptide # | Serum: V2 Peptides |
|---|---|---|
| V2A | 23 | NETSSCIAQNNCTGLEQEQM |
| V2A | 24 | IAQNNCTGLEQEQMISCKFT |
| V2A | 25 | TGLEQEQMISCKFTMTGLKR |
| V2B | 26 | QMISCKFTMTGLKRDKTKEY |
| V2B | 27 | FTMTGLKRDKTKEYNETWYS |
| V2B | 28 | KRDKTKEYNETWYSTDLVCE |

SIV$_{mac251}$ V2 Sequence

FIG. 18E

V2 Peptides used in Rectal Secretions

| Peptide # | Rectal Secretions: V2 Peptides | |
|---|---|---|
| 50 | TSSCIAQDNCTGLEQ | V2A |
| 51 | CIAQDNCTGLEQEQM | V2A |
| 52 | QDNCTGLEQEQMISC | V2A |
| 56 | ISCKFNMTGLKRDKK | V2B |
| 57 | KFNMTGLKRDKKKEY | V2B |
| 58 | MTGLKRDKKKEYNET | V2B |
| 59 | LKRDKKKEYNETWYS | V2B |
|

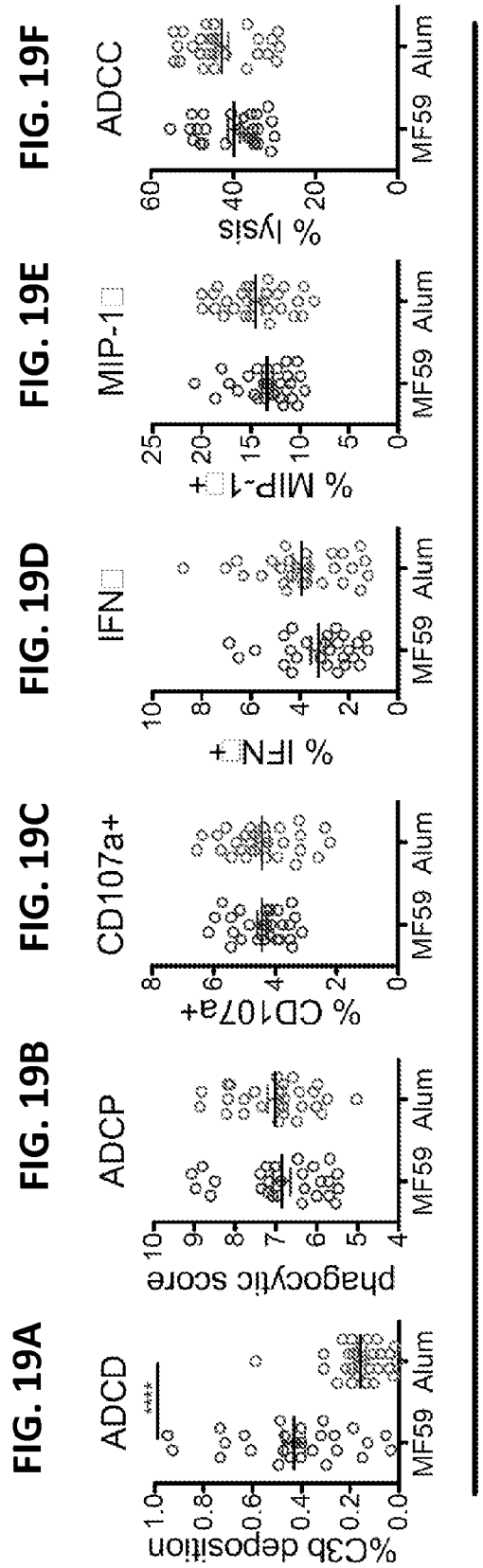

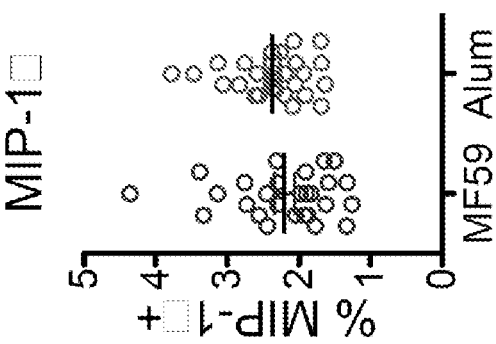
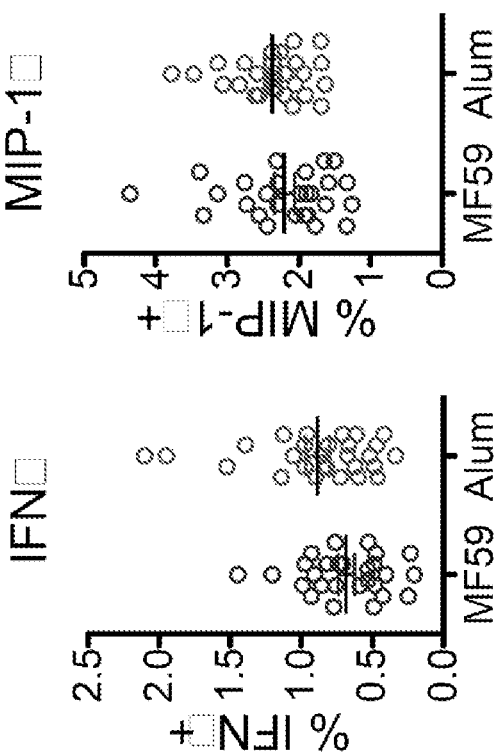
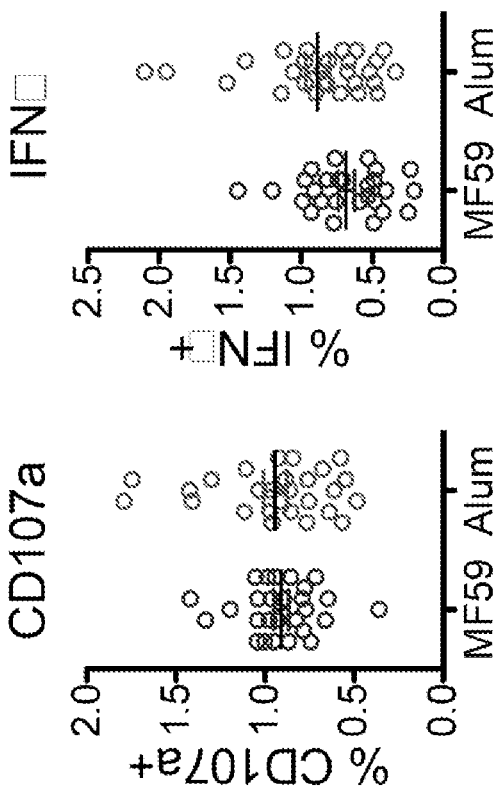
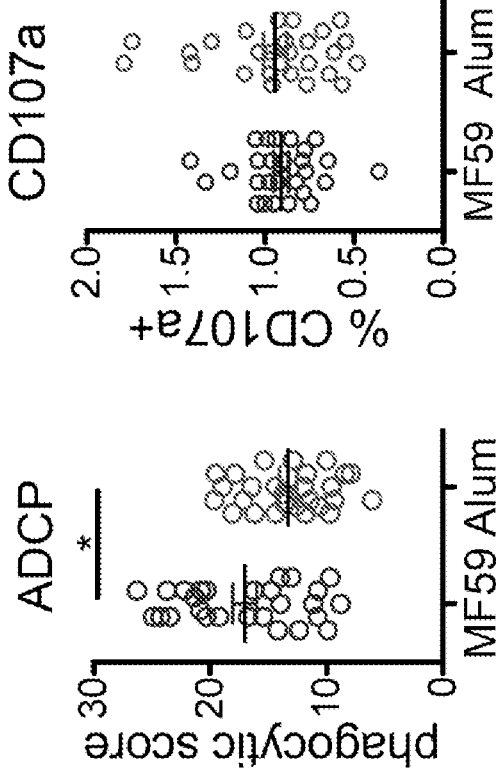

RAS PATHWAYS AS MARKERS OF PROTECTION AGAINST HIV AND METHODS TO IMPROVE VACCINE EFFICACY

CROSS REFERENCE TO RELATED APPLICATIONS

This is a § 371 U.S. national stage of International Application No. PCT/US2015/010664, filed Jan. 8, 2015, which was published in English under PCT Article 21(2), which in turn claims the benefit of U.S. Provisional Application No. 61/925,154, filed Jan. 8, 2014.

FIELD OF THE DISCLOSURE

This relates to the field of human immunodeficiency virus (HIV) infections, specifically to adjuvants of use for generating an immune response to HIV, and to a method for detecting that an immunogenic composition will be effective for generating an immune response to HIV in a subject.

BACKGROUND

Over 30 million people are infected with HIV worldwide, and 2.5 to 3 million new infections have been estimated to occur yearly. Although effective antiretroviral therapies are available, millions succumb to AIDS every year, especially in sub-Saharan Africa, underscoring the need to develop measures to prevent the spread of this disease.

An enveloped virus, HIV-1 hides from humoral recognition behind a wide array of protective mechanisms. The major envelope protein of HIV-1 is a glycoprotein of approximately 160 kD (gp160). During infection proteases of the host cell cleave gp160 into gp120 and gp41. gp41 is an integral membrane protein, while gp120 protrudes from the mature virus. Together gp120 and gp41 make up the HIV envelope spike, which is a target for neutralizing antibodies.

Adjuvants modulate the immune response and can improve the immunogenicity of vaccine candidates. The oil in water emulsion MF59 has been proposed to replace Alum in a Phase IIb trial in South Africa using ALVAC-HIV/gp120 vaccines. Unlike the Th2-inducing adjuvant Alum, MF59 induces both Th1 and Th2 responses, increases local inflammation, and can alter the generation of antibody isotypes, in an antigen dependent manner (Ott et al., *Vaccine* 13, 1557-1562 (1995); Carlson et al., *Am. J. Pathol.* 156, 2057-2065 (2000); Mosca et al. *Proc. Natl. Acad. Sci. U.S.A* 105, 10501-10506 (2008); Caproni, E. et al., *J. Immunol.* 188, 3088-3098 (2012); Valensi et al., *J. Immunol.* 153, 4029-4039 (1994)). The adjuvant MF59 increased the effectiveness of influenza vaccines, by enhancing antibody responses in the elderly (Podda, *Vaccine* 19, 2673-2680 (2001)) and in children (Vesikari et al., *Pediatr. Infect. Dis. J.* 28, 563-571 (2009)) when compared to other adjuvants. MF59, given with Hepatitis B virus vaccines, increased the generation and durability of protective antibodies in primates, mice, and immunosuppressed individuals (Traquina, et al., *J. Infect. Dis.* 174, 1168-1175 (1996); Singh, et al., *Vaccine* 24, 1680-1686 (2006)).

Immunogenicity studies conducted in humans suggest that the use of the MF59 instead of the Alum could benefit HIV vaccines. A Phase I clinical trial showed that the MF59 given together with a gp120/HIV-1SF2 HIV protein vaccine candidate was superior to Alum in inducing HIV-specific immune responses (McElrath, *Semin. Cancer Biol.* 6, 375-385 (1995)) Two Phase I/II trials demonstrated increased immune responses when an ALVAC-primed response was boosted with protein formulated in MF59 compared to Alum (Nitayaphan et al., *J. Infect. Dis.* 190, 702-706 (2004); Thongcharoen et al. *J. Acquir. Immune. Defic. Syndr.* 46, 48-55 (2007). However, a need remains for adjuvants that can be used to increase the immune response to HIV immunogens. In addition, a need remains for assays to determine if an immunogenic composition, such as a vaccine, will be effective for inducing an immune response to HIV in a subject.

SUMMARY OF THE DISCLOSURE

Ras is a central regulatory molecule that affects innate and adaptive immune responses, as well as cell motility and can be activated by several stimuli. It is disclosed herein that modulation of the Ras pathways can be a predictive biomarker of efficacy with this and other vaccine modalities. In addition, activation of Ras before, during vaccination, or after vaccination can be used as an adjuvant to increase vaccine protection.

In some embodiments, methods are disclosed for detecting the likelihood that an immunogenic composition will induce a protective immune response against a human immunodeficiency virus (HIV) in a subject. The methods include performing a biological assay that detects a level of MORC family CW-type zinc finger 3 (MORC3), staufen, RNA binding protein, homolog 1 (STAU1), 26S protease regulatory subunit S10B-like (Loc710822), interleukin enhancer binding factor 3, 90 kDa (ILF3), HECT and RLD domain containing E3 ubiquitin protein ligase 3 (HERC3), N(alpha)-acetyltransferase 38, NatC auxiliary subunit (NAA38), peroxisomal trans-2-enoyl-CoA reductase (PECR), mitogen-activated protein kinase kinase 1 (MAP2K), nucleoporin NDC1-like (LOC716474), Ewing sarcoma breakpoint region 1 (EWSR1), alpha-1,6-mannosyl-glycoprotein 2-beta-N-acetylglucosaminyltransferase-like (MGAT2) and nitric oxide synthase-interacting protein (NOSIP) in a biological sample from the subject administered the immunogenic composition; and comparing the level of MORC3, STAU1, Loc710822, ILF3, HERC3, NAA38, PECR, MAP2K, LOC716474, EWSR, MGAT2, and NOSIP to a respective control level of MORC3, STAU1, Loc710822, ILF3, HERC3, NAA38, PECR, MAP2K, LOC716474, EWSR, MGAT2 and NOSIP. The detection of an increase in the level of MORC3, STAU1, Loc710822, ILF3, HERC3, NAA38, PECR, MAP2K, LOC716474, EWSR and MGAT2, and a decrease in NOSIP, as compared to the respective control indicates the composition will induce a protective immune response against the HIV in the subject.

In further embodiments, methods are provided for determining if an immunogenic composition will induce a protective response. The methods including determining if the immunogenic composition increases the level of one or more components of the Ras signaling pathway. In some examples, the subject has an HIV infection.

In some embodiments, immunogenic composition is disclosed that includes an effective amount of human immunodeficiency virus (HIV) immunogen, or a nucleic acid encoding the immunogen, and an effective amount of an agent that stimulates the Ras pathway, wherein the agent is not aluminum or an aluminum salt. The use of these compositions is also disclosed.

In additional embodiments, methods are provided for inducing an immune response to a human immunodeficiency virus (HIV) in a subject. The methods include administering an effective amount of an HIV immunogen, or nucleic acid encoding the immunogen, and an effective amount of an agent that that stimulates the Ras pathway, wherein the agent is not aluminum or an aluminum salt, thereby inducing the immune response.

The foregoing and other features and advantages of the invention will become more apparent from the following detailed description of a several embodiments which proceeds with reference to the accompanying figures.

BRIEF DESCRIPTION OF THE FIGURES

FIGS. 1A-1C. (1A) Study design representing 27 animals vaccinated with ALVAC-SIV/gp 120/Alum strategy in grey and 47 historical and concurrent controls animals in black. (1B) SIV acquisition in animals vaccinated with Alum-regimen and concurrent controls (12 MF59-adjuvanted; 6 Alum-adjuvanted; 6 naïve). (1C) SIV-RNA levels in the plasma of ALVAC/gp120/Alum-vaccinated and control animals (GeoMean±standard error).

FIGS. 2A-2F. (2A) Study design representing 27 animals vaccinated with ALVAC-SIV/gp120/MF59 strategy and control animals. (2B) SIV acquisition in animals vaccinated with MF59-regimen and Controls (MF59-adjuvanted; Alum adjuvanted; naïve). (2C) SIV-RNA levels in the plasma of ALVAC/gp120/MF59-vaccinated and control animals (GeoMean±standard error). (2D) Number of transmitted founder variants. (2E) SIV-DNA levels in rectal mucosa tissue collected at 3 weeks from the infection. (2F) Changes in the absolute number of circulating CD4 T cells expressed as fraction of CD4 T cells over the pre-infection number.

FIGS. 3A-3D Envelope binding rectal (3A-3B) IgG to cV2 of $SIV_{mac251}$ and $SIV_{sme543.3}$. $SIV_{mac251}$ acquisition in vaccinated animals with rectal IgG titers to cV2 of $SIV_{smE543}$>0 (solid lines) or =0 (dotted lines) in MF59 (3C) and alum group (3D).

FIGS. 4A-4I. (4A) Frequency of vaccine-induced $\alpha 4\beta 7^+$ plasmablasts (baseline-post-immunization) measured in blood of all vaccinated macaques at week 25. (4B) Specific activity of IgG against cyclic V2 of $SIV_{mac251}$ in rectal swabs of vaccinated animals collected at week 27. (4C) Direct correlation between rectal mucosa cyclic V2 (resonance unit, week 27) and the frequency of vaccine induced $\alpha 4\beta 7^+$ plasmablasts in the blood (week 25). (4D) Frequency of $\alpha 4\beta 7^+$ plasmablasts in the blood of 18 vaccines from the RV132 and 18 from RV135 trial at 2 weeks from the last immunization (week26). The immunization schedule is identical to the one used in the study. (4E) Inverse correlation between folds change in the frequency of $\alpha 4\beta 7^+$ and $CXCR3^+$ plasmablasts after vaccination with the Alum strategy, in macaques. (4F) Envelope binding rectal IgG to cV2 $SIV_{sme543.3}$ in animals with vaccine-induced increase or decrease in the frequency of $\alpha 4\beta 7^+$ plasmablasts. (4G) Frequency of vaccine-induced CXCR3+ plasmablasts (baseline-post-immunization) measured in blood of all vaccinated macaques at week 25. (4H) Specific activity of IgG against cyclic V2 of $SIV_{mac251}$ in rectal swabs of vaccinated animals collected at week 27. (4I) Direct correlation between rectal mucosa cyclic V2 (resonance unit, week 27) and the frequency of vaccine induced CXCR3+ plasmablasts in the blood (week 25). Frequency of CXCR3+ plasmablasts in the blood of 18 vaccines from the RV132 and 18 from RV135 trial at 2 weeks from the last immunization (week26). The immunization schedule is identical to the one used in the study.

FIG. 5. Histogram presenting the number of transcripts correlated to protection for statistical stringency of 5% on the nominal p-value (nomPval) or false discovery rate (FDR).

FIG. 6. Heatmap presenting the evaluation of predictors of protection on each combination vaccine×immunization step. The Pearson correlation between the predicted protection and the observed protection (i.e. the number of SIV challenge to infection) is presented using a greyscale.

FIG. 7. Heatmap showing the expression of the top 50 predictors of protection by ALVAC+Alum identified on the pre-vax samples on all ALVAC+Alum samples (pre, post 1st, post 3rd). Samples were ordered by their overall expression of the genes positively correlated of protection (mean-rank ordering). Pearson t-test was used to assess the association between the sample ordering and the number of SIV challenge to protection. The correlation was r=0.624 (p=1.04e-08) when including all ALVAC+Alum samples (pre-vax and post-vax). After excluding pre-vax samples (used to identify those 50 transcripts) the correlation was r=0.351 (p=0.0167).

FIGS. 8A-8B. Heatmaps showing the modules of pathways associated with protection by the Alum-strategy (8A) pre-vax and (8B) post-vax. Ratio of correlates of protection in common between two pathways is presented using a greyscale gradient. Only RAS related pathways were common between pre-vax and post-vax list of pathways associated to protection.

FIG. 9 is a schematic diagram of the EGF signaling pathway.

FIGS. 10-11 are schematic diagrams of the Ras pathway, and provide information on biological molecules that could be activated and/or used as adjuvants.

FIG. 12 is a schematic diagram of the AKT pathway.

FIGS. 13A-13C. (13A) The ability of individual sets of aggregate data to predict protection was compared among animals that were infected in 4 or fewer challenges (≤4) or after 5 or more challenges (≥5) using logistic regression and LOO cross-validation. (13B) Feature contribution associated with decreasing or increasing (arrows) levels of protection. (13C) Correlation plots (Pearson) in which greyscale represents positive and greyscale with an "x" indicates a negative correlation with the number of challenges required to achieve infection, while the size of the dot represents the strength of the association, depict the relationship of mucosal multiplex detection of total rhesus IgG (rhIgG) or Fc binding proteins (huC1q, rhFcgR2A-1, rhFcgR3A-1) specific for various SIV envelope-derived antigens with risk of SIV acquisition.

FIGS. 14A-14G. (14A) Scatter plot representing the samples plotted in two dimensions using the first and second principal components. Principal component analysis (PCA) was used to reduce the multidimensionality of the microarray data set to two dimensions represented here as principal component (PC1 and PC2). The distance between points is proportional to the similarity between the transcriptomic profiles of samples. (14B) Heatmap presenting the evaluation of predictors of protection on each combination vaccine×immunization step. The Pearson correlation between the predicted protection and the observed protection (i.e. the number of SIV challenge to infection) is proportional to the size of the dots. The p-values of a Pearson t-test are presented using a greyscale. (14C) (left panel) Heatmap showing the expression of 12-gene signature predicting protection by the alum group. The 12 genes composing this signature were identified on the pre-vax samples and tested on the post-vax samples (post-$1^{st}$ and post-3rd) (right panel).

(14D) Receiver operation characteristic (ROC) curve presenting the accuracies of the 12-gene classifier on the post-vax samples. (14E) Network inference based on the 12-genes included in the predictive signature. List of 12-genes was uploaded in GENEMANIA®. Edges are based on co-localization, co-expression. (14F) Integrative analysis between the 12 gene predictive of protection by ALVAC+Alum and the humoral markers of associated with the number of challenges to infection. Least-square regression using as independent variables the pre-vaccination expression of the 12-gene identified as predictive of protection by ALVAC+Alum and as dependent variables the humoral makers of protection was performed using the function spls of the R package MIXOMICS®. The network present all the pairs of features significantly correlated to each other (absolute Pearson correlation: |r|>0.25, p<0.05). We observe concordant information between the gene-expression analysis and the humoral analysis. (14G) Gene signature.

FIGS. 15A-15E. (15A) Twenty-three historical (dotted line) and twenty-four concurrent controls (solid line) (6 naïve, 6 alum-adjuvant, 12 MF59 adjuvant) show no differences in the acquisition rate of infections. (15B) In mice, MF59 induces local inflammation and up-regulates IFN-stimulated genes, resulting in the recruitment of neutrophils (Mosca et al., *Proc. Natl. Acad. Sci. U.S.A* 105, 10501 (Jul. 29, 2008); Nitayaphan et al., J. Infect. Dis. 190, 702 (Aug. 15, 2004)). Immunohistochemistry on inguinal lymph nodes on one animal vaccinated with the MF59 (left panel) or alum (right panel) regimen, 2 weeks after the last immunization (week 26), shows persistence of neutrophils in the MF59, but not in the alum. Pictures are at 40× resolution and Elastase$^+$ cells (neutrophils) are in brown. (15C) Neutrophils score in four animals vaccinated with MF59 (circle) and five animals vaccinated with the alum-regimen (triangle). Each dot represents the average of 5 counts/picture/animal and the lines represent the median. The p-value was calculated using the repeated measures analysis of variance. (15D) Because persistence of neutrophils in lymph nodes could increase immune activation and provide more target cells for SIV$_{mac251}$ infection, we measured the absolute number of Ki67$^+$ CD4$^+$ T-cells in the rectal mucosa of vaccinated and control macaques at 1 week (week 25) after the last immunization, 3 weeks before challenge exposure. We observed no significant differences. Each dot represents one animal, and lines represent the medians. (15E) No significant correlation was found in either group in the number of CD4$^+$ Ki67$^+$/mm$^2$ in rectal mucosa and the time of SIV$_{mac251}$ acquisition.

FIGS. 16A-16M. Serum and mucosal secretions were collected at 2 weeks after the last immunization. IgG titers in serum against the gp130 of SIV$_{mac251}$ (16A) and the gp140 SIV$_{smE660}$ (16B). Specific activity of rectal IgG binding antibodies to the gp130 of SIV$_{mac251}$ (16C) and the gp140 SIV$_{smE660}$ (16D). IgG titers to the gp70-V1/V2 scaffold of SIV$_{mac251}$ (16E) or SIV$_{smE660}$ (16F) in serum. Specific activity of IgG binding antibodies to the gp70-V1/V2 scaffold of SIV$_{mac251}$ (16G) or SIV$_{smE660}$ (16H) in rectal secretion. IgA titers in serum against the gp130 of SIV$_{mac251}$ (16I) and the gp140 SIV$_{smE660}$ (16J). Neutralizing antibodies to Tier1 SIV$_{mac251.6}$. (16K), phagocytosis index (16L) and ADCC (16M). Each triangle, circle or square represents one animal and the lines represent the medians.

Figure 17A:
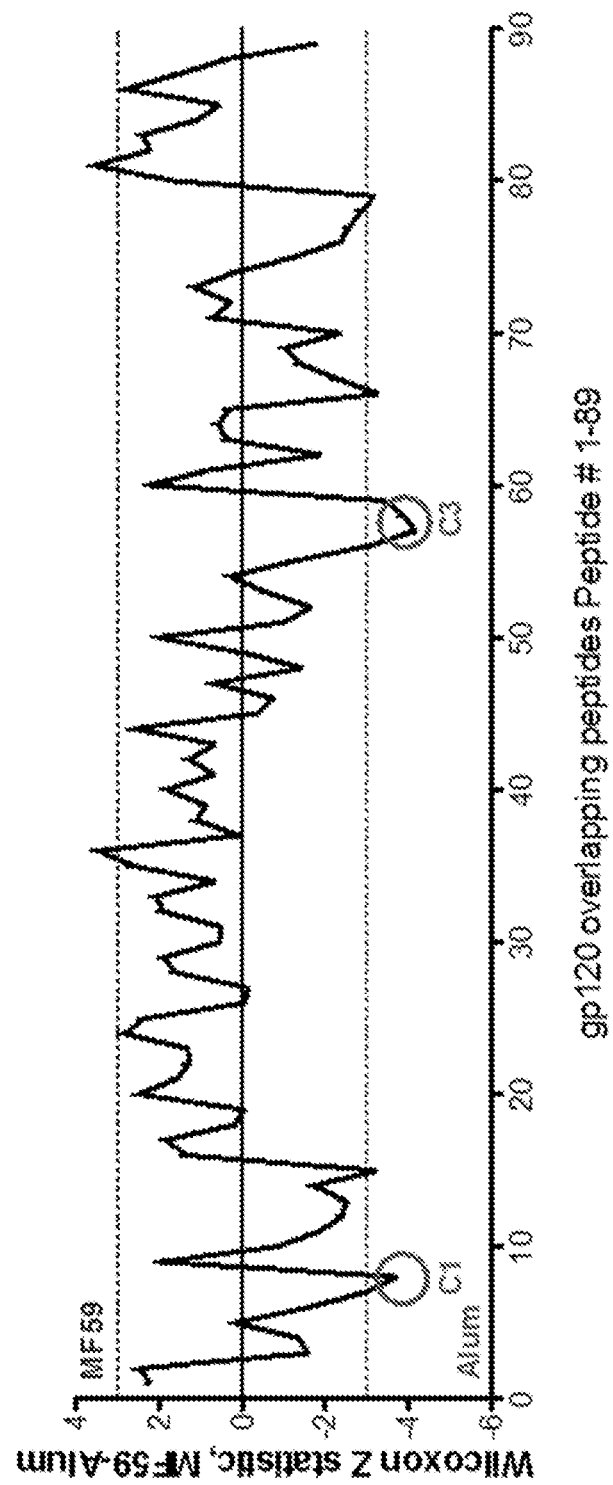
Figure 17B:
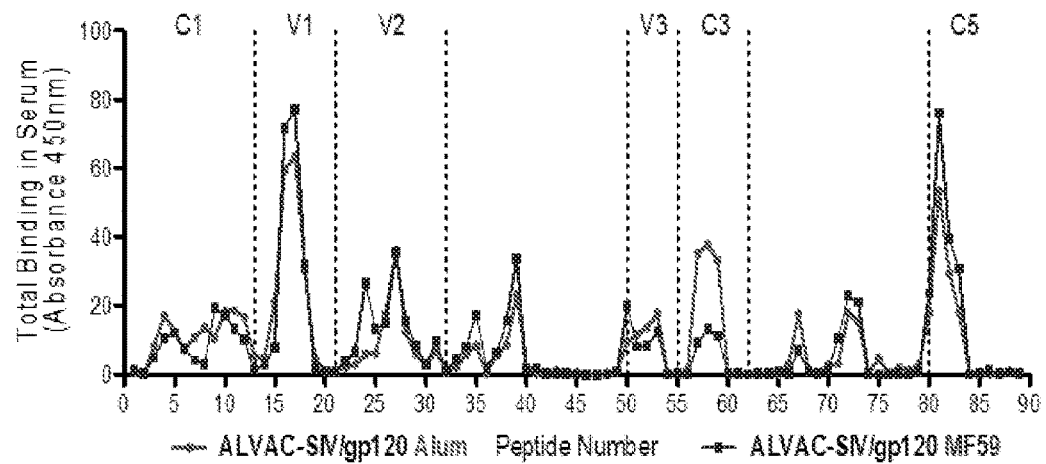
Figure 17C:
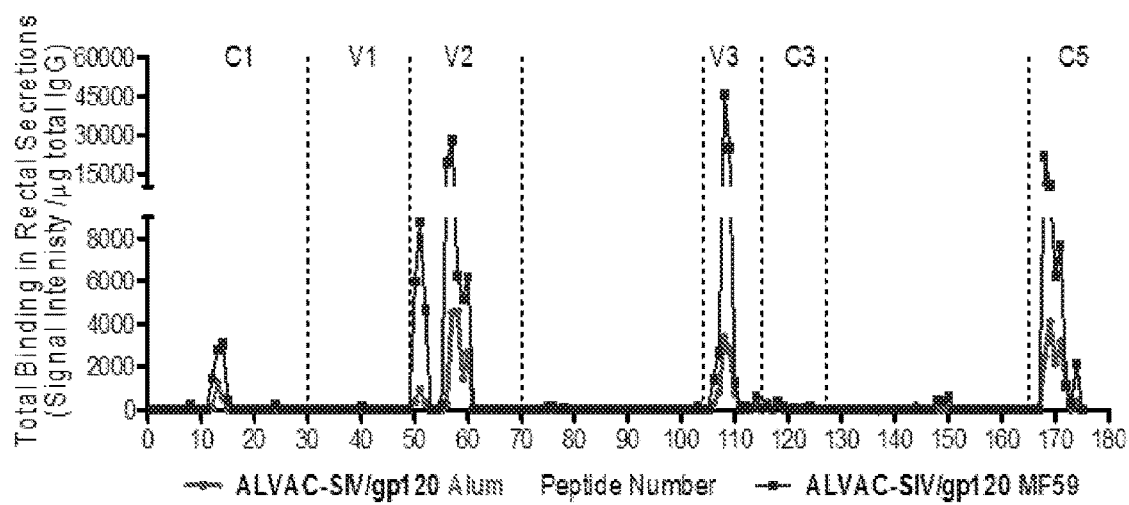
Figures 18A, 18B:
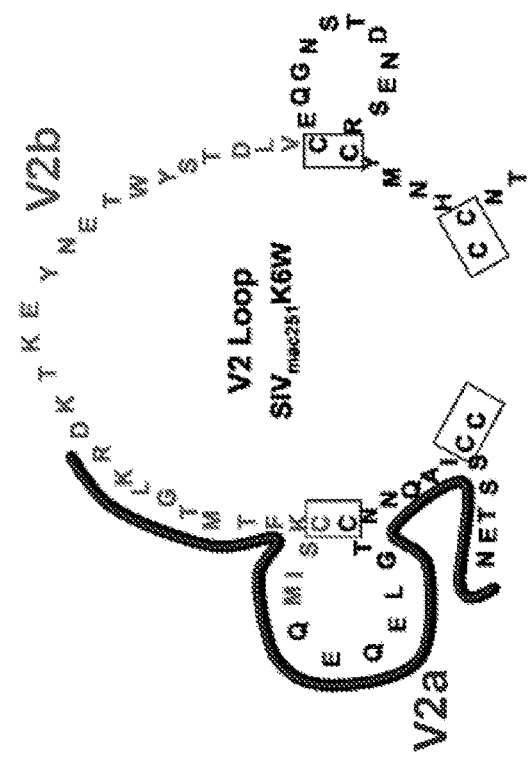
Figure 18C:
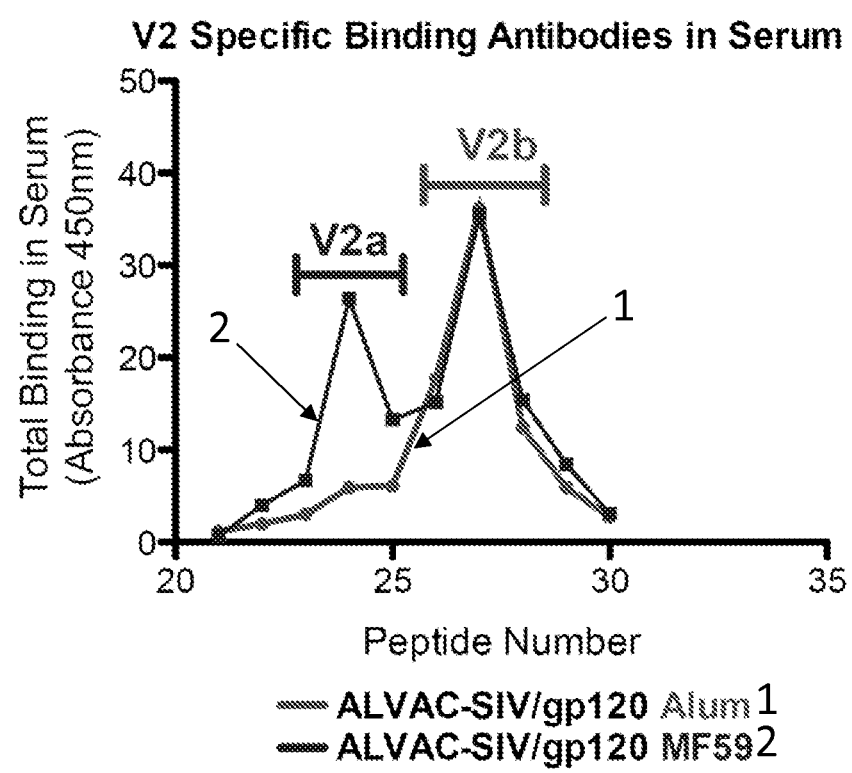
Figure 18F:
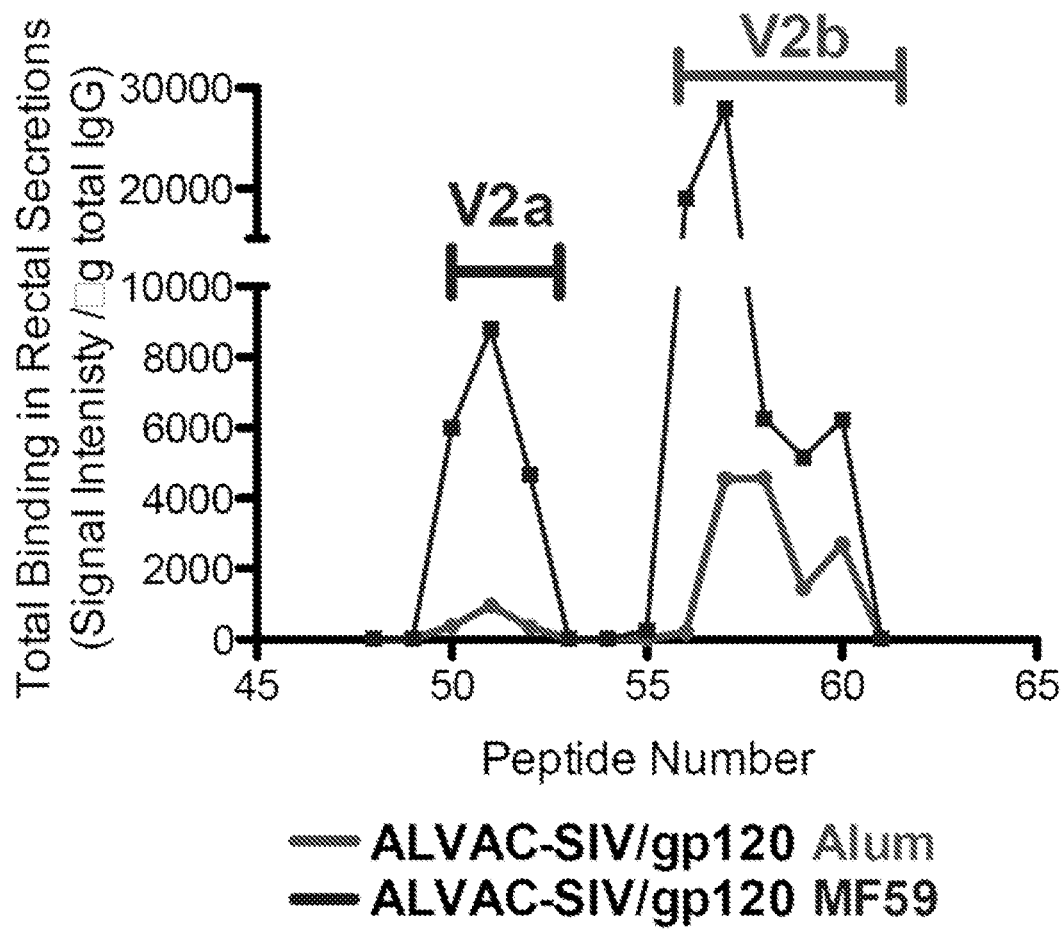

FIGS. 17A-17C. (17A) Comparative recognition of overlapping peptides presented as the Z statistic of the Mann-Whitney-Wilcoxon test with dashed lines marking significance at the p<0.05 level after a stringent correction for multiple comparisons by the Hochberg method. (17B) Total Binding antibodies in serum measured by ELISA using linear overlapping peptides that span SIV$_{mac251K6W}$ gp120. Peptide mapping in serum was performed using peptides of 20 amino acid lengths that overlapped by 14 and is presented as absorbance at 450 nm. The ALVAC-SIV/gp120 alum group is shown in light gray and the ALVAC-SIV/gp120 MF59 group in dark grey. (17C) Total binding antibodies in rectal secretions measured by PepStar with overlapping linear peptides that span SIV$_{mac239}$ gp120. Peptides used are 15 amino acid lengths that overlapped by 12. Normalized values are presented as signal intensity per µg of total IgG.

FIGS. 18A-18F. (18A) Amino acid sequence of V2 loop from SIV$_{mac251K6W}$ (Franchini et al., *Nature* 328, 539 (1987, 1987)) (SEQ ID NO: 18), predicted structure based on reference (Johnson et al., *J. Virol.* 76, 2075 (March, 2002), with the N terminal portion V2a and mid-region V2b. (18B) Amino acids sequence of the peptides within V2a and V2b (SEQ ID NOs: 20-25) from SIV$_{mac251K6W}$ were used to measure antibody responses in serum by ELISA as depicted in (18C) for all the ALVAC-SIV/gp120 Alum vaccinated animals (1) and all ALVAC-SIV/gp120 MF59 vaccinated animals (2). Distinct and overlapping V2 responses were observed in the two groups. (18D) Sequence of V2 loop from SIV$_{mac239}$, predicted structure (Johnson et al., *J. Virol.* 76, 2075 (March, 2002)) (SEQ ID NO: 26), with the V2a and V2b highlighted. (18E) Amino acid sequence of V2a region and V2b from SIV$_{mac239}$ (SEQ ID NO: 27-34) that were used to measure antibody responses in rectal secretions by PepStar in ALVAC-SIV/gp120 Alum vaccinated animals (circle) and ALVAC-SIV/gp120 MF59 vaccinated animals (square) (18F). Distinct and overlapping V2 responses were again observed in the two groups. The first maps to the V2a region highlighted by the bar and the second to the V2b highlighted by the bar. Animals vaccinated with ALVAC-SIV/gp120 Alum have one dominant V2 peak within V2b.

FIGS. 19A-19J. Gp120-specific complement activation (19A), phagocytosis (19B), NK cell degranulation (19C), IFNγ-secretion (19D), MIP1β (19E), ADCC mediated cytolysis (19F). V2-specific phagocytosis (19G), NK degranulation (19H), IFNγ-secretion (19I), and MIP1β (19J) are plotted as univariate analyses. Each dot represents one animal and the lines represent the medians.

Figure 20:
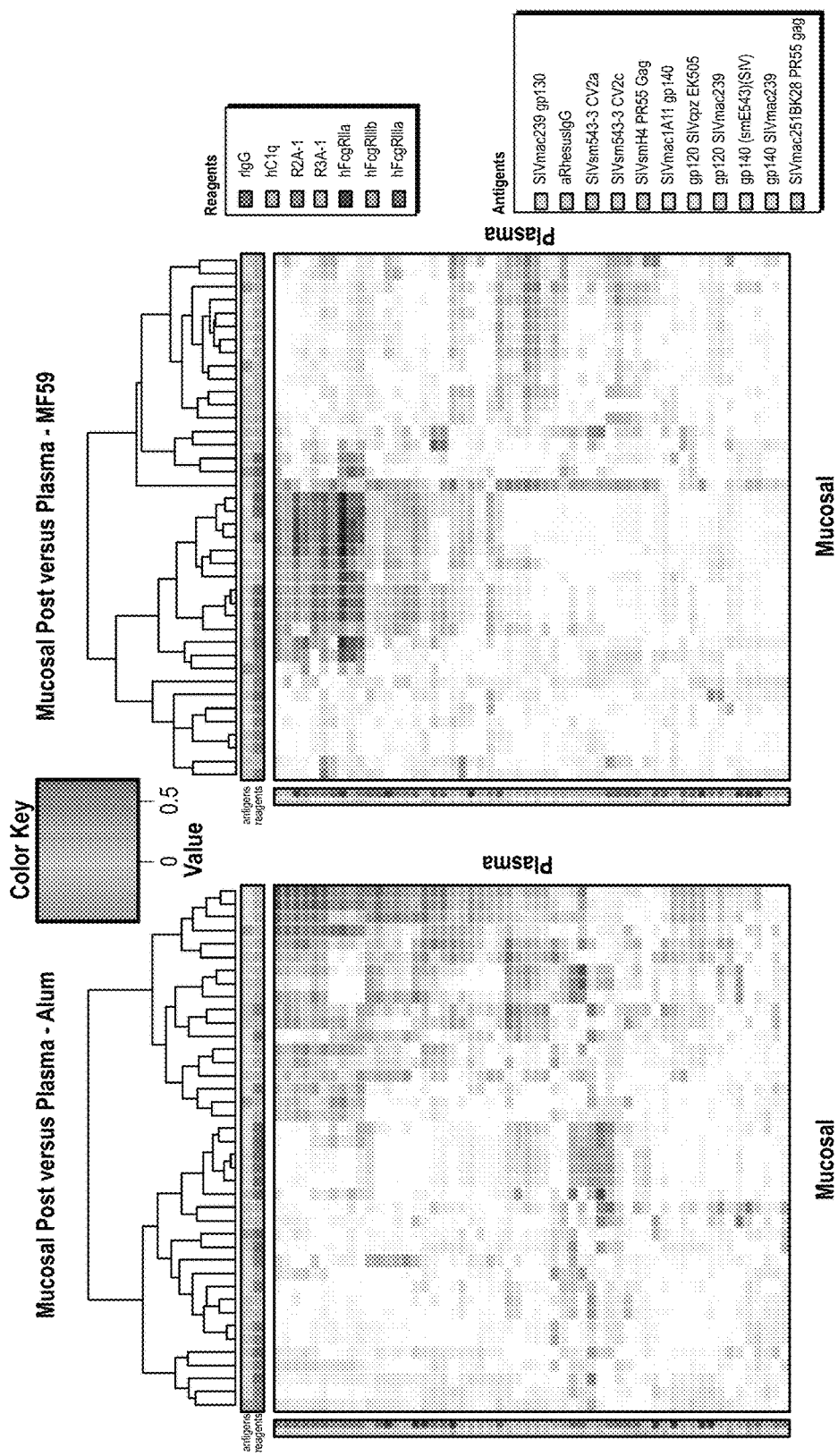

FIG. 20. Representative multiplex data. Heatmap of centered and scaled multiplex data from plasma samples. Each antibody feature, representing the combination of antigen-specificity (antigen) and mode of IgG detection (reagent) was centered and scaled. Animals and antibody features were clustered by Ward Linkage FIG. 21. Divergence between systemic and mucosal IgG responses. Correlation plot of plasma and mucosal IgG responses as assessed in the multiplexed assay. Pearson correlation coefficients were determined for each antibody specificity (antigen) and Fc detection characteristic (reagent) pair across animals within each vaccine group. Negative and positive correlations are shown using the color key (greyscale). Features are clustered by Ward Linkage.

Figure 22:
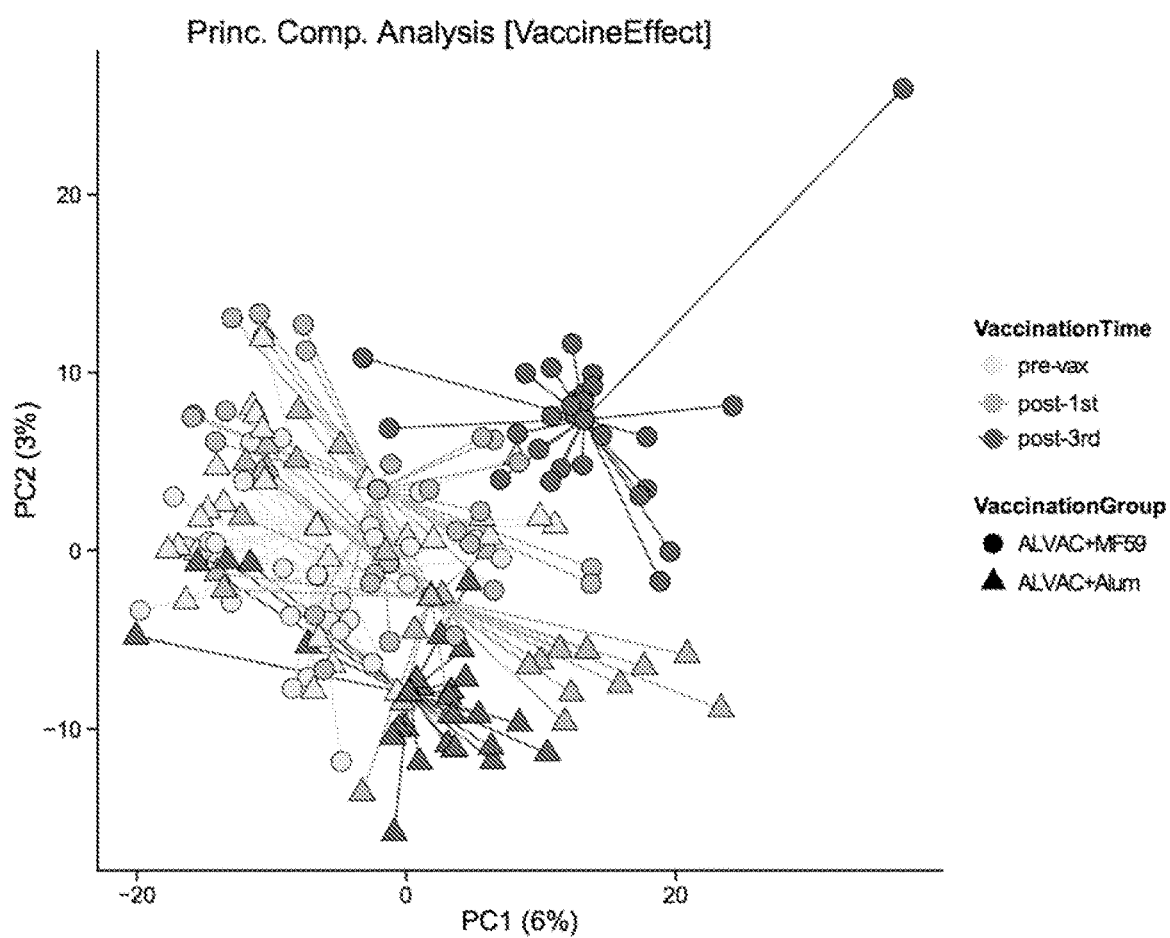

FIG. 22. Genes differently expressed between vaccines (MF59 group in circles and alum group in triangles) were identified for each time point (VaccinationTime) separately (F-test: p≤0.05). Expression of those 2081 genes was summarized in a principal component analysis. The first (PC1) and second (PC2) principal components explaining the most transcriptomic variance were graphed in a 2D scatter plot. Centroids of every vaccine and time point are also represented. Colored lines indicate the distance between the each sample and its corresponding centroid. Black arrows indicate distances between the MF59 and alum-group for the three time points. As expected, the difference between vaccines is more pronounce post-3rd immunization (1st gp120+adjuvant boost) than post-1st immunization (AL-VAC-SIV only immunization).

Figure 23:
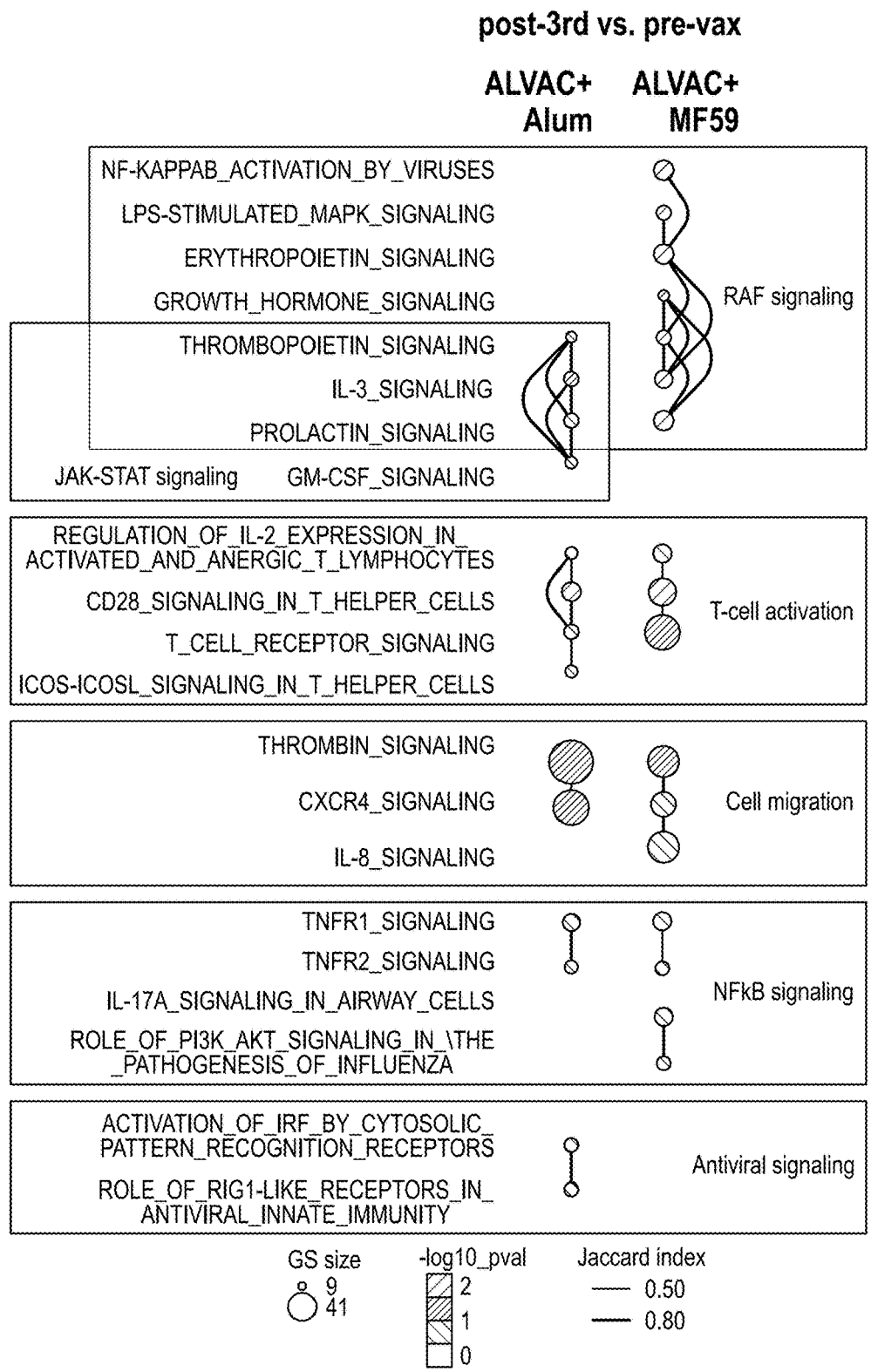

FIG. 23. Enrichment maps showing the different pathways enriched between immunization by the MF59 vaccine or the Alum vaccine. Gene Set Enrichment analysis (GSEA) was used to annotate genes and rank canonical pathways (Subramanian et al., *Proceedings of the National Academy of Sciences of the United States of America* 102, 15545 (Oct. 25, 2005)). In brief, genes were ranked by the absolute differential expression between pre-vax and post-3$^{rd}$ (i.e. absolute moderated t-statistic), separately for the MF59 and Alum group. Given a defined set of genes (here Ingenuity canonical pathways), the goal was to determine whether the members of that GeneSet (GS) are found at the top of the list, implying they are not randomly distributed across the ranked list. An Enrichment Score was calculated to quantify the degree to which the GS is over-represented at the top of the entire ranked list. A gene-based permutation test procedure was used to estimate a false discovery rate for a given enrichment score (−log 10_pval). Significantly enriched pathways were organized in networks using the enrichment maps strategy (Merico, et al., *PloS one* 5, e13984 (2010)). This was accomplished by linking GS by the number of genes differently expressed overlapping between GS. Overlap between significant GS is computed according to the Jaccard index. A Jaccard index of 0.5 was used to generate the enrichment maps. This technique allows the identification of the major enriched functional themes and interprets the enrichment results of GSEA. The functional themes are given different colors.

Figure 24:
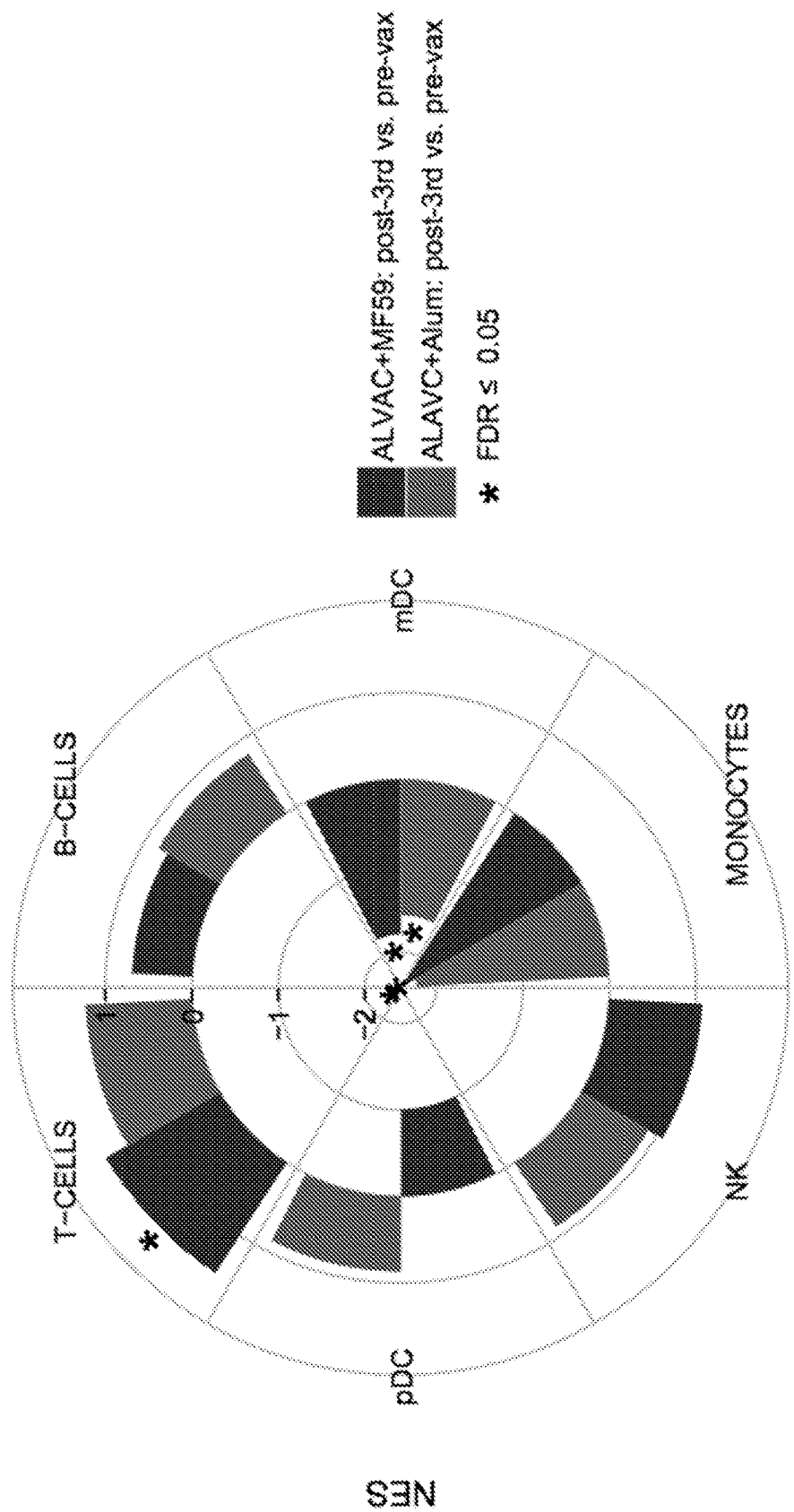

FIG. 24. Blood cell-type deconvolution was performed using type-specific modules (Nakaya et al., (20110720 DCOM-20111007, 2011).). GSEA was used to assess the over-representation of the blood cell type-specific GS at the top or bottom of the list of genes ranked by their level of differential expression. The normalized enrichment score (NES) return by GSEA is plotted as function of the blood cell-type-specific gene set for both, ALVAC-SIV/gp120 MF59 (dark grey) and ALVAC-SIV/gp120 alum (light grey). A positive NES indicates enrichment among genes up-regulated by the vaccine while a negative NES indicates enrichment among genes down-regulated by the vaccine.

Figure 25:
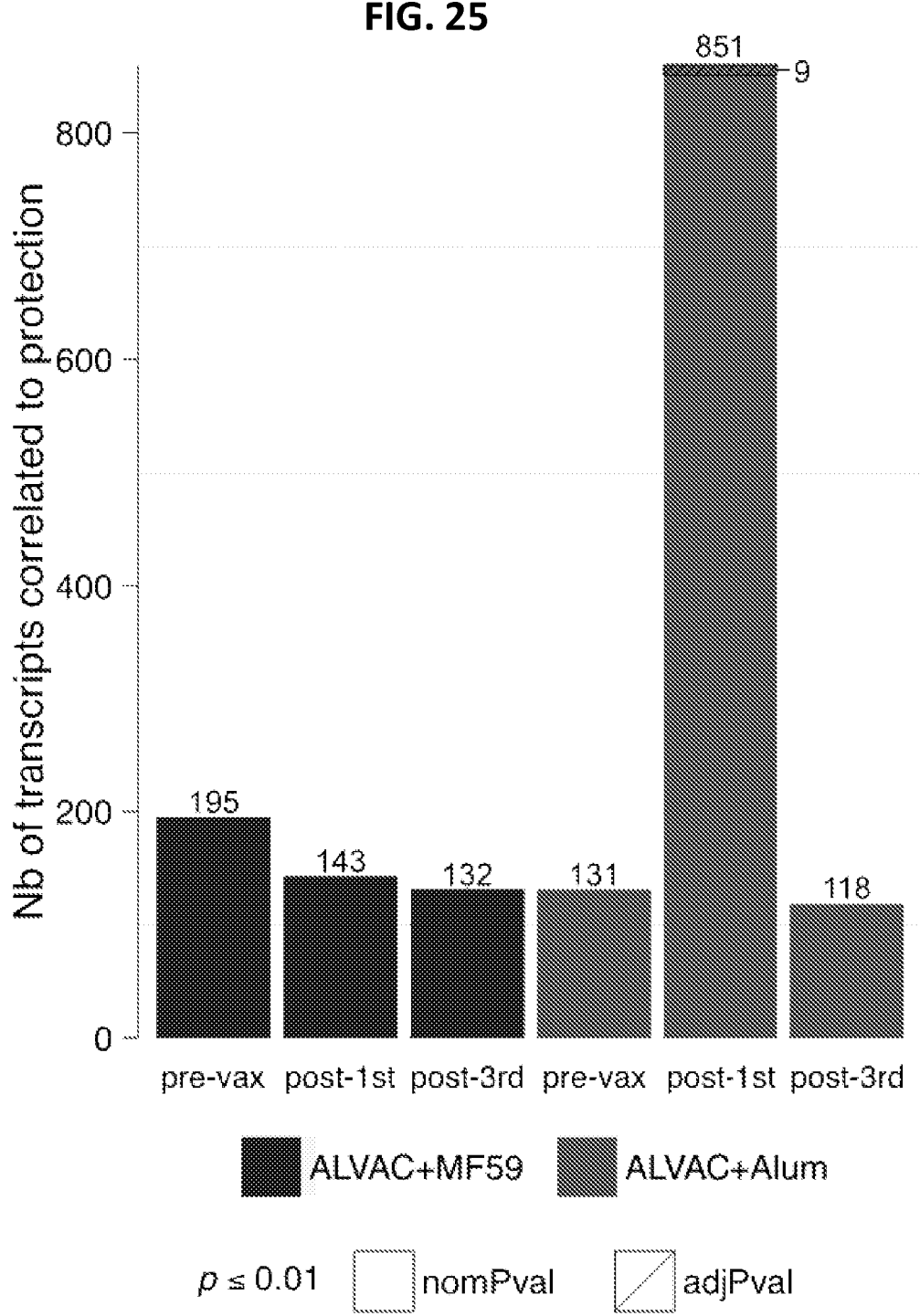

FIG. 25. Histogram presenting the number of transcripts correlated with protection for a statistical stringency of 1% on the nominal p-value (nomPval) or p-value adjusted for false positive discovery (adjPval).

Figure 26:
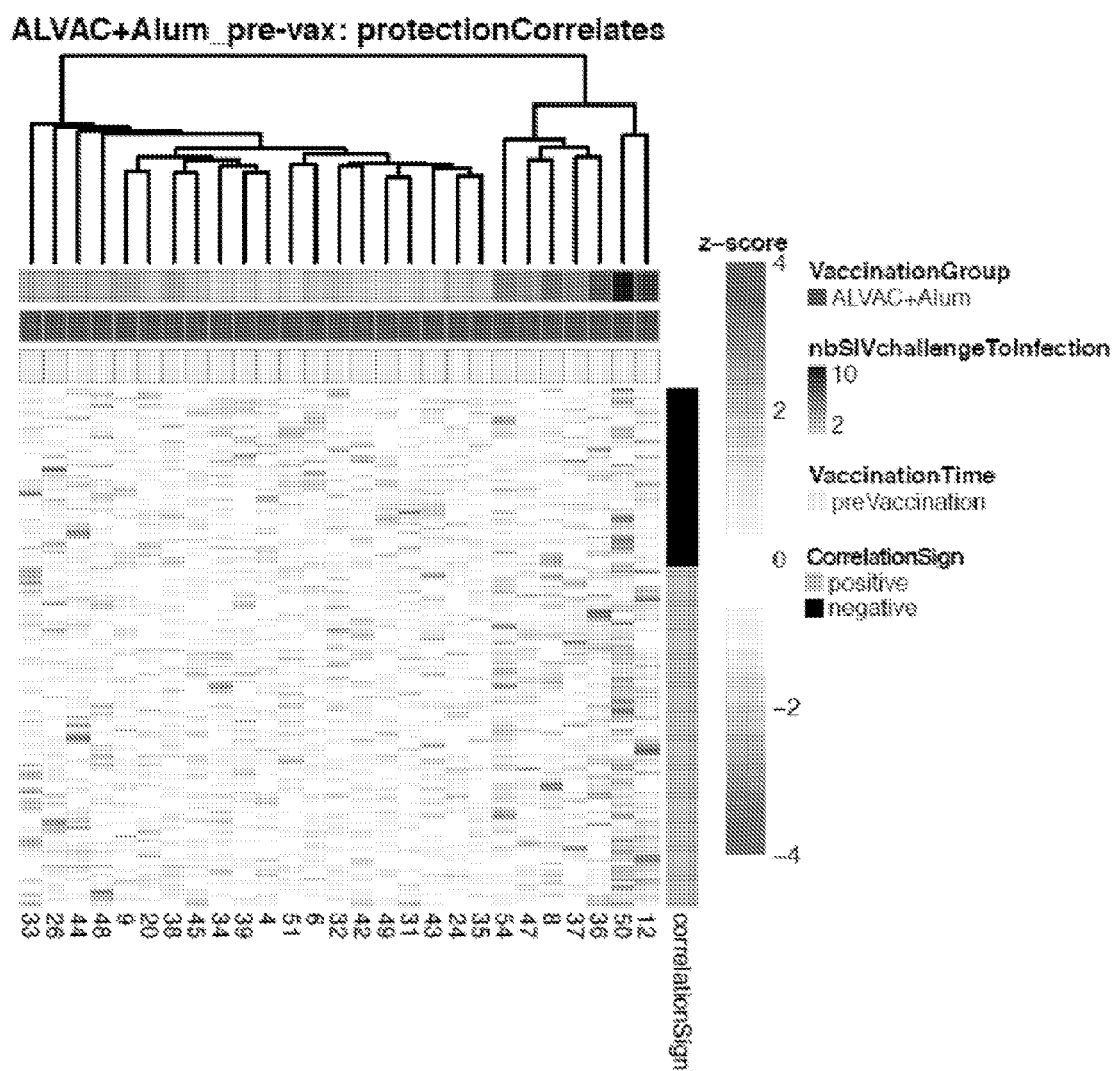

FIG. 26. Heat map representation of the expression of the 131 transcripts associated with protection by ALVAC-SIV/gp120 alum pre-vaccination. The expression intensities are represented using a greyscale. Rows correspond to transcripts and columns correspond to profiled samples. Hierarchical clustering based on Euclidian distance and complete linkage was used to regroup samples with similar gene-expression profiles.

Figure 27:
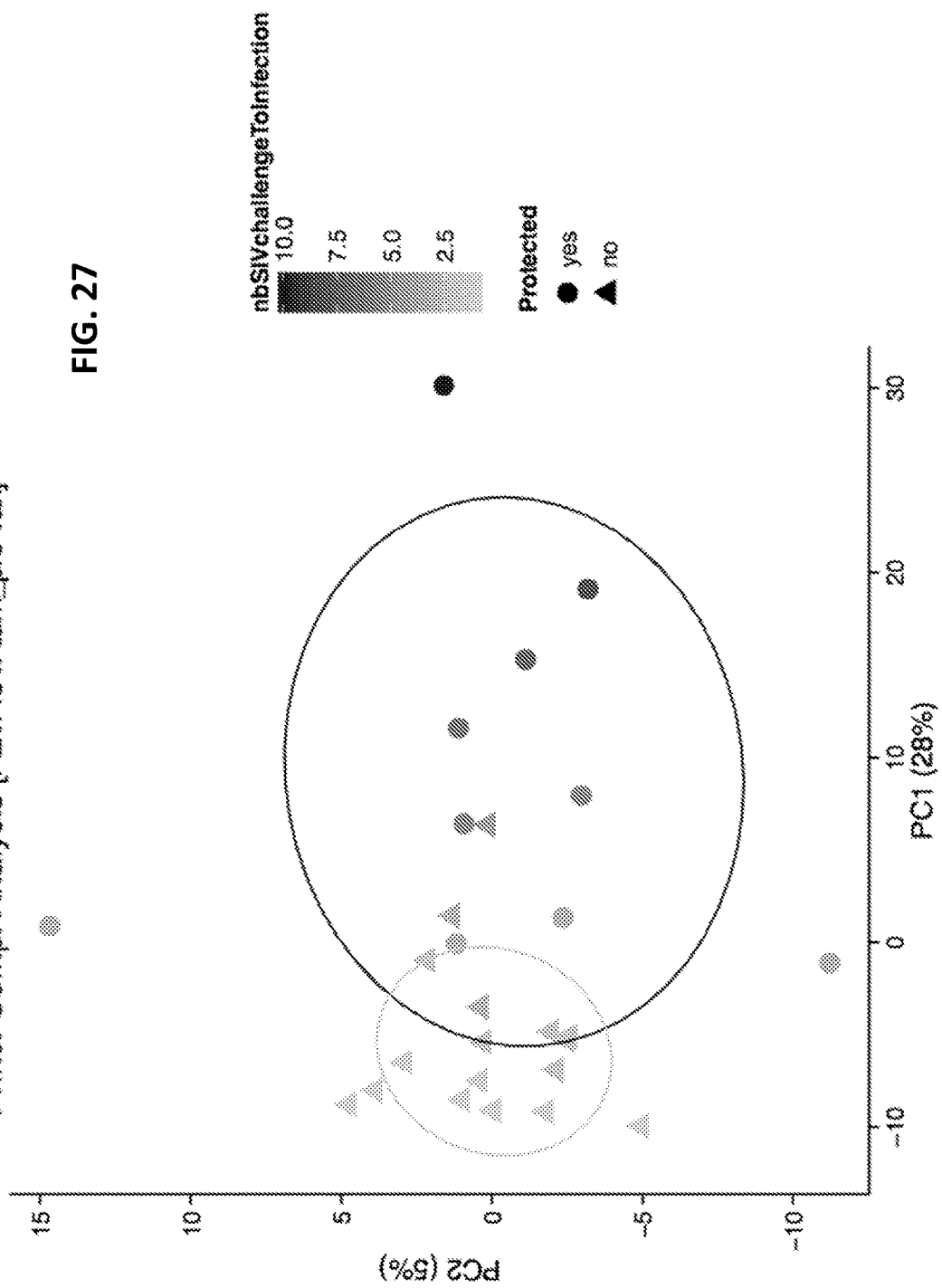

FIG. 27. Scatter plot representing the samples plotted in two dimensions using the first and second principal components. PCA was used to reduce the multidimensionality of the expression of the 131 transcripts in the 27 samples to two dimensions, represented as principal components (PC) 1 and 2. The distance between points is proportional to dissimilarity between samples. Ellipses regrouping 75% of samples of each response group (protected or non-protected) were added to accentuate the obtained sample separation.

Figure 28:
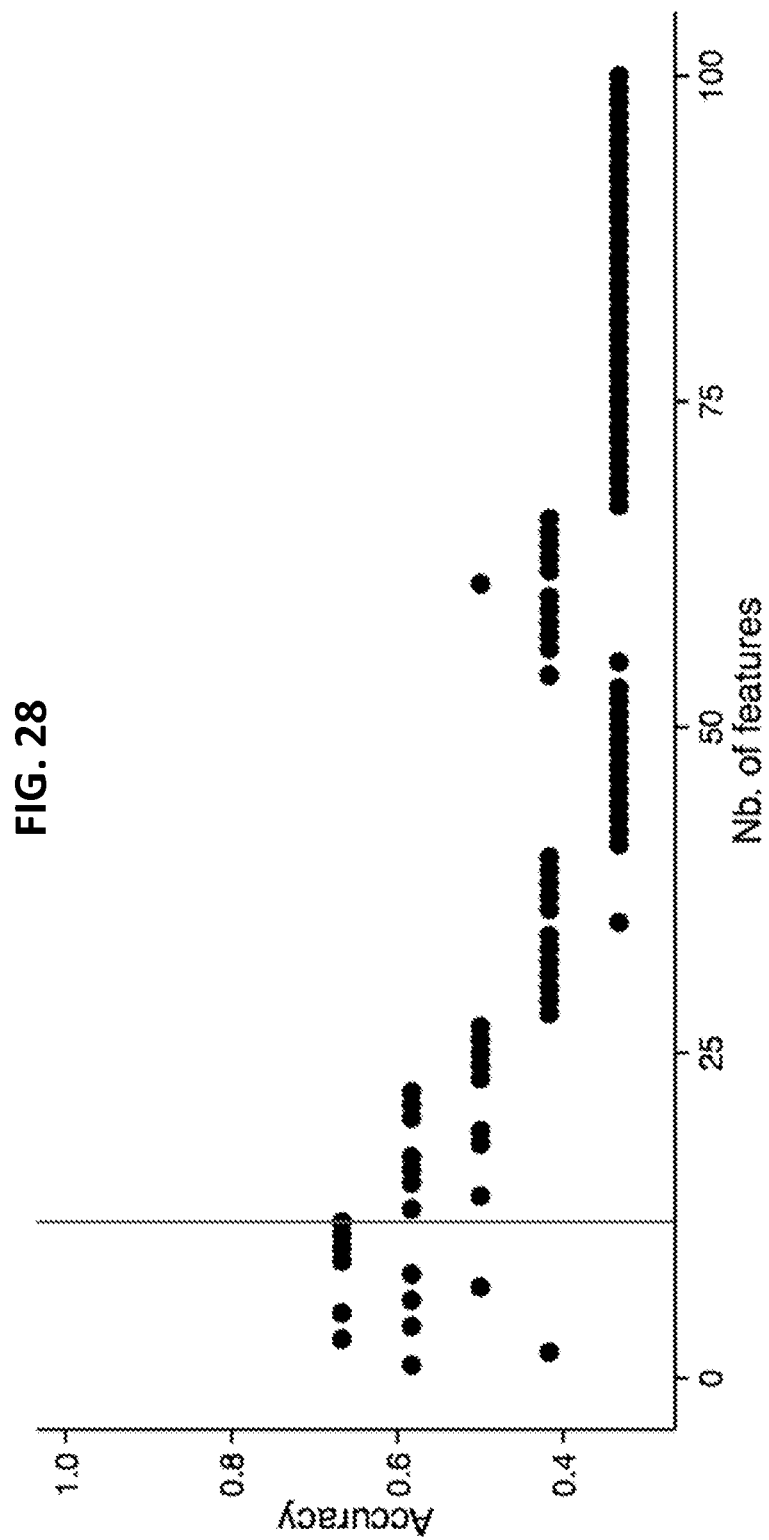

FIG. 28. Scatter plot presenting the accuracy of a naïve Bayes classifier as a function of the number of features used for the classification. Balanced accuracy as estimated by leave-one out cross-validation (LOOCV) is presented on the y-axis. Maximum accuracy (67%) was obtained for a classifier of size 12.

Figure 29:
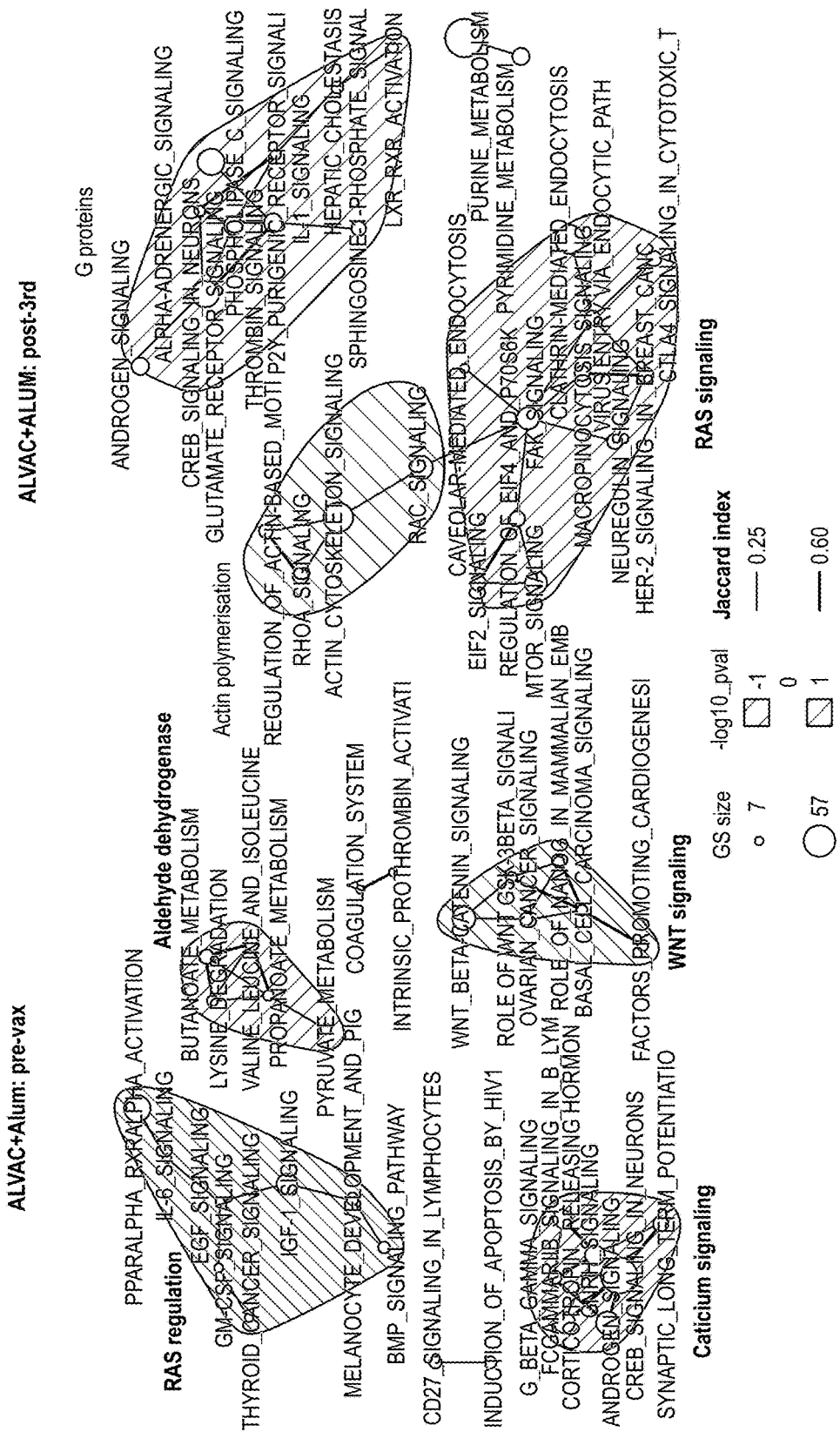

FIG. 29. Enrichment maps showing the top 50 pathways enriched among transcripts associated with protection by the ALVAC-SIV/gp120 Alum vaccine pre-vax (left panel) and post-3$^{rd}$ (right panel). Edges of the network are proportional to the number of transcripts in common between pathways. Pathways sharing transcripts in common (Jaccard Index ≥0.25) were regrouped in functional themes. The functional themes are given different colors. Only RAS related pathways were common between pre-vax and post-vax list of pathways associated with protection.

Figure 30:
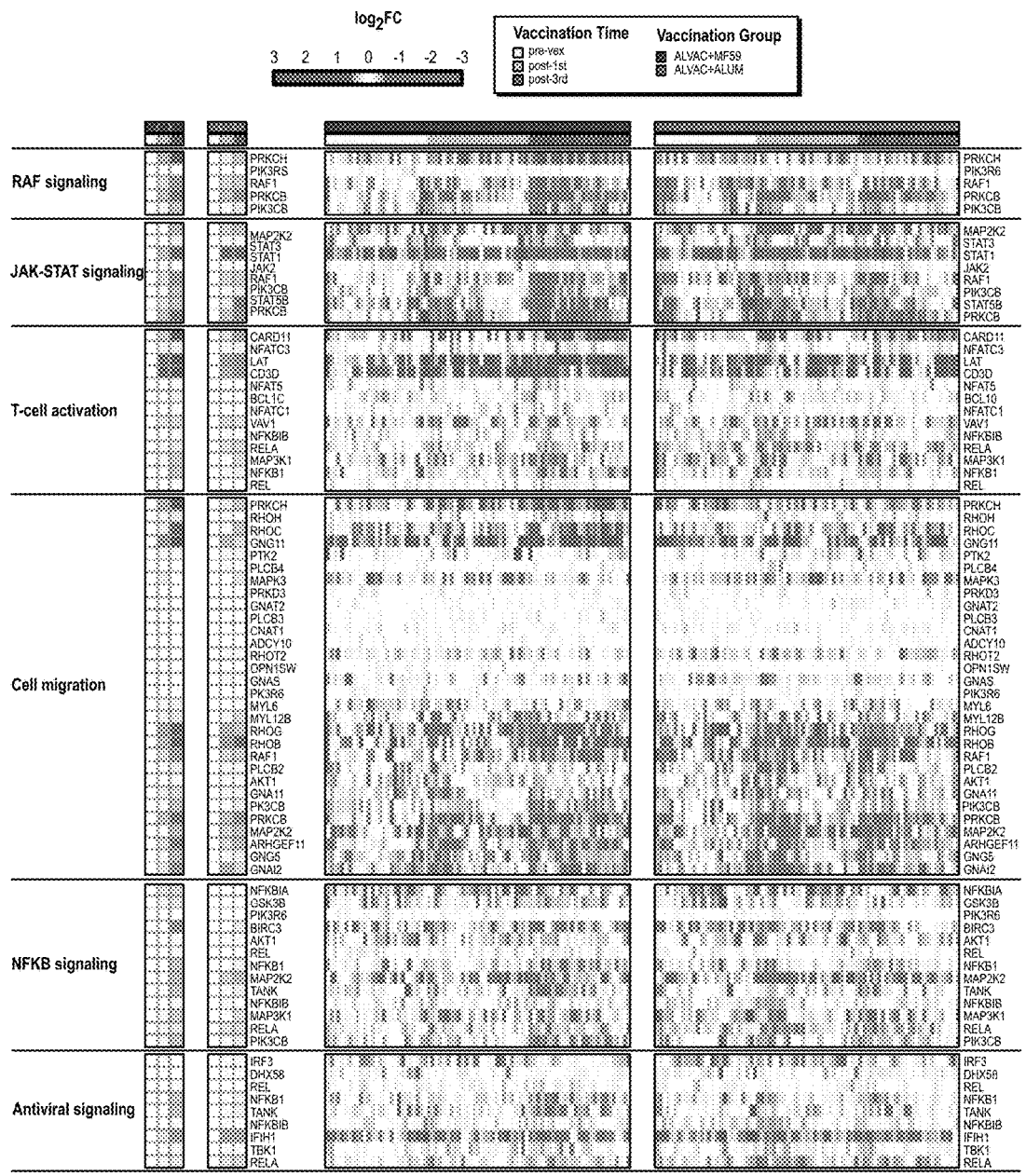

FIG. 30. Heat map that summarizes the expression of the genes common to each of the six functional modules shown in FIG. 27. The log-fold change of every gene compared to the pre-vax samples is depicted by a greyscale gradient. Left panels: mean-expression of those genes in the different conditions (vaccines×immunization step). Right panels: Expression of those genes in all the samples included in the microarray analysis.

SEQUENCES

The nucleic and amino acid sequences are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt", Jul. 7, 2016, 21.6 KB, which was created on Jan. 8, 2015 which is incorporated by reference herein. In the accompanying sequence listing:

SEQ ID NO: 1 is the amino acid sequence of rhesus epidermal growth factor (EGF).

SEQ ID NO: 2 is the amino acid sequence of human epidermal growth factor (EGF).

SEQ ID NO: 3 is the amino acid sequence of human insulin like growth factor-1 (IGF-1) preproprotein.

SEQ ID NOs: 4-10 are amino acid sequences of mature or synthetic human IGF-1.

SEQ ID NO: 11 is an amino acid sequence of a maca mulatta IGF-1.

SEQ ID NO: 12 is an amino acid sequence of an additional human IGF-1.

SEQ ID NO: 13-16 are nucleic acid sequences of primers.

SEQ ID NO: 17 is the amino acid sequence of GF SIVsmE543.

SEQ ID NO: 18 is the amino acid sequence of GF SIVmac251 full.

SEQ ID NO: 19 is the amino acid sequence of SIV$_{mac251}$ V2.

SEQ ID NOs: 20-25 are V2 peptide amino acid sequences.

SEQ ID NO: 26 is the amino acid sequence of the V2 loop from SIV$_{mac239}$.

SEQ ID NOs: 27-34 are the amino acid sequences of V2 peptides.

DETAILED DESCRIPTION OF SEVERAL EMBODIMENTS

Disclosed herein is the surprising discovery that administration of a therapeutically effective amount of an HIV immunogen in combination with an agent that stimulates the Ras pathway induces an enhanced immune response to the HIV immunogen as compared to the administration of the HIV immunogen in the absence of the agent that stimulates the Ras pathway, wherein the agent is not an aluminum salt. Accordingly, immunogenic compositions including an HIV immunogen and/or an agent that stimulates Ras pathway are provided. These compositions can be used, for example, in methods of inducing an immune response to HIV, and/or to inhibit or treat HIV infection, in a subject.

I. Terms

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "an immunogen" includes single or plural immunogens and can be considered equivalent to the phrase "at least one immunogen."

As used herein, the term "comprises" means "includes." Thus, "comprising an immunogen" means "including an immunogen" without excluding other elements.

It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments, the following explanations of terms are provided:

Adjuvant: A vehicle used to enhance antigenicity. Adjuvants can include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-$\alpha$, IFN-$\gamma$, G-CSF, LFA-3, CD72, B7-1, B7-2, OX-40L, 4-1BBL and toll-like receptor (TLR) agonists, such as TLR-9 agonists. The person of ordinary skill in the art is familiar with adjuvants (see, e.g., Singh (ed.) Vaccine Adjuvants and Delivery Systems. Wiley-Interscience, 2007). Agents that stimulate the Ras pathway can be used as adjuvants.

Administration: The introduction of a composition into a subject by a chosen route. Administration can be local or systemic. For example, if the chosen route is intravenous, the composition (such as a composition including a disclosed immunogenic composition) is administered by introducing the composition into a vein of the subject.

Agent: Any substance or any combination of substances that is useful for achieving an end or result; for example, a substance or combination of substances useful for inhibiting HIV infection in a subject. Agents include proteins, nucleic acid molecules, compounds, small molecules, organic compounds, inorganic compounds, or other molecules of interest. An agent can include a therapeutic agent (such as an anti-retroviral agent), a diagnostic agent or a pharmaceutical agent. The skilled artisan will understand that particular agents may be useful to achieve more than one result.

Agent that Stimulates the Ras Pathway: An agent, including polypeptides, nucleic acids, chemical compounds, and small molecules, that increase the activity of the Ras pathway. Specific non-limiting examples are epidermal growth factor (EGF) and insulin like growth factor (IGF). The agents can stimulate the pathways shown in FIGS. 12-15. Additional agents are disclosed below.

Alter: A change in an effective amount of a substance of interest, such as a polynucleotide or polypeptide. The amount of the substance can changed by a difference in the amount of the substance produced, by a difference in the amount of the substance that has a desired function, or by a difference in the activation of the substance. The change can be an increase or a decrease. The alteration can be in vivo or in vitro.

In several embodiments, altering an amount of a polypeptide or polynucleotide is at least about a 50%, 60%, 70%, 80%, 90%, 95%, 96%, 97%, 98%, 99%, or 100% increase or decrease in the effective amount (level) of a substance. In specific example, an increase of a polypeptide or polynucleotide is at least about a 50%, 60%, 70%, 80%, 90%, 95%, 96%, 97%, 98%, 99%, or 100% increase in a polypeptide or polynucleotide as compared to a control, a statistical normal, or a standard value chosen for specific study. In another specific example, a decrease of a polypeptide or polynucleotide, such as following the initiation of a therapeutic protocol, is at least about a 50%, 60%, 70%, 80%, 90%, 95%, 96%, 97%, 98%, 99%, or 100% decrease in a polypeptide or polynucleotide as compared to a control, a statistical normal, or a standard value chosen for specific study.

Alum: Double sulfate salts, with the formula $AM(SO_4)_2.12H_2O$, where A is a monovalent cation such as potassium or ammonium and M is a trivalent metal ion such as aluminium or chromium(III). In one embodiment, Alum is the hydrated potassium aluminium sulfate (potassium alum) with the formula $KAl(SO_4)_2.12H_2O$.

Amplification: Of a nucleic acid molecule (such as, a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No.

6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide including at least a light chain or heavy chain immunoglobulin variable region which specifically recognizes and binds an epitope of an antigen or an antigen-binding fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Antibodies of the present disclosure include those that are specific for the molecules listed.

The term antibody includes intact immunoglobulins, as well the variants and portions thereof, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA, and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs."

References to "$V_H$" or "$V_H$" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab. A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "polyclonal antibody" is an antibody that is derived from different B-cell lines. Polyclonal antibodies are a mixture of immunoglobulin molecules secreted against a specific antigen, each recognizing a different epitope. These antibodies are produced by methods known to those of skill in the art, for instance, by injection of an antigen into a suitable mammal (such as a mouse, rabbit or goat) that induces the B-lymphocytes to produce IgG immunoglobulins specific for the antigen, which are then purified from the mammal's serum.

A "chimeric antibody" has framework residues from one species, such as human, and CDRs (which generally confer antigen binding) from another species, such as a murine antibody that specifically binds an antigen of interest.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one example, all the CDRs are from the donor immunoglobulin in a humanized immunoglobulin. Constant regions need not be present, but if they are, they are substantially identical to human immunoglobulin constant regions, e.g., at least about 85-90%, such as about 95% or more identical. Hence, all parts of a humanized immunoglobulin, except possibly the CDRs, are substantially identical to corresponding parts of natural human immunoglobulin sequences. Humanized immunoglobulins can be constructed by means of genetic engineering (see for example, U.S. Pat. No. 5,585,089).

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous antigens. Examples of antigens include, but are not limited to, polypeptides, peptides, lipids, polysaccharides, and nucleic acids containing antigenic determinants, such as those recognized by an immune cell. In some examples, antigens include peptides derived from a pathogen of interest. Exemplary pathogens include bacteria, fungi, viruses and parasites. In specific examples, an antigen is derived from HIV, such as a HIV-1 Env polypeptide, gp120 polypeptide, gp41 polypeptide, or antigenic fragment thereof, such as a gp120 outer domain or fragment thereof.

Anti-retroviral agent: An agent, such as a pharmaceutical compound, that specifically inhibits a retrovirus from replicating or infecting cells. Non-limiting examples of antiretroviral drugs include entry inhibitors (e.g., enfuvirtide), CCR5 receptor antagonists (e.g., aplaviroc, vicriviroc, maraviroc), reverse transcriptase inhibitors (e.g., lamivudine, zidovudine, abacavir, tenofovir, emtricitabine, efavirenz), protease inhibitors (e.g., lopivar, ritonavir, raltegravir, darunavir, atazanavir), maturation inhibitors (e.g., alpha interferon, bevirimat and vivecon).

Anti-retroviral therapy (ART): A therapeutic treatment for HIV infection involving administration of at least one anti-retroviral agents (e.g., one, two, three or four anti-retroviral agents) to an HIV infected individual during a course of treatment. Non-limiting examples of antiretroviral agents include entry inhibitors (e.g., enfuvirtide), CCR5 receptor antagonists (e.g., aplaviroc, vicriviroc, maraviroc), reverse transcriptase inhibitors (e.g., lamivudine, zidovudine, abacavir, tenofovir, emtricitabine, efavirenz), protease inhibitors (e.g., lopivar, ritonavir, raltegravir, darunavir, atazanavir), maturation inhibitors (e.g., alpha interferon, bevirimat and vivecon). One example of an ART regimen includes treatment with a combination of tenofovir, emtricitabine and efavirenz. In some examples, ART include Highly Active Anti-Retroviral Therapy (HAART).

Array: An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least one, to at least 2, to at least 5, to at least 10, at least 20, at least 30, at least 50, at least 75, at least 100, at least 150, at least 200, at least 300, at least 500, least 550, at least 600, at least 800, at least 1000, at least 10,000, or more. In particular examples, an array includes nucleic acid molecules, such as oligonucleotide sequences that are at least 15 nucleotides in length, such as about 15-40 nucleotides in length. In particular examples, an array includes oligonucleotide probes or primers which can be used to detect if a subject produces a protective immune response.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein-based arrays include probe molecules that are or include proteins, or where the target molecules are or include proteins, and arrays including antibodies to which proteins are bound, or vice versa. In some examples, an array contains antibodies to protein, such as those listed in Table A.

In some examples, the array includes positive controls, negative controls, or both, for example molecules specific for detecting β-actin, 18S RNA, beta-microglobulin, glyceraldehyde-3-phosphate-dehydrogenase (GAPDH), and other housekeeping genes. In one example, the array includes 1 to 20 controls, such as 1 to 10 or 1 to 5 controls.

B cell: A subset of lymphocytes, that is, white blood cells (leukocytes). Mature B cells differentiate into plasma cells, which produces antibodies, and memory B cells. Mature B cells have acquired surface IgM and IgD, are capable of responding to antigen, and express characteristic markers such as CD21 and CD23. Plasma cells are terminally differentiated B cells that are the predominant antibody-secreting cells.

CD4: Cluster of differentiation factor 4 polypeptide; a T-cell surface protein that mediates interaction with the MHC class II molecule. CD4 also serves as the primary receptor site for HIV on T-cells during HIV-I infection. CD4 is known to bind to gp120 from HIV. The known sequence of the CD4 precursor has a hydrophobic signal peptide, an extracellular region of approximately 370 amino acids, a highly hydrophobic stretch with significant identity to the membrane-spanning domain of the class II MHC beta chain, and a highly charged intracellular sequence of 40 resides (Maddon, Cell 42:93, 1985).

The term "CD4" includes polypeptide molecules that are derived from CD4 include fragments of CD4, generated either by chemical (for example enzymatic) digestion or genetic engineering means. Such a fragment may be one or more entire CD4 protein domains. The extracellular domain of CD4 consists of four contiguous immunoglobulin-like regions (D1, D2, D3, and D4, see Sakihama et al., Proc. Natl. Acad. Sci. 92:6444, 1995; U.S. Pat. No. 6,117,655), and amino acids 1 to 183 have been shown to be involved in gp120 binding. For instance, a binding molecule or binding domain derived from CD4 would comprise a sufficient portion of the CD4 protein to mediate specific and functional interaction between the binding fragment and a native or viral binding site of CD4. One such binding fragment includes both the D1 and D2 extracellular domains of CD4 (D1D2 is also a fragment of soluble CD4 or sCD4 which is comprised of D1 D2 D3 and D4), although smaller fragments may also provide specific and functional CD4-like binding. The gp120-binding site has been mapped to D1 of CD4.

CD4 polypeptides also include "CD4-derived molecules" which encompasses analogs (non-protein organic molecules), derivatives (chemically functionalized protein molecules obtained starting with the disclosed protein sequences) or mimetics (three-dimensionally similar chemicals) of the native CD4 structure, as well as proteins sequence variants or genetic alleles that maintain the ability to functionally bind to a target molecule.

Conservative variants: "Conservative" amino acid substitutions are those substitutions that do not substantially affect or decrease the immunogenicity of a protein, such as gp120, or the activity of a protein, such as Epidermal Growth Factor (EFG). For example, a HIV-1 Env polypeptide, or EGF, can include up to on, up to two, up to three, up to four, or up to five conservative amino acid substitutions, or at most about 1, at most about 2, at most about 5, and most about 10, or at most about 15 conservative substitutions and induce an immune response to HIV-1 when administered to a subject. The term conservative variation can also include the use of a substituted amino acid in place of an unsubstituted parent amino acid. Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well known to one of ordinary skill in the art. The following six groups are examples of amino acids that are considered to be conservative substitutions for one another:
  1) Alanine (A), Serine (S), Threonine (T);
  2) Aspartic acid (D), Glutamic acid (E);
  3) Asparagine (N), Glutamine (Q);
  4) Arginine (R), Lysine (K);

5) Isoleucine (I), Leucine (L), Methionine (M), Valine (V); and

6) Phenylalanine (F), Tyrosine (Y), Tryptophan (W).

Non-conservative substitutions are those that reduce the immunogenicity of a protein, such as gp120. For instance, if an amino acid residue is essential for function of the protein, even an otherwise conservative substitution may disrupt that activity. Thus, a conservative substitution does not alter the basic function of a protein of interest.

Consists essentially of: In the context of the present disclosure, "consists essentially of" indicates that the expression of additional markers associated with a disorder can be evaluated, but not more than ten additional associated markers. In some examples, "consists essentially of" indicates that no more than 5 other molecules are evaluated, such as no more than 4, 3, 2, or 1 other molecules. In some examples, the expression of one or more controls is evaluated, such as a housekeeping protein or rRNA (such as 18S RNA, beta-microglobulin, GAPDH, and/or β-actin) in addition to the genes associated with the disorder. In this context "consists of" indicates that only the expression of the stated molecules is evaluated; the expression of additional molecules is not evaluated.

Contacting: Placement in direct physical association; includes both in solid and liquid form, which can take place either in vivo or in vitro. Contacting includes contact between one molecule and another molecule, for example the amino acid on the surface of one polypeptide, such as a peptide, that contacts another polypeptide. Contacting can also include contacting a cell for example by placing a polypeptide in direct physical association with a cell.

Control: A reference standard. In some embodiments, the control is a sample obtained from a healthy patient. In other embodiments, the control is a tissue sample obtained from a patient diagnosed with HIV infection. In still other embodiments, the control is a historical control or standard reference value or range of values (such as a previously tested control sample, such as a group of HIV patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500% increase or decrease.

Degenerate variant: In the context of the present disclosure, a "degenerate variant" refers to a polynucleotide encoding a peptide (such as HIV-1 envelope protein or immunogenic fragment thereof, or EGF) that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Detecting expression of a gene product: Determining the presence of and/or the level of expression of a nucleic acid molecule (such as an mRNA molecule) or a protein encoded by a gene in either a qualitative or quantitative manner. Exemplary methods include microarray analysis, RT-PCR, Northern blot, Western blot, and mass spectrometry of specimens from a subject, for example measuring levels of a gene product present in blood, serum, or another biological sample as a measure of expression.

Differential or alteration in expression: A difference or change, such as an increase or decrease, in the conversion of the information encoded in a gene into messenger RNA, the conversion of mRNA to a protein, or both. In some examples, the difference is relative to a control or reference value or range of values, such as an amount of gene expression that is expected in a subject who does not have a disorder of interest (for example esophageal adenocarcinoma, Barrett's esophagus, high grade dysplasia or low grade dysplasia of the esophagus). Detecting differential expression can include measuring a change in gene expression or a change in protein levels. Gene downregulation or deactivation includes processes that decrease transcription of a gene or translation of mRNA.

Gene downregulation includes any detectable decrease in the production of a gene product. In certain examples, production of a gene product decreases by at least 2-fold, for example at least 3-fold or at least 4-fold, as compared to a control (such an amount of gene expression in a normal cell). In one example, a control is a relative amount of gene expression in a biological sample, such as from a control subject.

Gene upregulation or activation includes processes that increase transcription of a gene or translation of mRNA. Gene upregulation includes any detectable increase in the production of a gene product. In certain examples, production of a gene product increase by at least 2-fold, for example at least 3-fold or at least 4-fold, as compared to a control (such an amount of gene expression in a normal cell). In one example, a control is a relative amount of gene expression in a biological sample, such as from a control subject.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-gp120 antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., *Pharm. Ther.* 28:341-365, 1985). Diagnostic agents or moieties include radioisotopes and other detectable labels. Detectable labels useful for such purposes are also well known in the art, and include radioactive isotopes such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$, and $^{125}I$, fluorophores, chemiluminescent agents, and enzymes.

Epitope: An antigenic determinant. These are particular chemical groups or peptide sequences on a molecule that are antigenic, such that they elicit a specific immune response, for example, an epitope is the region of an antigen to which B and/or T cells respond. An antibody binds a particular antigenic epitope, such as an epitope of an HIV-1 envelope protein.

Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance. Epitopes can also include post-translation modification of amino acids, such as N-linked glycosylation.

A "target epitope" is a particular epitope on an antigen that specifically binds an antibody of interest, such as a monoclonal antibody. In some examples, a target epitope includes the amino acid residues that contact the antibody of interest, such that the target epitope can be selected by the amino acid residues determined to be in contact with the antibody of interest.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Gene expression profile (or signature): Differential or altered gene expression can be detected by changes in the detectable amount of gene expression (such as cDNA or mRNA) or by changes in the detectable amount of proteins expressed by those genes. A distinct or identifiable pattern of gene expression, for instance a pattern of high and low expression of a defined set of genes or gene-indicative nucleic acids such as ESTs. A gene expression profile (also referred to as a signature) can be linked to disease progression (such as development of acquired immune deficiency syndrome, AIDS), or to any other distinct or identifiable condition that influences gene expression in a predictable way. Gene expression profiles can include relative as well as absolute expression levels of specific genes, and can be viewed in the context of a test sample compared to a baseline or control sample profile (such as a sample from the same tissue type from a subject who does not have an HIV infection). In one example, a gene expression profile in a subject is read on an array (such as a nucleic acid or protein array). For example, a gene expression profile can be performed using a commercially available array such as Human Genome GENECHIP® arrays from AFFYMETRIX® (Santa Clara, Calif.).

Heterologous: Originating from a different genetic source. A nucleic acid molecule that is heterologous to a cell originated from a genetic source other than the cell in which it is expressed. In one specific, non-limiting example, a heterologous nucleic acid molecule encoding an HIV-1 envelope protein is expressed in a cell, such as a mammalian cell. Methods for introducing a heterologous nucleic acid molecule in a cell or organism are well known in the art, for example transformation with a nucleic acid, including electroporation, lipofection, particle gun acceleration, and homologous recombination.

Highly active anti-retroviral therapy (HAART): A therapeutic treatment for HIV infection involving administration of multiple anti-retroviral agents (e.g., two, three or four anti-retroviral agents) to an HIV infected individual during a course of treatment. Non-limiting examples of antiretroviral agents include entry inhibitors (e.g., enfuvirtide), CCR5 receptor antagonists (e.g., aplaviroc, vicriviroc, maraviroc), reverse transcriptase inhibitors (e.g., lamivudine, zidovudine, abacavir, tenofovir, emtricitabine, efavirenz), protease inhibitors (e.g., lopivar, ritonavir, raltegravir, darunavir, atazanavir), maturation inhibitors (e.g., alpha interferon, bevirimat and vivecon). One example of a HAART regimen includes treatment with a combination of tenofovir, emtricitabine and efavirenz.

HIV Envelope protein (Env): The HIV envelope protein is initially synthesized as a longer precursor protein of 845-870 amino acids in size, designated gp160. gp160 forms a homotrimer and undergoes glycosylation within the Golgi apparatus. In vivo, it is then cleaved by a cellular protease into gp120 and gp41. gp120 contains most of the external, surface-exposed, domains of the HIV envelope glycoprotein complex, and it is gp120 which binds both to cellular CD4 receptors and to cellular chemokine receptors (such as CCR5). gp41 contains a transmembrane domain and remains in a trimeric configuration; it interacts with gp120 in a non-covalent manner.

HIV-1 gp120: An envelope protein from HIV. gp120 contains most of the external, surface-exposed, domains of the HIV envelope glycoprotein complex, and it is gp120 which binds both to cellular CD4 receptors and to cellular chemokine receptors (such as CCR5).

The mature gp120 wild-type polypeptides have about 500 amino acids in the primary sequence. The gp120 is heavily N-glycosylated giving rise to an apparent molecular weight of 120 kD. The polypeptide is comprised of five conserved regions (C1-C5) and five regions of high variability (V1-V5). Exemplary sequences of wild-type gp160 polypeptides are shown on GENBANK®, for example Accession Nos. AAB05604 and AAD12142, which are incorporated herein by reference in their entirety as available on Jun. 29, 2010. Exemplary sequences of gp120 polypeptides from HIV-1 DU156 are shown on GENBANK®, for example Accession Nos. ABD83635, AA050350 and AAT91997, which are incorporated herein by reference in their entirety as available on Sep. 27, 2010. Exemplary sequences of gp120 polypeptides from HIV-1 ZA012 are shown on GENBANK®, for example Accession No. ACF75939, which is incorporated herein by reference in its entirety as available on Sep. 27, 2010.

The gp120 core has a unique molecular structure, which comprises two domains: an "inner" domain (which faces gp41) and an "outer" domain (which is mostly exposed on the surface of the oligomeric envelope glycoprotein complex). The two gp120 domains are separated by a "bridging sheet" that is not part of either of these domains. The gp120 core comprises 25 beta strands, 5 alpha helices, and 10 defined loop segments.

The core gp120 comprises 25 β-strands, 5 α-helices and 10 defined loop segments. The polypeptide chain of gp120 is folded into two major domains, plus certain excursions that emanate from this body. The inner domain (inner with respect to the N and C termini) features a two-helix, two-strand bundle with a small five-stranded β-sandwich at its termini-proximal end and a projection at the distal end from which the V1/V2 stem emanates. The outer domain is a stacked double barrel that lies alongside the inner domain so that the outer barrel and inner bundle axes are approximately parallel. The bridging sheet (β3, β2, β21, β20) packs primarily over the inner domain, although some surface residues of the outer domain, such as Phenylalanine 382, reach in to form part of its hydrophobic core.

The V1 and V2 domains (the V1/V2 domain) of gp120 are comprised of ~50-90 residues which contain two of the most variable portions of HIV-1 (the V1 loop and the V2 loop), and one in ten residues of the V1/V2 domain are N-glycosylated. The V1/V2 domain includes approximately gp120 positions 128-194. The V3 region or V3 loop is critical for the binding of the co-receptor and determination of which of the co-receptors will bind, and includes approximately gp120 positions 293-334.

The numbering used in the gp120 derived antigens disclosed herein is relative to the HXB2 numbering scheme as set forth in *Numbering Positions in HIV Relative to HXB2CG* Bette Korber et al., Human Retroviruses and AIDS 1998: A Compilation and Analysis of Nucleic Acid and Amino Acid Sequences. Korber et al., Eds. Theoretical Biology and Biophysics Group, Los Alamos National Laboratory, Los Alamos, N. Mex., which is incorporated by reference herein in its entirety.

HIV-1 gp140: An oligomeric form of HIV envelope protein, which contains all of gp120 and the entire gp41 ectodomain.

HIV-1 gp41: A HIV protein that contains a transmembrane domain and remains in a trimeric configuration; it interacts with gp120 in a non-covalent manner. The amino acid sequence of an example of gp41 is set forth in GEN-BANK® Accession No. CAD20975 (as available on Oct. 16, 2009) which is incorporated by reference herein. It is understood that the sequence of gp41 can vary from that given in GENBANK® Accession No. CAD20975.

Homologous proteins: Proteins from two or more species that have a similar structure and function in the two or more species. For example a gp120 antigen from one species of lentivirus such as HIV-1 is a homologous antigen to a gp120 antigen from a related species such as HIV-2 or SIV. Homologous proteins often share the same protein folding and can be considered structural homologs.

Homologous proteins typically share a high degree of sequence conservation, such as at least 80%, at least 90%, at least 91%, at least 92%, at least 93%, at least 94%, or at least 95%, at least 96%, at least 97%, at least 98%, or at least 99% sequence conservation, and a high degree of sequence identity, such as at least 80%, at least 90%, at least 91%, at least 92%, at least 93%, at least 94%, or at least 95%, at least 96%, at least 97%, at least 98%, or at least 99% sequence identity.

Host cells: Cells in which a vector can be propagated and its DNA expressed, for example a disclosed antibody can be expressed in a host cell. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Human Immunodeficiency Virus (HIV): A retrovirus that causes immunosuppression in humans (HIV disease), and leads to a disease complex known as the acquired immunodeficiency syndrome (AIDS). "HIV disease" refers to a well-recognized constellation of signs and symptoms (including the development of opportunistic infections) in persons who are infected by an HIV virus, as determined by antibody or western blot studies. Laboratory findings associated with this disease include a progressive decline in T cells. HIV includes HIV type 1 (HIV-1) and HIV type 2 (HIV-2). Related viruses that are used as animal models include simian immunodeficiency virus (SIV), and feline immunodeficiency virus (FIV). Treatment of HIV-1 with HAART has been effective in reducing the viral burden and ameliorating the effects of HIV-1 infection in infected individuals.

Hybridization: To form base pairs between complementary regions of two strands of DNA, RNA, or between DNA and RNA, thereby forming a duplex molecule, for example. Hybridization conditions resulting in particular degrees of stringency will vary depending upon the nature of the hybridization method and the composition and length of the hybridizing nucleic acid sequences. Generally, the temperature of hybridization and the ionic strength (such as the Na$^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (Detects Sequences that Share at Least 80% Identity)

Hybridization: 5×-6×SSC at 65° C.-70° C. for 16-20 hours

Wash twice: 2×SSC at RT for 5-20 minutes each

Wash twice: 1×SSC at 55° C.-70° C. for 30 minutes each

Low Stringency (Detects Sequences that Share at Least 60% Identity)

Hybridization: 6×SSC at RT to 55° C. for 16-20 hours

Wash at least twice: 2×-3×SSC at RT to 55° C. for 20-30 minutes each

HXB2 numbering system: A reference numbering system for HIV protein and nucleic acid sequences, using HIV-1 HXB2 strain sequences as a reference for all other HIV strain sequences. The person of ordinary skill in the art is familiar with the HXB2 numbering system, and this system is set forth in "Numbering Positions in HIV Relative to HXB2 CG," Bette Korber et al., Human Retroviruses and AIDS 1998: A Compilation and Analysis of Nucleic Acid and Amino Acid Sequences. Korber B, Kuiken C L, Foley B, Hahn B, McCutchan F, Mellors J W, and Sodroski J, Eds. Theoretical Biology and Biophysics Group, Los Alamos National Laboratory, Los Alamos, N. Mex., which is incorporated by reference herein in its entirety. HXB2 is also known as: HXBc2, for HXB clone 2; HXB2R, in the Los Alamos HIV database, with the R for revised, as it was slightly revised relative to the original HXB2 sequence; and HXB2 CG in GENBANK™, for HXB2 complete genome. The numbering used in HIV polypeptides is relative to the HXB2 numbering scheme. For reference, the amino acid sequence of HXB2 CG is provided in GENBANK® Accession No. K03455, incorporated by reference herein as present in the database on Jan. 7, 2014).

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. "Priming an immune response" refers to pre-treatment of a subject with an adjuvant to increase the desired immune response to a later administered immunogenic agent. "Enhancing an immune response" refers to co-administration of an adjuvant and an immunogenic agent, wherein the adjuvant increases the desired immune response to the immunogenic agent compared to administration of the immunogenic agent to the subject in the absence of the adjuvant.

Immunogen: A protein or a portion thereof that is capable of inducing an immune response in a mammal, such as a mammal infected or at risk of infection with a pathogen. Administration of an immunogen can lead to protective immunity and/or proactive immunity against a pathogen of interest.

Immunogenic composition: A composition comprising an immunogenic polypeptide that induces a measurable CTL response against virus expressing the immunogenic polypeptide, or induces a measurable B cell response (such as production of antibodies) against the immunogenic polypeptide. In one example, an "immunogenic composition" is composition including an HIV polypeptide that induces a measurable CTL response against virus expressing gp120 polypeptide, or induces a measurable B cell response (such as production of antibodies) against a gp120 polypeptide. It further refers to isolated nucleic acids encoding an antigen, such as a nucleic acid that can be used to express the antigen (and thus be used to elicit an immune response against this peptide).

For in vitro use, an immunogenic composition may consist of the isolated protein, peptide epitope, or nucleic acid encoding the protein, or peptide epitope. For in vivo use, the immunogenic composition will typically include the protein, immunogenic peptide or nucleic acid in pharmaceutically acceptable carriers, and/or other agents. Any particular peptide, such as a HIV peptide, can be readily tested for its ability to induce a CTL or B cell response by art-recognized assays. Immunogenic compositions can include adjuvants, which are well known to one of skill in the art. In some embodiments, the immunogenic composition further includes an agent that stimulates the Ras pathway.

Immunogenic polypeptide: A polypeptide which comprises an allele-specific motif, an epitope or other sequence such that the peptide will bind an MHC molecule and induce an immune response, such as a cytotoxic T lymphocyte ("CTL") response, and/or a B cell response (for example, antibody production), and/or a T-helper lymphocyte response against the antigen from which the immunogenic polypeptide is derived.

Inhibiting or treating a disease: Inhibiting the full development of a disease or condition, for example, in a subject who is at risk for a disease such as acquired immunodeficiency syndrome (AIDS). "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a cell, for example a B cell, a nucleic acid, peptide, protein or antibody) has been substantially separated, produced apart from, or purified away from other biological components in the cell of the organism in which the component naturally occurs, such as, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides, and proteins prepared by recombinant expression in a host cell as well as chemically synthesized nucleic acids.

Label: An agent capable of detection, for example by ELISA, spectrophotometry, flow cytometry, or microscopy.

For example, a label can be attached to a nucleic acid molecule or protein, thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Labels can be non-naturally occurring molecules. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998). In a particular example, a label is conjugated to a binding agent that specifically binds to an ASCVD and MI associated protein, disclosed herein.

Level of Expression: An amount, such as of a protein or an mRNA, that can be measured in a biological sample.

Marker: A biological marker, such as a polypeptide or a polynucleotide, that can be detected in a biological sample from a subject. A polypeptide marker can be about 95%, about 96%, about 97%, about 98%, about 99% or 100% identical to a reference amino acid sequence, such as a known amino acid sequence provided in a database such as GENBANK® or EMBL®. In some embodiments, an antibody that specifically binds a reference sequence of interest will bind the marker in a biological sample. A polynucleotide marker can be about 95%, 96%, 97%, 98%, 99% or 100% identical to a reference nucleic acid sequence, such as a known nucleic acid sequence provided in a database such as GENBANK® or EMBL®. In some embodiments, a probe that specifically hybridizes to a reference sequence under very stringent conditions will bind the polynucleotide marker, or primers designed to amplify the reference sequence will amplify the polynucleotide marker.

Mammal: This term includes both human and non-human mammals. Examples of mammals include, but are not limited to: humans, pigs, cows, goats, cats, dogs, rabbits, rats, and mice.

Mass Spectrometry: A process used to separate and identify molecules based on their mass. Mass spectrometry ionizes chemical compounds to generate charged molecules or molecule fragments and measures their mass-to-charge ratios. In a typical MS procedure, as sample is ionized. The ions are separated according to their mass-to-charge ratio, and the ions are dynamically detected by some mechanism capable of detecting energetic charged particles. The signal is processed into the spectra of the masses of the particles of that sample. The elements or molecules are identified by correlating known masses by the identified masses. "Time-of-flight mass spectrometry" (TOFMS) is a method of mass spectrometry in which an ion's mass-to-charge ratio is determined via a time measurement. Ions are accelerated by an electric field of known strength. This acceleration results in an ion having the same kinetic energy as any other ion that has the same charge. The velocity of the ion depends on the mass-to-charge ratio. The time that it subsequently takes for the particle to reach a detector at a known distance is measured. This time will depend on the mass-to-charge ratio of the particle (heavier particles reach lower speeds). From this time and the known experimental parameters one can find the mass-to-charge ratio of the ion. "Liquid chromatography-mass spectrometry" or "LC-MS" is a chemistry technique that combines the physical separation capabilities of liquid chromatography (or HPLC) with the mass analysis capabilities of mass spectrometry. Liquid chromatography mass spectrometry (LC-MS) separates compounds chromatographically before they are introduced to the ion source and mass spectrometer. It differs from gas chromatography (GC-MS) in that the mobile phase is liquid, usually a mixture of water and organic solvents, instead of gas and the ions fragments. Most commonly, an electrospray ionization source is used in LC-MS.

Multiple reaction monitoring (MRM): A mass spectrometry based method in which absolute quantification of a targeted protein(s) can be obtained. In this method external or internal standards are used. Often a known quantity of a synthetic stable isotopically labeled peptide matching each of the targeted peptides that represent unique the protein is added into each sample being quantified. Comparison of the peak of the endogenous peptide to the labeled standard peptide allows absolute quantitation. MRM can be multiplexed easily, allowing multiple phosphorylation sites and/or multiple proteins to be assessed simultaneously.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Nucleic acid array: An arrangement of nucleic acids (such as DNA or RNA) in assigned locations on a matrix, such as that found in cDNA arrays, or oligonucleotide arrays.

Nucleic acid molecules representing genes: Any nucleic acid, for example DNA (intron or exon or both), cDNA, or RNA (such as mRNA), of any length suitable for use as a probe or other indicator molecule, and that is informative about the corresponding gene, such the proteins specified herein.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended in a unit dosage form containing one or more measured doses of the composition suitable to induce the desired anti-HIV immune response. It may also be accompanied by medications for its use for treatment purposes. The unit dosage form may be, for example, in a sealed vial that contains sterile contents or a syringe for injection into a subject.

Polymerase Chain Reaction (PCR): An in vitro amplification technique that increases the number of copies of a nucleic acid molecule (for example, a nucleic acid molecule in a sample or specimen). The product of a PCR can be characterized by standard techniques known in the art, such as electrophoresis, restriction endonuclease cleavage patterns, oligonucleotide hybridization or ligation, and/or nucleic acid sequencing.

In some examples, PCR utilizes primers, for example, DNA oligonucleotides 10-100 nucleotides in length, such as about 15, 20, 25, 30 or 50 nucleotides or more in length (such as primers that can be annealed to a complementary target DNA strand by nucleic acid hybridization to form a hybrid between the primer and the target DNA strand. Primers can be selected that include at least 15, at least 20, at least 25, at least 30, at least 35, at least 40, at least 45, at least 50 or more consecutive nucleotides of a nucleotide sequence of interest. Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990).

Polypeptide: Any chain of amino acids, regardless of length or post-translational modification (e.g., glycosylation or phosphorylation). In one embodiment, the polypeptide is a gp120 polypeptide. In one embodiment, the polypeptide is a disclosed antibody or a fragment thereof. A "residue" refers to an amino acid or amino acid mimetic incorporated in a polypeptide by an amide bond or amide bond mimetic. A polypeptide has an amino terminal (N-terminal) end and a carboxy terminal (C-terminal) end. A protein can include multiple polypeptide chains; for example, HIV Env protein includes a gp120 polypeptide chain and a gp41 polypeptide chain.

Polypeptide modifications: Polypeptides can be modified by a variety of chemical techniques to produce derivatives having essentially the same activity and conformation as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups.

Prime-boost vaccination: An immunotherapy including administration of a first immunogenic composition (the primer vaccine) followed by administration of a second immunogenic composition (the booster vaccine) to a subject to induce an immune response. The primer vaccine and/or the booster vaccine include a vector (such as a viral vector, RNA, or DNA vector) expressing the antigen to which the immune response is directed. The booster vaccine is administered to the subject after the primer vaccine; the skilled artisan will understand a suitable time interval between administration of the primer vaccine and the booster vaccine, and examples of such timeframes are disclosed herein. In some embodiments, the primer vaccine, the booster vaccine, or both primer vaccine and the booster vaccine additionally include an adjuvant. In one non-limiting example, the primer vaccine is a DNA-based vaccine (or other vaccine based on gene delivery), and the booster vaccine is a protein subunit or protein nanoparticle based vaccine.

Primers: Short nucleic acid molecules, for instance DNA oligonucleotides 10-100 nucleotides in length, such as about 15, 20, 25, 30 or 50 nucleotides or more in length, such as this number of contiguous nucleotides of a nucleotide sequence encoding a protein of interest or other nucleic acid molecule. Primers can be annealed to a complementary target DNA strand by nucleic acid hybridization to form a hybrid between the primer and the target DNA strand. Primer pairs can be used for amplification of a nucleic acid sequence, such as by PCR or other nucleic acid amplification methods known in the art.

Methods for preparing and using nucleic acid primers are described, for example, in Sambrook et al. (In *Molecular Cloning: A Laboratory Manual*, CSHL, New York, 1989), Ausubel et al. (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular primer increases with its length. In one example, a primer includes at least 15 consecutive nucleotides of a nucleotide molecule, such as at least 18 consecutive nucleotides, at least 20, at least 25, at least 30, at least 35, at least 40, at least 45, at least 50 or more consecutive nucleotides of a nucleotide sequence (such as a gene, mRNA or cDNA). Such primers can be used to amplify a nucleotide sequence of interest, such as the markers shown in FIGS. 9-12, MORC3, STAU1, Loc710822, ILF3, HERC3, NAA38, PECR, MAP2K, LOC716474, EWSR, MGAT2 or NOSIP, for example using PCR.

Probe: A short sequence of nucleotides, such as at least 8, at least 10, at least 15, at least 20, at least 21, at least 25, at least 30, at least 35, at least 40, at least 45, at least 50, at least 55, at least 60, at least 65, at least 70, at least 75, at least 80, at least 85, at least 90, at least 95 or even greater than 100 nucleotides in length, used to detect the presence of a complementary sequence by molecular hybridization. In particular examples, oligonucleotide probes include a label that permits detection of oligonucleotide probe:target sequence hybridization complexes. Such an oligonucleotide probe can also be used on a nucleic acid array, for example to detect a nucleic acid molecule in a biological sample contacted to the array. In some examples, a probe is used to detect the presence of a nucleic acid molecule for a markers shown in FIGS. 9-12, or is used to detect MORC3, STAU1, Loc710822, ILF3, HERC3, NAA38, PECR, MAP2K, LOC716474, EWSR, MGAT2, or NOSIP.

Protein Kinase B (PKB, AKT): A serine/threonine-specific protein kinase that plays a key role in multiple cellular processes such as glucose metabolism, apoptosis, cell proliferation, transcription and cell migration. Akt1 is involved in cellular survival pathways, by inhibiting apoptotic processes. Akt1 is also able to induce protein synthesis pathways.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is more pure than in an environment including a complex mixture of oligonucleotides.

Ras: A G protein, or a guanosine-nucleotide-binding protein, that shares structure and function with Ras family member. Ras is a single-subunit small GTPase, which is related in structure to the $G_\alpha$ subunit of heterotrimeric G proteins (large GTPases). G proteins function as binary signaling switches with "on" and "off" states. In the "off" state it is bound to the nucleotide guanosine diphosphate (GDP), while in the "on" state, Ras is bound to guanosine triphosphate (GTP). When Ras is activated by incoming signals, it affects other proteins in the Ras pathway (see FIGS. 9-12), which ultimately affects cell growth, differentiation and/or survival. Ras is attached to the cell membrane. There are three human ras genes that encode extremely similar proteins made up of chains of 188 to 189 amino acids, designated H-Ras, N-Ras and K-Ras4A and K-Ras4B (the two K-Ras proteins arise from alternative splicing). Ras activates the mitogen-activate protein (MAP) kinase cascade and the AKT pathway.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is a protein encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sample (or biological sample): A biological specimen containing genomic DNA, RNA (including mRNA), protein, or combinations thereof, obtained from a subject. Examples include, but are not limited to, peripheral blood, serum, plasma, tissue, cells, urine, saliva, tissue biopsy, fine needle aspirate, surgical specimen, and autopsy material.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are.

Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, Gene 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

Specific Binding Agent: An agent that binds substantially or preferentially only to a defined target such as a protein, enzyme, polysaccharide, oligonucleotide, DNA, RNA, recombinant vector or a small molecule. Thus, a nucleic acid-specific binding agent binds substantially only to the defined nucleic acid, such as RNA, or to a specific region within the nucleic acid. For example, a "specific binding agent" includes an antisense compound (such as an antisense oligonucleotide, siRNA, miRNA, shRNA or ribozyme) that binds substantially to a specified RNA.

A protein-specific binding agent binds substantially only the defined protein, or to a specific region within the protein. For example, a "specific binding agent" includes antibodies and other agents that bind substantially to a specified polypeptide. Antibodies can be monoclonal or polyclonal antibodies that are specific for the polypeptide, as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999).

T Cell: A white blood cell critical to the immune response. T cells include, but are not limited to, CD4$^+$ T cells and CD8$^+$ T cells. A CD4$^+$ T lymphocyte is an immune cell that carries a marker on its surface known as "cluster of differentiation 4" (CD4). These cells, also known as helper T cells, help orchestrate the immune response, including antibody responses as well as killer T cell responses. Th1 and Th2 cells are functional subsets of helper T cells. Th1 cells secrete a set of cytokines, including interferon-gamma, and whose principal function is to stimulate phagocyte-mediated defense against infections, especially related to intracellular microbes. Th2 cells secrete a set of cytokines, including interleukin (IL)-4 and IL-5, and whose principal functions are to stimulate IgE and eosinophil/mast cell-mediated immune reactions and to downregulate Th1 responses.

CD8+ T cells carry the "cluster of differentiation 8" (CD8) marker. In one embodiment, a CD8 T cells is a cytotoxic T lymphocytes. In another embodiment, a CD8 cell is a suppressor T cell.

Therapeutic agent: Used in a generic sense, it includes treating agents, prophylactic agents, and replacement agents. A therapeutic agent is used to ameliorate a specific set of conditions in a subject with a disease or a disorder, such as AIDS or an HIV infection.

Therapeutically Effective Amount: An amount of a composition that alone, or together with an additional therapeutic agent(s) (for example nucleoside/nucleotide reverse transcriptase inhibitors, a non-nucleoside reverse transcriptase inhibitors, protease inhibitors, fusion/entry inhibitors or integrase inhibitors) induces the desired response (e.g., inhibition of HIV infection or replication, or a protective immune response). In several embodiments, a therapeutically effective amount is the amount necessary to reduce a sign or symptom of AIDS, and/or to decrease viral titer in a subject. When administered to a subject, a dosage will generally be used that will achieve target tissue concentrations that has been shown to achieve a desired in vitro effect.

In one example, a desired response is to inhibit HIV replication in a cell to which the therapy is administered. HIV replication does not need to be completely eliminated for the composition to be effective. For example, a composition can decrease HIV replication by a desired amount, for example by at least 10%, at least 20%, at least 50%, at least 60%, at least 70%, at least 80%, at least 90%, at least 95%, at least 98%, or even at least 100% (elimination of HIV), as compared to HIV replication in the absence of the composition.

In another example, a desired response is to inhibit HIV infection. The HIV infected cells do not need to be completely eliminated for the composition to be effective. For example, a composition can decrease the number of HIV infected cells by a desired amount, for example by at least 10%, at least 20%, at least 50%, at least 60%, at least 70%, at least 80%, at least 90%, at least 95%, at least 98%, or even at least 100% (elimination of detectable HIV infected cells), as compared to the number of HIV infected cells in the absence of the composition.

A therapeutically effective amount of an agent including at least one immunogen can be administered in a single dose, or in several doses, for example daily, during a course of treatment. However, the therapeutically effective amount can depend on the subject being treated, the severity and type of the condition being treated, and the manner of administration. For example, a therapeutically effective amount of such agent can vary from about 1 µg-10 mg per 70 kg body weight if administered intravenously. A unit dosage form of the agent can be packages in a therapeutic amount, or in multiples of the therapeutic amount, for example, in a vial (e.g., with a pierceable lid) or syringe having sterile components.

Transduced and Transformed: A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule is introduced into such a cell, including transformation with plasmid vectors, and introduction of naked DNA by electroporation, lipofection, and particle gun acceleration.

Translation: The process in which cellular ribosomes create proteins. In translation, messenger RNA (mRNA) produced by transcription is decoded by a ribosome complex to produce a specific polypeptide.

Under conditions sufficient for: A phrase that is used to describe any environment that permits a desired activity. In one example the desired activity is sulfation of a tyrosine residue. In another example the desired activity is treatment of HIV infection.

Upregulated or activation: When used in reference to the expression of a nucleic acid molecule, such as a gene, refers to any process which results in an increase in production of a gene product, such as a protein. A gene product can be RNA (such as mRNA, rRNA, tRNA, and structural RNA) or protein. Therefore, gene upregulation or activation includes processes that increase transcription of a gene or translation of mRNA.

Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene upregulation can include inhibition of repression as well as stimulation of expression above an existing level. Examples of processes that increase translation include those that increase translational initiation, those that increase translational elongation and those that increase mRNA stability.

Gene upregulation includes any detectable increase in the production of a gene product. In certain examples, production of a gene product increases by at least 1.5-fold, such as at least 2-fold, at least 3-fold or at least 4-fold, as compared to a control. In one example, a control is a relative amount of gene expression in a biological sample, such as from a subject that was not administered a vaccine.

Vaccine: Composition that when administered to a subject, induces a decrease of the severity of the symptoms of a disorder or disease. In one specific, non-limiting embodiment, a vaccine decreases the severity of the symptoms associated with HIV infection and/or decreases the viral load.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

II. Immunogenic Compositions

As disclosed herein, administration of a therapeutically effective amount of an HIV immunogen in combination with an agent that stimulates the Ras pathway indices an enhanced immune response to HIV compared to the administration of the HIV immunogen in the absence of the agent that stimulates the Ras pathway. Accordingly, immunogenic compositions including an HIV immunogen and/or an agent that stimulates the Ras pathway are provided. These compositions can be used in the disclosed methods of inducing an immune response to HIV, and/or to inhibit or treat HIV infection, in vertebrate animals (such as mammals, for example primates, such as humans) to HIV.

A. HIV Immunogens

The HIV immunogen can include amino acid sequences from a HIV envelope protein (e.g., gp160 or gp120) from an HIV strain or an immunogenic fragment thereof. The immunogen can be an HIV-1 or an HIV-2 immunogen. HIV-1 can be classified into four groups: the "major" group M, the "outlier" group O, group N, and group P. Within group M, there are several genetically distinct clades (or subtypes) of HIV-1. The immunogen can be derived from any subtype of HIV, such as groups M, N, O, or P or clade A, B, C, D, F, G, H, J or K and the like. HIV envelope proteins from the different HIV clades, as well as nucleic acid sequences encoding such proteins and methods for the manipulation and insertion of such nucleic acid sequences into vectors, are known (see, e.g., HIV Sequence Compendium, Division of AIDS, National Institute of Allergy and Infectious Diseases (2013); H W Sequence Database (hiv-web.lanl.gov/content/hiv-db/mainpage.html); Sambrook et al., Molecular Cloning, a Laboratory Manual, 2d edition, Cold Spring Harbor Press, Cold Spring Harbor, N.Y. (1989); Ausubel et al., Current Protocols in Molecular Biology, Greene Publishing Associates and John Wiley & Sons, New York, N.Y. (1994)). Exemplary native HIV-1 envelope protein sequences are available in the HIV Sequence Database (hiv-web.lanl.gov/content/hiv-db/mainpage.html).

The HIV immunogen can be any HIV protein or fragment thereof that induces an immune response to HIV that inhibits or neutralizes HIV infection. Examples include native HIV envelope proteins, such as HIV-1 envelope proteins (see, e.g., HIV Sequence Compendium, Division of AIDS, National Institute of Allergy and Infectious Diseases (2013); H W Sequence Database (hiv-web.lanl.gov/content/hiv-db/mainpage.html), as well as engineered HIV envelope proteins, for example HIV envelope proteins engineered with stabilizing mutations such as introduced di-sulfide bonds deletion or addition of N-linked glycosylation sites, deletion or modification of the V1-V5 domains, deletion or modification of the outer or inner domain, or the bridging sheet, including stabilized soluble trimers that can be cleaved to adopt a near-native conformation. The person of skill in the art is familiar with HIV envelope proteins and can readily determine if an HIV envelope protein induces a neutralizing immune response to HIV. Exemplary HIV envelope proteins include gp160, gp140, and/or gp120.

In some embodiments, the HIV immunogen is a gp160, gp140, or gp120 protein or immunogenic fragment thereof. For example, in some embodiments, the HIV immunogen can be a native HIV-1 gp120 polypeptide sequence available in the HIV Sequence Database (hiv-web.lanl.gov/content/hiv-db/mainpage.html). In some embodiments the HIV immunogen includes an amino acid sequence having at least 75% (for example at least 85%, 90%, 95%, 96%, 97%, 98% or 99%) sequence identity to a native HIV-1 gp120 polypeptide sequence, such a native HIV-1 gp120 polypeptide sequence available in the HIV Sequence Database (hiv-web.lanl.gov/content/hiv-db/mainpage.html), wherein the HIV immunogen can induce an immune response to HIV-1 in a subject.

In several embodiments, the HIV immunogen includes or consists of at least 50 (such as at least 100, at least 150, at least 200, at least 250, at least 300, at least 350, at least 400, at least 450, at least 500, at least 550, at least 600, at least 650, at least 700, at least 750, or at least 800) consecutive amino acids of a native HIV-1 gp120 polypeptide sequence available in the HIV Sequence Database (hiv-web.lanl.gov/content/hiv-db/mainpage.html). In additional embodiments, the HIV immunogen includes or consists of at least 50 (such as at least 100, at least 150, at least 200, at least 250, at least 300, at least 350, at least 400, at least 450, at least 500, at least 550, at least 600, at least 650, at least 700, at least 750, or at least 800) consecutive amino acids of an amino acid sequence having at least 75% (for example at least 85%, 90%, 95%, 96%, 97%, 98% or 99%) sequence identity to a native HIV gp120 polypeptide sequence, such a native HIV-1 gp120 polypeptide sequence available in the HIV Sequence Database (hiv-web.lanl.gov/content/hiv-db/mainpage.html), wherein the HIV immunogen can induce an immune response to HIV-1 in a subject.

In several embodiments, the HIV immunogen (or an immunogenic composition including such a molecule) can be used to induce an immune response to HIV in a subject. In several such embodiments, induction of the immune response includes production of broadly neutralizing antibodies to HIV. Methods to assay for neutralization activity are known to the person of ordinary skill in the art and are further described herein, and include, but are not limited to, a single-cycle infection assay as described in Martin et al. (2003) *Nature Biotechnology* 21:71-76. In this assay, the level of viral activity is measured via a selectable marker whose activity is reflective of the amount of viable virus in the sample, and the $IC_{50}$ is determined. In other assays, acute infection can be monitored in the PM1 cell line or in primary cells (normal PBMC). In this assay, the level of viral activity can be monitored by determining the p24 concentrations using ELISA. See, for example, Martin et al. (2003) *Nature Biotechnology* 21:71-76. Additional neutralization assays are described in the disclosed examples.

Several embodiments include an HIV immunogen including a multimer of any of a HIV envelope protein or fragment thereof, for example, a multimer including 2, 3, 4, 5, 6, 7, 8, 9, or 10 or more of a HIV envelope protein or fragment thereof.

In some embodiments, the HIV immunogen is linked to a heterologous protein derived from another protein of human, animal, vegetal or synthetic origin, which serves to either stabilize its structure, increase its potency, or improve its pharmacological properties such as plasma half-life or resistance to protease digestion. Examples of heterologous proteins include (but are not limited to) tetanus toxoid, cholera toxin beta-subunit, albumin, or the Fc portion of human immunoglobulin (Ig)G or IgM.

In some embodiments, the HIV immunogen can be covalently linked to a carrier, which is an immunogenic macromolecule. When bound to a carrier, the bound polypeptide becomes more immunogenic. Carriers are chosen to increase the immunogenicity of the bound molecule and/or to elicit higher titers of antibodies against the carrier which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)).

It is understood in the art that some variations can be made in the amino acid sequence of a protein without affecting the activity of the protein. Such variations include insertion of amino acid residues, deletions of amino acid residues, and substitutions of amino acid residues. These variations in sequence can be naturally occurring variations or they can be engineered through the use of genetic engineering techniques known to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6, both of which are incorporated herein by reference in their entirety. Thus, in additional embodiments, the HIV immunogen can include one or more amino acid substitutions compared to the native HIV sequence. For example, in some embodiments, the HIV immunogen includes up to 20 amino acid substitutions compared to the native HIV sequence, such as native HIV polypeptide sequence available in the HIV Sequence Database (hiv-web.lanl.gov/content/hiv-db/mainpage.html). Alternatively, the HIV immunogen can have none, or up to 1, 2, 3, 4, 5, 6, 7, 8, 9, 10, 11, 12, 13, 14, 15, 16, 17, 18 or 19 amino acid substitutions compared to the native sequence, wherein the polypeptide induces an immune response to HIV in a subject. Manipulation of the nucleotide sequence encoding the HIV immunogen thereof using standard procedures, including in one specific, non-limiting, embodiment, site-directed mutagenesis or in another specific, non-limiting, embodiment, PCR, can be used to produce such variants. Alternatively, the sulfated HIV envelope proteins or fragment thereof can be synthesized using standard methods. The simplest modifications involve the substitution of one or more amino acids for amino acids having similar biochemical properties. These so-called conservative substitutions are likely to have minimal impact on the activity of the resultant protein.

Standard methods in the art can be used to make the HIV immunogen. For example, recombinant DNA technology can be used to generate a nucleic acid encoding the disclosed peptides, and from which the peptide can be expressed and purified. Such methods are known to the skilled artisan and further described herein. In addition to recombinant methods, the HIV immunogen can also be constructed in whole or in part using standard peptide synthesis. Solid phase synthesis of the peptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis, 2nd ed*., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N, N'-dicylohexylcarbodimide) are well known in the art. Methods of generating a peptide with one or more sulfated tyrosine residues are known to the person of ordinary skill in the art, and described herein (see, e.g., U.S. Pat. No. 5,541,095, 2009/0042738, 2006/0009631, 2003/0170849, 2006/0115859, and Liu et al., Mol. Biosyst., 7:38-47, 2011, each of which is incorporated by reference herein).

In some embodiments, the HIV immunogen includes a canarypox based vector and/or a HIV-1 protein, such as the canarypox based vector (ALVAC-HIV) and the AIDSVAX HIV Clade B and E gp120 proteins formulated in Alum as used in the RV144 Thai trial.[1]

B. Agents that Stimulate the Ras Pathway

Any agent that stimulates the Ras pathway can be included in the compositions disclosed herein, and can be used in the method disclosed herein. These agents include, but are not limited to, polypeptides, nucleic acids, chemical compounds, antibodies, and small molecules. In some embodiments, the activator of the Ras pathway is not Alum or an aluminum salt. The Ras pathway is shown in FIG. 12. Molecules that activate this pathway, by affecting biological molecules used in the pathway, are of use in the methods disclosed herein.

In one embodiment, the activator of the Ras pathway is epidermal growth factor (EGF) or a biological molecule that activates the EGF receptor. Without being bound by theory, the EGF signaling pathway is shown in FIG. 9. In specific, non-limiting examples, EFG has the amino acid sequence set forth as:

```
                                    (Rhesus EGF, SEQ ID NO: 1)
NSD SEC PLSH DGY CLH DGVC MYIEA LDKYA CNCVV GYIGE RCQ YRDL KWW ELR;
or (Human EGF, SEQ ID NO: 2)
NSD SEC PLSH DGY CLH DGVC MYIEA LDKYA CNCVV GYIGE

RCQ YRDL KWW ELR
```

In some embodiments, the composition includes human EGF, such as a polypeptide comprising the amino acid sequence set forth as SEQ ID NO: 2. In another embodiment, the composition includes non-human primate EGF, such as a polypeptide comprising the amino acid sequence set forth as SEQ ID NO: 1. Polypeptides at least 90%, at least 91%, at least 92%, at least 93%, at least 94%, at least 96% at least 97%, at least 98% or at least 99% identical to SEQ ID NO: 1 or SEQ ID NO: 2 are also of use, wherein the polypeptide binds to the EGF receptor and stimulates the EGF pathway. Polypeptides including at most 5, at most 4, at most 3, at most 2, or 1 conservative amino acid substitutions in SEQ ID NO: 1 or SEQ ID NO: 2 are also of use, wherein the polypeptide binds to the EGF receptor and stimulates the EGF pathway Peptides having epidermal growth factor activity include the peptides disclosed in U.S. Published Patent Application No. 20100120696, which is incorporated herein by reference. Peptides that activate the Epidermal Growth Factor receptor are also disclosed in U.S. Published Patent Application No. 20080249008, which is incorporated herein by reference. Additional EGF polypeptides of use are disclosed in U.S. Published Patent Application No. 20130053314, which is incorporated herein by reference. Any of these peptides can be used in the compositions and methods disclosed herein.

In some embodiments, the agent is insulin like growth factor-1 (IGF-1). The human preproprotein can have the amino acid sequence set forth as:

(SEQ ID NO: 3)
MGKISSLPTQ LFKCCFCDFL KVKMHTMSSS HLFYLALCLL

TFTSSATAGP ETLCGAELVD ALQFVCGDRG FYFNKPTGYG

SSSRRAPQTG IVDECCFRSC DLRRLEMYCA PLKPAKSARS

VRAQRHTDMP KTQKYQPPST NKNTKSQRRK GSTFEERK

The mature form of this protein can be used, or synthetic forms of IGF-1.

(SEQ ID NO: 4)
MITPTVKMHT MSSSHLFYLA LCLLTFTSSA TAGPETLCGA

ELVDALQFVC GDRGFYFNKP TGYGSSSRRA PQTGIVDECC

FLSCDLRRLE MYCAPLKPAK SARSVRAQRH TDMPKTQKEV

HLKNASRGSA GNKNYRML (SEQ ID NO: 5)
MITPTVKMHT MSSSHLFYLA LCLLTFTSSA TAGPETLCGA

ELVDALQFVC GDRGFYFNKP TGYGSSSRRA PQTGIVDECC

FRSCDLRRLE MYCAPLKPAK SARSVRAQRH TDMPKTQKEV

HLKNASRGSA GNKNYRM (SEQ ID NO: 6)
MGKISSLPTQ LFKCCFCDFL KVKMHTMSSS HLFYLALCLL

TFTSSATAGP ETLCGAELVD ALQFVCGDRG FYFNKPTGYG

SSSRRAPQTG IVDECCFRSC DLRRLEMYCA PLKPAKSARS

VRAQRHTDMP KTQKYQPPST NKNTKSQRRK GWPKTHPGGE

QKEGTEASLQ IRGKKKEQRR EIGSRNAECR GKKGK (SEQ ID NO: 7)
MGKISSLPTQ LFKCCFCDFL KVKMHTMSSS HLFYLALCLL

TFTSSATAGP ETLCGAELVD ALQFVCGDRG FYFNKPTGYG

SSSRRAPQTG IVDECCFRSC DLRRLEMYCA PLKPAKSARS

VRAQRHTDMP KTQKEVHLKN ASRGSAGNKN YRM (SEQ ID NO: 8)
MITPTVKMHT MSSSHLFYLA LCLLTFTSSA TAGPETLCGA

ELVDALQFVC GDRGFYFNKP TGYGSSSRRA PQTGIVDECC

FLSCDLRRLE MYCAPLKPAK SARSVRAQRH TDMPKTQKEV

HLKNASRGSA GNKNYRMD (SEQ ID NO: 9)
MGKISSLPTQ LFKCCFCDFL KVKMHTMSSS HLFYLALCLL

TFTSSATAGP ETLCGAELVD ALQFVCGDRG FYFNKPTGYG

SSSRRAPQTG IVDECCFRSC DLRRLEMYCA PLKPAKSARS

VRAQRHTDMP KTQKYQPPST NKNTKSQRRK GWPKTHPGGE

QKEGTEASLQ IRGKKKEQRR EIGSRNAECR GKKGKL (SEQ ID NO: 10)
MITPTVKMHT MSSSHLFYLA LCLLTFTSSA TAGPETLCGA

ELVDALQFVC GDRGFYFNKP TGYGSSSRRA PQTGIVDECC

FLSCDLRRLE MYCAPLKPAK SARSVRAQRH TDMPKTQKEV

HLKNASRGSA GNKNYRM

Two additional sequences (SEQ ID NO: 11 and 12) and comparisons of these sequence are shown below:

*Macaca mulatta* Insulin-Like Growth Factor 1

MGKISSLPTQLFKCCFCDFLKVKMHTMSSSHLFYLALCLLTFTS

SATAGPETLCGAELVDALQFVCGDRGFYFNKPTGYGSSSRRAPQTGIVDE

CCFRSCDL

RRLEMYCAPLKPAKSARSVRAQRHTDMPKTQKEVHLKNASRGSAGNKNYR

M

*Homo sapiens* Insulin-Like Growth Factor 1

MGKISSLPTQLFKCCFCDFLKVKMHTMSSSHLFYLALCLLTFTS

SATAGPETLCGAELVDALQFVCGDRGFYFNKPTGYGSSSRRAPQTGIVDE

CCFRSCDL

RRLEMYCAPLKPAKSARSVRAQRHTDMPKTQKEVHLKNASRGSAGNKNYR

M

| Range 1: 32 to 184 Genhept Graphics | | | | | |
|---|---|---|---|---|---|
| Score | Expect | Method | Identities | Positives | Gaps |
| 263 bits (672) | 8e/87 | Composition-based stats. | 153/153(100%) | 153/153(100%) | 0/153 (0%) |

```
Query    1   MGKISSLPTQLFKCCFCDFLKVKMHTMSSSHLFYLALCLLTFTSSATAGPETLCGAELVD    60
             MGKISSLPTQLFKCCFCDFLKVKMHMSSSHLFYLALCLLTFTSSATAGPETLCGAELVD 61   ALQFVCGDRGFYFNKPTGYGSSSRRAPQTGIVDECCFRSCDLRRLEMYCAPLKPAKSARS   120
             ALQFVCGDRGFYFNKPTGYGSSSRRAPQTGIVDECCFRSCDLRRLEMYCAPLKPAKSARS 121   VRAQRHTDMPKTQKEVHLKNASRGSAGNKNYRM                              153
             VRAQRHTDMPK QKEVHLKNASRGSAGNKNYRM
```

V Next Match
A Previous Match

In some embodiments, the composition includes human IGF, such as a polypeptide comprising the amino acid sequence set forth as SEQ ID NO: 3, or the mature form thereof. In another embodiment, the composition includes a synthetic IGF, such as a polypeptide comprising the amino acid sequence set forth as one of SEQ ID NOs: 4-10 Polypeptides at least 90%, at least 91%, at least 92%, at least 93%, at least 94%, at least 96% at least 97%, at least 98% or at least 99% identical to one of SEQ ID NOs: 3-10 are also of use, wherein the polypeptide binds to the IGF receptor and stimulates the IGF pathway. Polypeptides including at most 5, at most 4, at most 3, at most 2, or 1 conservative amino acid substitutions in one of SEQ ID NOs: 3-10 are also of use, wherein the polypeptide binds to the IGF receptor and stimulates the IGF pathway Mecasermin (ICRELEX®) is a synthetic analog of IGF-1. Mecasermin is also of use in the compositions disclosed herein. In addition, an IGF-1/IGF binding peptide (IGBP)-3 complex can also be used, such as mecasermin rinfabate (Insmed). Agents that raise the level of IGF-1, such as MK-677 are also of use.

The agent can be a small molecule. For example, the probe compounds ML099 (CID-888706), ML098 (CID-7345532), and ML097 (CID-2160985) function by increasing the affinity of the GTPases for guanine nucleotides (see Surviladze et al., "Three small molecule pan activator families of Ras-related GTPases, Probe Reports from the NIH Molecular Libraries Program [Internet]. Bethesda (Md.): National Center for Biotechnology Information (US); 2010-2009 May 18 [updated 2010 Sep. 2], incorporated herein by reference). These small molecules are of use in the compositions and methods disclosed herein.

In some embodiments, the agent that stimulates the Ras pathway is (a) epidermal growth factor (EGF) or a functional fragment or variant hereof; (b) insulin like growth factor (IGF) or a functional fragment or variant thereof; or (c) a combination thereof In some examples, the composition can include, for example, about 50 to about 500 µg of IGF-1, such as about 50 to about 250 µg of IGF-1, such as about 50 to about 100 µg of IGF-1 or about 250 to about 500 µg of IGF-1.

The agent can be an extracellular-signal-regulated kinase (ERK) agonist or an AKT agonist, such as an antibody that specifically binds ERK or AKT and stimulates Ras signaling. The agent can upregulate the pathways shown in FIGS. 9-12, MORC3, STAU1, Loc710822, ILF3, HERC3, NAA38, PECR, MAP2K, LOC716474, EWSR, MGAT2, and/or NOSIP. Combinations of agents that activate the Ras pathway can also be used.

C. Polynucleotides and Expression

Polynucleotides encoding the HIV immunogen and/or the agent that stimulates the Ras pathway are also of use in the methods disclosed herein. For example a nucleic acid molecule encoding a HIV-1 envelope protein or immunogenic fragment thereof can be expressed in a cell to make the HIV immunogen. These polynucleotides include DNA, cDNA and RNA sequences which encode the antigen. Nucleic acids encoding these molecules can readily be produced by one of skill in the art, using the amino acid sequences known in the art (such as the HIV-1 envelope protein sequences or EGF sequences) and the genetic code.

Nucleic acid molecules encoding the HIV immunogen and/or the agent that stimulates the Ras pathway can be prepared by any suitable method including, for example, cloning of appropriate sequences or by chemical synthesis. Examples of appropriate cloning and sequencing techniques, and instructions sufficient to direct persons of skill through many cloning exercises are known (see, e.g, Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The nucleic acid molecules can be expressed in a recombinantly engineered cell such as bacteria, plant, yeast, insect and mammalian cells. The HIV immunogen and/or the agent that stimulates the Ras pathway or can be expressed as separate proteins, or as a fusion protein. Those of skill in the art are knowledgeable in the numerous expression systems available for expression of proteins including *E. coli*, other bacterial hosts, yeast, and various higher eukaryotic cells such as the COS, CHO, HeLa and myeloma cell lines.

One or more DNA sequences encoding the HIV immunogen or agent that stimulates the Ras pathway (such as EGf or IGF) can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

The expression of nucleic acids encoding the HIV immunogen and/or the agent that stimulates the Ras pathway can be achieved by operably linking the DNA or cDNA to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes. Vectors can be used, such as plasmid or viral vectors, for example a poxviral vector or an adenoviral vector.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or HIV-1 Env binding fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, HIV immunogen and/or the agent that stimulates the Ras pathway can be purified according to standard procedures in the art, including ammonium sulfate precipitation, affinity columns, column chromatography, and the like (see, generally, Simpson ed., Basic methods in Protein Purification and Analysis: A laboratory Manual, Cold Harbor Press, 2008). The HIV immunogen and/or the agent that stimulates the Ras pathway need not be 100% pure. Once purified, partially or to homogeneity as desired, if to be used therapeutically, the polypeptides should be substantially free of endotoxin.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, and especially as described by Buchner et al., supra.

In addition to recombinant methods, the HIV immunogen and/or the agent that stimulates the Ras pathway can also be constructed in whole or in part using standard peptide synthesis. Solid phase synthesis of the polypeptides can be accomplished by attaching the C-terminal amino acid of the sequence to an insoluble support followed by sequential addition of the remaining amino acids in the sequence. Techniques for protein synthesis are described, for example, by Chan and white (eds), *Fmoc Solid Phase Peptide Synthesis: A Practical Approach*, Oxford University Press, 2000; Howl (ed), *Peptide Synthesis and Applications*, humana Press, 2010; Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Exemplary techniques include the direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. Proteins of various length may be synthesized by condensation of the amino and carboxyl termini of shorter fragments. Methods of forming peptide bonds by activation of a carboxyl terminal end (such as by the use of the coupling reagent N, N'-dicylohexylcarbodimide) are well known in the art.

D. Further Description of Immunogenic Compositions

The disclosed HIV-1 immunogens, agents that stimulate the Ras pathway, and nucleic acids, can be included in a pharmaceutical composition (including therapeutic and prophylactic formulations), often combined together with one or more pharmaceutically acceptable vehicles and, optionally, other therapeutic ingredients (for example, antibiotics or antiviral drugs). In some embodiments, the agent that stimulates the Ras pathway is not alum or aluminum sulfate. In several embodiments, the disclosed HIV-1 immunogens are included in a composition that further includes an agent that stimulates the Ras pathway, such as EGF or IGF-1, or a functional fragments or variants thereof that activate the Ras pathway. In some embodiments the composition includes alum or aluminum sulfate. In additional embodiments, a prime boost strategy can be utilized.

Such pharmaceutical compositions can be administered to subjects by a variety of administration modes known to the person of ordinary skill in the art, for example, intramuscular, subcutaneous, intravenous, intra-arterial, submucosal, intradermal, intra-articular, intraperitoneal, or parenteral routes.

In some embodiments, the immunogenic composition includes a therapeutically effective amount of an HIV immunogen including a canarypox based vector and/or a HIV-1 protein, such as the canarypox based vector (ALVAC-HIV) and/or the AIDSVAX HIV Clade B and E gp120 proteins formulated in Alum as used in the RV144 Thai trial, alum, and/or an agent that stimulates the Ras pathway, such as EGF or IGF.

To formulate the pharmaceutical compositions, the HIV immunogen and/or the agent that stimulates the Ras pathway, or a nucleic acid encoding the HIV immunogen and/or the agent that simulates the Ras pathway, can be combined with various pharmaceutically acceptable additives, as well as a base or vehicle for dispersion of the conjugate. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, TWEEN® 80), solubility enhancing agents (for example, cyclodextrins and derivatives thereof), stabilizers (for example, serum albumin), and reducing agents (for example, glutathione) can be included. Adjuvants, such as aluminum hydroxide (ALHYDROGEL®, available from Brenntag Biosector, Copenhagen, Denmark and AMPHOGEL®, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions.

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The HIV-1 immunogens and/or the agent that stimulates the Ras pathway, such as EGF or IGF-1, or a functional fragments or variants thereof, can be dispersed in a base or vehicle, which can include a hydrophilic compound having a capacity to disperse the HIV immunogens, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films, for examples for direct application to a mucosal surface.

The HIV-1 immunogens and/or the agent that stimulates the Ras pathway, such as EGF, or IGF, a functional fragment or variant of EGF or IGF, can be combined with the base or vehicle according to a variety of methods, and release of the HIV-1 immunogens and/or the agent that stimulates the Ras pathway, such as EGF, IGF, a functional fragment or variant of EGF or IGF, can be by diffusion, disintegration of the vehicle, or associated formation of water channels. In some circumstances, the HIV-1 immunogens and/or the agent that stimulates the Ras pathway are dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The pharmaceutical compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the immunogenic compositions can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the disclosed HIV immunogens can be brought about by including in the composition an agent which delays absorption, for example, monostearate salts and gelatin.

In certain embodiments, the HIV-1 immunogens and/or the agent that stimulates the Ras pathway, such as EGF, IGF-1, or a functional fragment or variant, can be administered in a time-release formulation, for example in a composition that includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the disclosed antigen and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body. Numerous systems for controlled delivery of therapeutic proteins are known (e.g., U.S. Pat. Nos. 5,055,303; 5,188,837; 4,235,871; 4,501,728; 4,837,028; 4,957,735; and 5,019,369; U.S. Pat. Nos. 5,055,303; 5,514,670; 5,413,797; 5,268,164; 5,004,697; 4,902,505; 5,506,206; 5,271,961; 5,254,342; and 5,534,496).

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the conjugate in the required amount in an appropriate solvent with one or a combination of ingredients enumerated herein, as required, followed by filtered sterilization. Generally, dispersions are prepared by incorporating the disclosed antigen and/or other biologically active agent into a sterile vehicle that contains a basic dispersion medium and the required other ingredients from those enumerated herein. In the case of sterile powders, methods of preparation include vacuum drying and freeze-drying which yields a powder of the disclosed antigen plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like. The sterile preparation is then stored in a dosage form in a sterile container, such as a glass or plastic vial (e.g., with a pierceable lid) or syringe, until administration to a subject.

In one specific, non-limiting example, a pharmaceutical composition for intravenous administration would include about 0.1 µg to 10 mg of a HIV-1 immunogens per subject per day. Dosages from 0.1 up to about 100 mg per subject per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remingtons Pharmaceutical Sciences*, 19$^{th}$ Ed., Mack Publishing Company, Easton, Pa., 1995. A unit dosage form contains a suitable single preselected dosage for administration to a subject, or suitable marked or measured multiples of two or more preselected unit dosages, and/or a metering mechanism for administering the unit dose or multiples thereof.

In several embodiments, the compositions include an adjuvant. The person of ordinary skill in the art is familiar with adjuvants, for example, those that can be included in an immunogenic composition. It will be appreciated that the choice of adjuvant can be different in these different applications, and the optimal adjuvant and concentration for each situation can be determined empirically by those of skill in the art. The adjuvant can be alum or an aluminum salt. In other embodiments, the adjuvant is not alum or an aluminum salt.

The pharmaceutical composition typically contains a therapeutically effective amount of one or more of the HIV immunogen and/or the agents that stimulates the Ras pathway, such as EGF, a functional fragment or variant thereof and can be prepared by conventional techniques. Preparation of immunogenic compositions, including those for administration to human subjects, is generally described in Pharmaceutical Biotechnology, Vol. 61 Vaccine Design—the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757. Typically, the amount of antigen in each dose of the immunogenic composition is selected as an amount which induces an immune response without significant, adverse side effects.

The amount of the disclosed HIV-1 immunogens and/or the agent that stimulates the Ras pathway, such as EGF, IGF, a functional fragment or variant, included in an immunogenic composition can vary depending upon the specific agent employed, the route and protocol of administration, and the target population, for example. In some embodiments, for protein therapeutics, typically, each human dose will comprise 1-1000 µg of protein, such as from about 1 µg to about 100 µg, for example, from about 1 µg to about 50 µg, such as about 1 µg, about 2 µg, about 5 µg, about 10 µg, about 15 µg, about 20 µg, about 25 µg, about 30 µg, about 40 µg, or about 50 µg.

III. Methods of Treatment

The HIV-1 immunogen and/or the agent that stimulates the Ras pathway, such as EGF, IGF, or a functional fragment or variant of EGF or IGF, can be used in methods of preventing, inhibiting and treating an HIV-1 infection, as well as methods of inducing an immune response to HIV-1, as described below. In several embodiments, a subject is administered a therapeutically effective amount of a HIV immunogen and a therapeutically effective amount of an agent that stimulated the Ras pathway. The agent that stimulates the Ras pathway can be administered before, during or after, administration of the HIV immunogen. In some embodiments, the agent that stimulates the Ras pathway is not alum or an aluminum salt, such as aluminum sulfate. In additional embodiments, the subject is administered alum and/or an aluminum salt in addition to the agent that stimulates the Ras pathway (that is not alum or an aluminum salt).

In some embodiments, a subject is selected for treatment that has, or is at risk for developing, an HIV infection, for example because of exposure or the possibility of exposure to HIV. Following administration of a therapeutically effective amount of an HIV immunogen and/or immunogenic composition and/or agent that stimulates the Ras pathway, the subject can be monitored for HIV-1 infection, symptoms associated with HIV-1 infection, or both. The subject can have an acquired immune deficiency syndrome (AIDS).

Typical subjects intended for treatment with the therapeutics and methods of the present disclosure include humans, as well as non-human primates and other animals. To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors, such as sexual exposure, that may be associated with the targeted or suspected disease or condition, as well as diagnostic methods, such as various ELISA and other immunoassay methods, which are available and well known in the art to detect and/or characterize HIV infection. These and other routine methods allow the clinician to select patients in need of therapy using the methods and pharmaceutical compositions of the disclosure. In accordance with these methods and principles, a composition can be administered according to the teachings herein, or other conventional methods known to the person of ordinary skill in the art, as an independent prophylaxis or treatment program, or as a follow-up, adjunct or coordinate treatment regimen to other treatments.

The methods can be used to inhibit, treat or prevent HIV infection either in vitro or in vivo. When inhibiting, treating, or preventing infection in vivo, the methods can be used either to avoid infection in an HIV-seronegative subject (e.g., by inducing an immune response that protects against HIV-1 infection), or to treat existing infection in an HIV-seropositive subject. The HIV-seropositive subject may or may not carry a diagnosis of AIDS. Hence in some embodiments the methods involves selecting a subject at risk for contracting HIV infection, or a subject at risk of developing AIDS (such as a subject with HIV infection), and administering a HIV-1 immunogen and/or immunogenic composition and/or agent that stimulates the Ras pathway to the subject.

Treatment of HIV by inhibiting HIV replication or infection can include delaying the development of HIV in a subject. Treatment of a HIV also includes reducing signs or symptoms associated with the presence of HIV (for example by reducing or inhibiting HIV replication). In some examples, treatment using the methods disclosed herein prolongs the time of survival of the subject.

The administration of an HIV immunogen and/the agent that stimulates the Ras pathway can be for either prophylactic or therapeutic purpose. When provided prophylactically, the disclosed therapeutic compositions are provided in advance of any symptom, for example in advance of infection. The prophylactic administration of the disclosed therapeutic compositions serves to prevent or ameliorate any subsequent infection. When provided therapeutically, the disclosed therapeutic compositions are provided at or after the onset of a symptom of disease or infection, for example after development of a symptom of HIV-1 infection, or after diagnosis of HIV-1 infection. The therapeutic compositions can thus be provided prior to the anticipated exposure to HIV virus so as to attenuate the anticipated severity, duration or extent of an infection and/or associated disease symptoms, after exposure or suspected exposure to the virus, or after the actual initiation of an infection.

In some embodiments, the method of treating or inhibiting HIV infection includes administering to a subject an immunogenic composition including a therapeutically effective amount of an HIV immunogen including a canarypox based vector and/or a HIV-1 protein, such as the canarypox based vector (ALVAC-HIV) and/or the AIDSVAX HIV Clade B and E gp120 proteins formulated in Alum as used in the RV144 Thai trial, alum, and/or an agent that stimulates the Ras pathway, such as EGF or IGF. The immunogenic composition can be administered one or more than one (such as in a prime-boost regime) as needed to provide the subject with a therapeutically effective amount of the immunogenic composition and to elicit a neutralizing immune response to HIV-1 in the subject.

For prophylactic and therapeutic purposes, an HIV immunogen and agent that stimulates the Ras pathway can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The HIV immunogen and the agent that stimulates the Ras pathway can be administered simultaneously or sequentially. The therapeutically effective dosage of the HIV immunogen and the agent that stimulates the Ras pathway can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the composition (for example, amounts that are effective to elicit a desired immune response or alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes.

HIV infection does not need to be completely eliminated or inhibited for the methods to be effective. For example, treatment with an HIV immunogen and/or the agent that stimulates the Ras pathway, such as EGF, a functional fragment or variant thereof, can decrease HIV infection by a desired amount, for example by at least 10%, at least 20%, at least 50%, at least 60%, at least 70%, at least 80%, at least 90%, at least 95%, at least 98%, or even at least 100% (elimination of detectable HIV infected cells), as compared to HIV infection in the absence of the composition. In additional examples, HIV replication can be reduced or inhibited by the disclosed methods. HIV replication does not need to be completely eliminated for the method to be effective. For example, treatment with the HIV immunogen and/or the agent that stimulates the Ras pathway, such as EGF, a functional fragment or variant thereof, can decrease HIV replication by a desired amount, for example by at least 10%, at least 20%, at least 50%, at least 60%, at least 70%, at least 80%, at least 90%, at least 95%, at least 98%, or even at least 100% (elimination of detectable HIV replication), as compared to HIV replication in the absence of the composition.

To successfully reproduce itself, HIV must convert its RNA genome to DNA, which is then imported into the host cell's nucleus and inserted into the host genome through the action of HIV integrase. Because HIV's primary cellular target, CD4+ T-Cells, can function as the memory cells of the immune system, integrated HIV can remain dormant for the duration of these cells' lifetime. Memory T-Cells may survive for many years and possibly for decades. This latent HIV reservoir can be measured by co-culturing CD4+ T-Cells from infected patients with CD4+ T-Cells from uninfected donors and measuring HIV protein or RNA (See, e.g., Archin et al., *AIDS*, 22:1131-1135, 2008). In some embodiments, the provided methods of treating or inhibiting HIV infection include reduction or elimination of the latent reservoir of HIV infected cells in a subject. For example, a reduction of at least 10%, at least 20%, at least 50%, at least 60%, at least 70%, at least 80%, at least 90%, at least 95%, at least 98%, or even at least 100% (elimination of detectable HIV) of the latent reservoir of HIV infected cells in a subject, as compared to the latent reservoir of HIV infected cells in a subject in the absence of the treatment.

Studies have shown that the rate of HIV transmission from mother to infant is reduced significantly when zidovudine is administered to HIV-infected women during pregnancy and delivery and to the offspring after birth (Connor et al., 1994 *Pediatr Infect Dis J* 14: 536-541). Several studies of mother-to-infant transmission of HIV have demonstrated a correlation between the maternal virus load at delivery and risk of HIV transmission to the child. The present disclosure provides methods that are of use in decreasing HIV-transmission from mother to infant. Thus, in some embodiments a therapeutically effective amount of an HIV-1 immunogen and/or the agent that stimulates the Ras pathway, such as EGF, IGF, a functional fragment or variant, is administered in order to prevent transmission of HIV, or decrease the risk of transmission of HIV, from a mother to an infant. In some embodiments, a therapeutically effective amount of HIV-1 immunogen and/or the agent that stimulates the Ras pathway, such as EGF, IGF, a functional fragment or variant, is administered to a pregnant subject to induce an immune response that generates neutralizing antibodies that are passes to the fetus via the umbilical cord to protect the fetus from infection during birth. In some embodiments, a therapeutically effective amount of an HIV-1 immunogen and/or the agent that stimulates the Ras pathway, such as EGF, IGF, or a functional fragment or variant, is administered to mother and/or to the child at childbirth. In other examples, a therapeutically effective amount of an HIV-1 immunogen and/or the agent that stimulates the Ras pathway, such as EGF, IGF, or a functional fragment or variant, is administered to the mother and/or infant prior to breast feeding in order to prevent viral transmission to the infant or decrease the risk of viral transmission to the infant.

A therapeutically effective amount of an HIV-1 immunogen and/or the agent that stimulates the Ras pathway, such as EGF, IGF, a functional fragment or variant, can be administered to a subject. A therapeutically effective amount of such agents will depend upon the severity of the disease and/or infection and the general state of the patient's health. For example, a therapeutically effective amount of HIV-1 immunogen and/or the agent that stimulates the Ras pathway, such as EGF, IGF, or a functional fragment or variant, is that which provides either subjective relief of a symptom(s) or an objectively identifiable improvement as noted by the clinician or other qualified observer.

The therapeutically effective amount of an HIV-1 immunogen and/or the agent that stimulates the Ras pathway, such as EGF, IGF, a functional fragment or variant, will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response. As described above in the forgoing listing of terms, an effective amount is also one in which any toxic or detrimental side effects of the disclosed antigen and/or other biologically active agent is outweighed in clinical terms by therapeutically beneficial effects. A non-limiting range for a therapeutically effective amount of the disclosed HIV-1 immunogen within the methods and compositions of the disclosure is about 0.01 mg/kg body weight to about 10 mg/kg body weight, such as about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 4 mg/kg, about 5 mg/kg, or about 10 mg/kg, for example 0.01 mg/kg to about 1 mg/kg body weight, about 0.05 mg/kg to about 5 mg/kg body weight, about 0.2 mg/kg to about 2 mg/kg body weight, or about 1.0 mg/kg to about 10 mg/kg body weight. A non-limiting range for a therapeutically effective amount of IGF-1 is about 0.025 mg/kg to about 0.2 mg/kg, such as about 0.05 to about 0.15 mg/kg, for example about 0.10 to about 0.012 mg/kg or about 0.06 to about 0.01 mg/kg.

In one specific, non-limiting example, a composition for intravenous administration would include about 0.1 µg to 10 mg of a disclosed HIV immunogen per subject per day and 0.1 µg to 10 mg the agent that stimulates the Ras pathway. In some specific non-liming examples, the agent that stimulates the Ras pathway is IGF-1, and the about 50 to about 500 µg of IGF-1, such as about 50 to about 250 µg of IGF-1, such as about 50 to about 100 µg of IGF-1 or about 250 to about 500 µg of IGF-1.

Actual methods for preparing administrable compositions will be known or apparent to those skilled in the art and are described in more detail in such publications as *Remingtons Pharmaceutical Sciences*, 19$^{th}$ Ed., Mack Publishing Company, Easton, Pa., 1995.

Dosage can be varied by the attending clinician to maintain a desired concentration at a target site (for example, systemic circulation). Higher or lower concentrations can be selected based on the mode of delivery, for example, transepidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth. To achieve the same serum concentration level, for example, slow-release particles with a release rate of 5 nanomolar (under standard conditions) would be administered at about twice the dosage of particles with a release rate of 10 nanomolar.

In several embodiments, it may be advantageous to administer the therapeutic agents disclosed herein with other agents such as proteins, peptides, antibodies, and other antiviral agents, such as anti-HIV agents. Examples of such anti-HIV therapeutic agents include nucleoside reverse transcriptase inhibitors, such as abacavir, AZT, didanosine, emtricitabine, lamivudine, stavudine, tenofovir, zalcitabine, zidovudine, and the like, non-nucleoside reverse transcriptase inhibitors, such as delavirdine, efavirenz, nevirapine, protease inhibitors such as amprenavir, atazanavir, indinavir, lopinavir, nelfinavir, osamprenavir, ritonavir, saquinavir, tipranavir, and the like, and fusion protein inhibitors such as enfuvirtide and the like. In some examples, the disclosed therapeutic agents are administered with T-helper cells, such as exogenous T-helper cells. Exemplary methods for producing and administering T-helper cells can be found in International Patent Publication WO 03/020904, which is incorporated herein by reference.

For any application, treatment with an HIV-1 immunogen and/or the agent that stimulates the Ras pathway, such as EGF, IGF, a functional fragment or variant, can be combined with anti-retroviral therapy, such as HAART. Antiretroviral drugs are broadly classified by the phase of the retrovirus life-cycle that the drug inhibits. The therapeutic agents can be administered before, during, concurrent to and/or after retroviral therapy. In some embodiments, the therapeutic agents are administered following a course of retroviral therapy. The disclosed therapeutic agents can be administered in conjunction with nucleoside and nucleotide reverse transcriptase inhibitors (nRTI), non-nucleoside reverse transcriptase inhibitors (NNRTI), protease inhibitors, Entry inhibitors (or fusion inhibitors), Maturation inhibitors, or a broad spectrum inhibitors, such as natural antivirals. Exemplary agents include lopinavir, ritonavir, zidovudine, lamivudine, tenofovir, emtricitabine and efavirenz.

In some embodiments, an HIV-1 immunogen and/or the agent that stimulates the Ras pathway, such as EGF, IGF, a functional fragment or variant, is used to prime or induce an immune response (such as a T or B cell response) to HIV-1 in a subject. Such methods include administering to a subject a therapeutically effective amount of an HIV-1 immunogen and/or the agent that stimulates the Ras pathway, such as EGF, IGF, a functional fragment or variant, to prime or enhance an immune response, for example, an immune response to an HIV envelope protein, such as gp160, gp140, gp120 or gp41.

In several embodiments, administration of the therapeutically effective amount of an HIV-1 immunogen and/or the agent that stimulates the Ras pathway, such as EGF, IGF, a functional fragment or variant, induces a T cell response. In some such embodiments, the T cell response is a CD4$^+$ T helper cell response, such as a Th1 cell response.

In some embodiments, an HIV immunogen an agent that stimulates the Ras pathway is administered to the subject simultaneously with the administration of another adjuvant, such as alum or aluminum sulfate. In other embodiments, agent that stimulates the Ras pathway is administered to the subject after the administration of the HIV immunogen, optionally with another adjuvant such as alum or aluminum sulfate, and within a sufficient amount of time to induce the immune response.

In certain embodiments, novel combinatorial and coordinate immunization protocols employ separate immunogens or formulations, each directed toward eliciting an anti-HIV immune response, such as an immune response to HIV-1 gp120 protein, along with an agent that stimulates the Ras pathway. Separate immunogenic compositions that elicit the anti-HIV immune response can be combined in a polyvalent immunogenic composition administered to a subject in a single immunization step, or they can be administered separately (in monovalent immunogenic compositions) in a coordinate immunization protocol.

In some embodiments, a suitable immunization regimen includes at least two separate inoculations with an HIV immunogen and the agent that stimulates the Ras pathway, with a second inoculation being administered more than about two, about three to eight, or about four, weeks following the first inoculation. A third inoculation can be administered several months after the second inoculation, and in specific embodiments, more than about five months after the first inoculation, more than about six months to about two years after the first inoculation, or about eight months to about one year after the first inoculation. Periodic inoculations beyond the third are also desirable to enhance the subject's "immune memory." The adequacy of the vaccination parameters chosen, e.g., formulation, dose, regimen and the like, can be determined by taking aliquots of serum from the subject and assaying antibody titers during the course of the immunization program. Alternatively, the T cell populations can be monitored by conventional methods. In addition, the clinical condition of the subject can be monitored for the desired effect, e.g., prevention of HIV-1 infection or progression to AIDS, improvement in disease state (e.g., reduction in viral load), or reduction in transmission frequency to an uninfected partner. If such monitoring indicates that vaccination is sub-optimal, the subject can be boosted with an additional dose of immunogenic composition, and the vaccination parameters can be modified in a fashion expected to potentiate the immune response. Thus, for example, the dose of an HIV immunogen and agent that stimulates the Ras pathway can be increased or the route of administration can be changed.

It is contemplated that there can be several boosts, and that each boost can include a different HIV-1 immunogen and/or agent that stimulates the Ras pathway. It is also contemplated in some examples that the boost may be the same HIV-1 immunogen and/or agent that stimulates the Ras pathway as another boost, or the prime.

The prime can be administered as a single dose or multiple doses, for example two doses, three doses, four doses, five doses, six doses or more can be administered to a subject over days, weeks or months. The boost can be administered as a single dose or multiple doses, for example two to six doses, or more can be administered to a subject over a day, a week or months. Multiple boosts can also be given, such one to five, or more. Different dosages can be used in a series of sequential inoculations. For example a relatively large dose in a primary inoculation and then a boost with relatively smaller doses. The immune response against the selected antigenic surface can be generated by one or more inoculations of a subject.

For each particular subject, specific dosage regimens can be evaluated and adjusted over time according to the individual need and professional judgment of the person administering or supervising the administration of the immunogenic composition. In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of the therapeutic agent administered to the individual can be at least partially based on the antibody titer level. The antibody titer level can be based on, for example, an immunobinding assay which measures the concentration of antibodies in the serum which bind to an antigen including the HIV immunogen, for example, a HIV-1 gp120 protein. The methods of using immunogenic composition, and the related compositions and methods of the disclosure are useful in increasing resistance to, preventing, ameliorating, and/or treating infection and disease caused by HIV (such as HIV-1) in animal hosts, and other, in vitro applications.

Nucleic acids can be administered. One approach to administration of nucleic acids is direct immunization with plasmid DNA, such as with a mammalian expression plasmid. As described above, the nucleotide sequence encoding a HIV immunogen, and/or an activator of the Ras pathway, can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and QUIL A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 µg encapsulated in ISCOMS™ have been found to produce Class I mediated CTL responses (Takahashi et al., *Nature* 344:873, 1990).

In another approach to using nucleic acids for immunization, a disclosed HIV immunogen, and/or agent that stimulates the Ras pathway can also be expressed by attenuated viral hosts or vectors or bacterial vectors. Recombinant vaccinia virus, adeno-associated virus (AAV), herpes virus, retrovirus, poxvirus or other viral vectors can be used to express the peptide or protein, thereby eliciting a CTL response. For example, vaccinia vectors and methods useful in immunization protocols are described in U.S. Pat. No. 4,722,848. BCG (*Bacillus* Calmette Guerin) provides another vector for expression of the peptides (see Stover, *Nature* 351:456-460, 1991).

In one embodiment, a nucleic acid encoding a disclosed antigen is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 µg/kg to about 50 mg/kg, and typically are about 0.005 mg/kg to about 5 mg/kg (see, e.g., U.S. Pat. No. 5,589,466).

IV. Methods of Detecting Likelihood of a Protective Immune Response

Methods are provided herein for determining the likelihood that an immunogenic composition will induce a protective immune response in a subject. In some embodiments, the immune response can include antibody-dependent cell-mediated cytotoxic (ADCC) activity, Fc receptor ligation of HIV-specific antibodies in the mucosa, and/or an increase in antibody production. Methods are also provided for determining if an agent will be effective for preventing and/or treating an HIV infection in a subject.

In some embodiments, the subject has, or is at risk for developing, an HIV infection, for example because of exposure or the possibility of exposure to HIV. Following administration of a therapeutically effective amount of an HIV immunogen and/or immunogenic composition and/or agent that stimulates the Ras pathway, the subject can be monitored. The subject can have an acquired immune deficiency syndrome (AIDS).

In some embodiments, the methods include detecting a level of Extracellular signal Related Kinase (ERK) and/or Protein kinase b (AKT) in a biological sample from the subject administered the immunogenic composition; and comparing the level of ERK and/or AKT to a respective control level of ERK and AKT. In some embodiments, the detection of an increase in the level of ERK and/or AKT as compared to the respective control indicates the composition will induce a protective immune response against the HIV in the subject. In other embodiments, a detection of an increase in the level of ERK and AKT as compared to the respective control level indicates that the agent will be effective for preventing and/or treating an HIV infection in a subject. The control can be a standard value of ERK and AKT, respectively in one or more subjects known not to have an HIV infection. The control can be the level of ERK and/or AKT, respectively in the subject prior to administration of the immunogenic composition.

The method also can induced detecting a level of one or more components of the Ras pathway. In some embodiments, an increase in the level of the one or more components of the Ras pathway as compared to a control level indicates that the immunogenic composition will produce a protective immune response. In other embodiments, a detection of an increase in the level of one or more of the components of the Ras pathway, as compared to a control level, indicates that the agent will be effective for preventing and/or treating an HIV infection in a subject. The control can be a standard value of the one or more components of the Ras pathway, in one or more subjects known not to have an HIV infection. The control can be the level of the components of the Ras pathway, in the subject prior to administration of the immunogenic composition.

In some embodiments, the methods include detecting an alteration of expression of one of more of MORC family CW-type zinc finger 3 (MORC3), staufen, RNA binding protein, homolog 1 (STAU1), 26S protease regulatory subunit S10B-like (Loc710822), interleukin enhancer binding factor 3, 90 kDa (ILF3), HECT and RLD domain containing E3 ubiquitin protein ligase 3 (HERC3), N(alpha)-acetyltransferase 38, NatC auxiliary subunit (NAA38), peroxisomal trans-2-enoyl-CoA reductase (PECR), mitogen-activated protein kinase kinase 1 (MAP2K), nucleoporin NDC1-like (LOC71674), Ewing sarcoma breakpoint region 1 (EWSR1), nitric oxide synthase-interacting protein (NOSIP) and/or alpha-1,6-mannosyl-glycoprotein 2-beta-N-acetylglucosaminyltransferase-like (MGAT2). The amino acid and nucleic acid sequences for these markers are set forth in the GENBANK® Accession entries provided in Table A below. In some embodiments, the methods disclosed herein can include evaluating the level of one or more of the following:

TABLE A

Markers

| Marker | Amino Acid | Nucleic Acid |
|---|---|---|
| MORC3 | XP_001084530 (RM), | XM_001084530 (RM) |
|  | XP_002803187 (RM) | XM_002803141 (RM) |
|  | XP_002803186 (RM) | XM_002803140 (RM) |
|  | NP_056173 (HS) | NM_015358 (HS) |
| STAU1 | NP_00125323 (RM) | NM_001266308 (RM) |
|  | NP_059347 (HS) | NM_017453 (HS) |
| Loc710822 | XP_001099493 (RM) | XM_001099493 (RM) |
|  | NP_002797 (HS) | NM_002806 (HS) |
| ILF3 | XP_002801113 (RM) | XM_002801067 (RM) |
|  | XP_001102411 (RM) | XM_001102411 (RM) |
|  | XP_002801112 (RM) | XM_002801066 (RM) |
|  | NP_036350 (HS) | NM_012218 (HS) |
|  | NP_703194 (HS) | NM_153464 (HS) |
|  | NP_001131145 (HS) | NM_001137673 (HS) |
| HERC3 | NP_001248295 (RM) | NM_001261366 (RM) |
|  | NP_055421 (HS) | NM_014606 (HS) |
| NAA38 | XP_001087356 (RM) | XM_001087356 (RM) |
|  | NP_115732 (HS) | NM_032356 (HS) |
| PECR | XP_001085907 (RM) | XM_001085907 (RM) |
|  | NP_060911 (HS) | NM_018441 (HS) |
| MAP2K1 | NP_001244478 (RM) | NM_001257549 (RM) |
|  | NP_002746 (HS) | NM_002755 (HS) |
| LOC716474 | XP_001107227 (RM) | XM_001107227 (RM) |
|  | NP_001162023 (HS) | NM_001168551 (HS) |
| EWSR1 | NP_001253170 (RM) | NM_001266241 (RM) |
|  | NP_053733 (HS) | NM_013986 (HS) |
| MGAT2 | NP_002399 (HS) | XR_010703 (RM) |
|  |  | NM_002408 (HS) |
| NOSIP | NP_001181608 (RM) | NM_001194679 (RM) |
|  | NP_057037 (HS) | NM_015953 (HS) |

All GENBANK Accession numbers are incorporated by reference herein as available on Jan. 5, 2015. All GENBANK Accession numbers are incorporated by reference herein as available on Jan. 5, 2015.

The marker can include a polypeptide or nucleic acid sequence at least 95%, 96%, 97%, 98% or 99% identical to the polypeptide or nucleic acid sequence shown in these GENBANK® entries (Table A), respectively, or can be 100% identical to the listed sequence.

The methods can include assessing expression of 1, 2, 3, 4, 5, 6, 7, 8, 9, 10, 11 or all 12 of the markers shown in Table A. The methods can include assessing expression of 1, 2, 3, 4, 5, 6, 7, 8, 9, 10, or 11 of the markers listed in Table A in any combination.

The methods include detecting a level of one or more of MORC3, STAU1, Loc710822, ILF3, HERC3, NAA38, PECR, MAP2K, LOC716474, EWSR, MGAT2 and/or NOSIP in a biological sample from the subject administered the immunogenic composition; and comparing the level of MORC3, STAU1, Loc710822, ILF3, HERC3, NAA38, PECR, MAP2K, LOC716474, EWSR, MGAT2 and/or NOSIP to a respective control level of MORC3, STAU1, Loc710822, ILF3, HERC3, NAA38, PECR, MAP2K, LOC716474, EWSR, MGAT2 and/or NOSIP.

In some embodiments, the detection of an increase in the level of MORC3, STAU1, Loc710822, ILF3, HERC3, NAA38, PECR, MAP2K, LOC716474, EWSR and/or MGAT2, as compared to the respective control indicates the composition will induce a protective immune response against the HIV in the subject. In other embodiments, the detection of a decrease in NOSIP as compared to the respective control level indicates the composition will induce a protective immune response.

In further embodiments, detection of an increase in the level of MORC3, STAU1, Loc710822, ILF3, HERC3, NAA38, PECR, MAP2K, LOC716474, EWSR, and/or MGAT2 as compared to the respective control level indicates that the agent will be effective for preventing and/or treating an HIV infection in a subject. In other embodiments, the detection of a decrease in NOSIP as compared to the respective control level indicates the composition will be effective for preventing and/or treating an HIV infection in the subject.

In additional embodiments, the methods include detecting a level of all of MORC3, STAU1, Loc710822, ILF3, HERC3, NAA38, PECR, MAP2K, LOC716474, EWSR, MGAT2 and NOSIP in a biological sample from the subject administered the immunogenic composition; and comparing the level of MORC3, STAU1, Loc710822, ILF3, HERC3, NAA38, PECR, MAP2K, LOC716474, EWSR, MGAT2 and NOSIP to a respective control level of MORC3, STAU1, Loc710822, ILF3, HERC3, NAA38, PECR, MAP2K, LOC716474, EWSR, MGAT2 and NOSIP. In some embodiments, the detection of an increase in the level of MORC3, STAU1, Loc710822, ILF3, HERC3, NAA38, PECR, MAP2K, LOC716474, EWSR and MGAT2 as compared to the respective control indicates the composition will induce a protective immune response against the HIV in the subject. The detection of a decrease in NOSIP as compared to the respective control level indicates the composition will induce a protective immune response. In other embodiments, detection of an increase in the level of MORC3, STAU1, Loc710822, ILF3, HERC3, NAA38, PECR, MAP2K, LOC716474, EWSR, MGAT2 and NOSIP as compared to the respective control level indicates that the agent will be effective for preventing and/or treating an HIV infection in a subject. The detection of a decrease in NOSIP as compared to the respective control level indicates the composition will be effective for preventing and/or treating an HIV infection in the subject.

The control can be a standard value of MORC3, STAU1, Loc710822, ILF3, HERC3, NAA38, PECR, MAP2K, LOC716474, EWSR, MGAT2 and/or NOSIP, respectively. The control can be the level of MORC3, STAU1, Loc710822, ILF3, HERC3, NAA38, PECR, MAP2K, LOC716474, EWSR, MGAT2 and/or NOSIP, respectively, in the subject prior to administration of the immunogenic composition. The control can be a standard value of MORC3, STAU1, Loc710822, ILF3, HERC3, NAA38, PECR, MAP2K, LOC716474, EWSR, MGAT2 and/or NOSIP, respectively in a subject without a protective immune response. The control can be the level of MORC3, STAU1, Loc710822, ILF3, HERC3, NAA38, PECR, MAP2K, LOC716474, EWSR, MGAT2 and/or NOSIP in one or more subjects known not to have an HIV infection.

In additional example, the methods include detecting a level of ILF3, MAP2 and MGAT2 in a biological sample from the subject administered the immunogenic composition; and comparing the level of ILF3, MAP2 and MGAT2 to a respective control level of ILF3, MAP2 and MGAT2 as compared to the respective control indicates the composition will induce a protective immune response against the HIV in the subject. In other embodiments, detection of an increase in the level of ILF3, MAP2 and MGAT2 as compared to the respective control level indicates that the agent will be effective for preventing and/or treating an HIV infection in a subject.

The control can be a standard value of ILF3, MAP2 and MGAT2, respectively in one or more subjects known not to have an HIV infection. The control can be the level of ILF3, MAP2 and MGAT2, respectively in the subject prior to administration of the immunogenic composition.

Any of the methods disclosed herein also can induced detecting a level of other components of the Ras pathway. An increase in the level of the components as compared to a control level indicates that the immunogenic composition will produce a protective immune response. In additional embodiments, biological markers, such one or more molecules shown in FIGS. 9-12 can also be assessed.

In some embodiments, the sample is any sample of interest that includes white blood cells. The sample can be a blood sample, or purified blood cells. The sample can be a biopsy sample.

The method can also include assessing the clinical factors for the subject. Exemplary factors are CD4 cell count, viremia, or antibody production. Clinical factors also include white blood cell count and weight.

In some embodiments, the immunogenic composition comprises an HIV immunogen and an agent that stimulates the Ras pathway. The agent that stimulates the Ras pathway can be epidermal growth factor, or a functional fragment or variant thereof that binds the EGF receptor and stimulates the Ras pathway. The agent that stimulates the Ras pathway can be insulin-like growth factor, or a functional fragment or variant thereof that binds the IGF receptor and stimulates the Ras pathway. Combinations of agents that activate the Ras pathway can also be used. The HIV immunogen is ag120, gp41 or gp160, or an immunogenic fragment thereof. The immunogenic fragment comprises the V1V2 domain of gp120. In additional embodiments, the immunogenic composition comprises alum and/or an aluminum salt.

A. Methods for Detection of Proteins

In some examples, the level of one or more proteins is analyzed by detecting and quantifying the protein in a biological sample. In particular examples, one or more proteins of the Ras pathway are analyzed, such as AKT and/or ERK. In additional examples, MORC3, STAU1, Loc710822, ILF3, HERC3, NAA38, PECR, MAP2K, LOC716474, EWSR, MGAT2 and/or NOSIP proteins are analyzed.

Suitable biological samples include samples containing protein, such as blood, serum, plasma, for example peripheral blood mononuclear cells, B cells, T cells and/or monocytes, and tissue samples, such as biopsy samples. In some embodiments, the sample includes white blood cells.

In some embodiments, detecting an alteration in the amount of one or more of one or more components of the Ras pathway, such as AKT and/or ERK indicates if an immunogenic composition is effective for inducing a protective immune response to HIV. In other embodiments, detecting an alteration in the amount of MORC3, STAU1, Loc710822, ILF3, HERC3, NAA38, PECR, MAP2K, LOC716474, EWSR, MGAT2 and/or NOSIP indicates if an immunogenic composition is effective for inducing a protective immune response to HIV. In other embodiments, the methods determine that the agent will be effective for preventing and/or treating an HIV infection in a subject.

The expression of protein can be the level of protein in a biological sample. Expression includes, but is not limited to, the production of the protein by translation of an mRNA and the half-life of the protein.

Any standard immunoassay format (such as ELISA, Western blot, or RIA assay) can be used to measure protein levels. Immunohistochemical techniques can be utilized. General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998), and Harlow & Lane, Antibodies, *A Laboratory Manual*, Cold Spring Harbor Publications, New York (1988); these references disclose a number of immunoassay formats and conditions that can be used to determine specific immunoreactivity. Generally, immunoassays include the use of one or more specific binding agents (such as antibodies) that specifically recognizes and can bind a molecule of interest, such as ERK and/or AKT. Such binding agents can include a detectable label (such as a radiolabel, fluorophore or enzyme), that permits detection of the binding to the protein and determination of relative or absolute quantities of the molecule of interest in the sample. Although the details of the immunoassays may vary with the particular format employed, the method of detecting the protein in a sample generally includes the steps of contacting the sample with an antibody, which specifically binds to the protein under immunologically reactive conditions to form an immune complex between the antibody and the protein, and detecting the presence of and/or quantity of the immune complex (bound antibody), either directly or indirectly. The antibody can be a polyclonal or monoclonal antibody, or fragment thereof. In some examples, the antibody is a humanized antibody. In additional examples, the antibody is a chimeric antibody.

The antibodies can be labeled. Suitable detectable markers are described and known to the skilled artisan. For example, various enzymes, prosthetic groups, fluorescent materials, luminescent materials, magnetic agents, and radioactive materials can be used. Non-limiting examples of suitable enzymes include horseradish peroxidase, alkaline phosphatase, beta-galactosidase, or acetylcholinesterase. Non-limiting examples of suitable prosthetic group complexes include streptavidin/biotinm and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary magnetic agent is gadolinium; and non-limiting exemplary radioactive labels include $^{125}I$, $^{131}I$, $^{35}S$ or $^{3}H$. Additional examples are disclosed above.

In another embodiment, the antibody that binds the protein of interest (the first antibody) is unlabeled and a second antibody or other molecule that can bind the antibody that binds the protein of interest is utilized. As is well known to one of skill in the art, a second antibody is chosen that is able to specifically bind the specific species and class of the first antibody. For example, if the first antibody is a mouse IgG, then the secondary antibody may be a goat anti-mouse-IgG. Other molecules that can bind to antibodies include, without limitation, Protein A and Protein G, both of which are available commercially.

Quantitation of proteins can be achieved by immunoassay. The amount of proteins can be assessed and optionally in a control sample. The amounts of protein in the sample from the subject of interest can be compared to levels of the protein found in samples form control subjects or to another control (such as a standard value or reference value). A significant increase or decrease in the amount can be evaluated using statistical methods known in the art.

In some non-limiting examples, a sandwich ELISA can be used to detect the presence or determine the amount of a protein in a sample. In this method, a solid surface is first coated with an antibody that specifically binds the protein of interest. The test sample containing the protein (such as, but not limited to, a blood, plasma, serum, or urine sample), is then added and the antigen is allowed to react with the bound antibody. Any unbound antigen is washed away. A known amount of enzyme-labeled protein-specific antibody is then allowed to react with the bound protein. Any excess unbound enzyme-linked antibody is washed away after the reaction. The substrate for the enzyme used in the assay is then added and the reaction between the substrate and the enzyme produces a color change. The amount of visual color change is a direct measurement of specific enzyme-conjugated bound antibody, and consequently the quantity of the protein present in the sample tested.

In an alternative example, a protein can be assayed in a biological sample by a competition immunoassay utilizing protein standards labeled with a detectable substance and an unlabeled antibody that specifically binds the protein of interest. In this assay, the biological sample (such as, but not limited to, a blood, plasma, serum, or urine sample), the labeled protein standards and the antibody that specifically binds the protein of interest are combined and the amount of labeled protein standard bound to the unlabeled antibody is determined. The amount of protein in the biological sample is inversely proportional to the amount of labeled protein standard bound to the antibody that specifically binds the protein of interest.

Mass spectrometry is particularly suited to the identification of proteins from biological samples, such a components of the Ras pathway, such as AKT, ERK, MORC3, STAU1, Loc710822, ILF3, HERC3, NAA38, PECR, MAP2K, LOC716474, EWSR, MGAT2 and/or NOSIP. Mass spectrometry also is particularly useful in the quantitation of peptides in a biological sample, for example using isotopically labeled peptide standards. The application of mass spectrometric techniques to identify proteins in biological samples is known in the art and is described, for example, in Akhilesh et al., *Nature,* 405:837-846, 2000; Dutt et al., *Curr. Opin. Biotechnol.,* 11:176-179, 2000; Gygi et al., *Curr. Opin. Chem. Biol.,* 4 (5): 489-94, 2000; Gygi et al., *Anal. Chem.,* 72 (6): 1112-8, 2000; and Anderson et al., *Curr. Opin. Biotechnol.,* 11:408-412, 2000.

Separation of ions according to their m/z ratio can be accomplished with any type of mass analyzer, including quadrupole mass analyzers (Q), time-of-flight (TOF) mass analyzers (for example, linear or reflecting) analyzers, magnetic sector mass analyzers, 3D and linear ion traps (IT), Fourier-transform ion cyclotron resonance (FT-ICR) analyzers, Orbitrap analyzers (like LTQ-Orbitrap LC/MS/MS), and combinations thereof (for example, a quadrupole-time-of-flight analyzer, or Q-TOF analyzer). A triple quadropole instrument can be used such as the Q-trap.

In some embodiments, the mass spectrometric technique is tandem mass spectrometry (MS/MS). Typically, in tandem mass spectrometry a protein gene product, such as components of the Ras signaling pathway (for example ERK, AKT, MORC3, STAU1, Loc710822, ILF3, HERC3, NAA38, PECR, MAP2K, LOC716474, EWSR, MGAT2 and/or NOSIP) entering the tandem mass spectrometer is selected and subjected to collision induced dissociation (CID). The spectrum of the resulting fragment ion is recorded in the second stage of the mass spectrometry, as a so-called CID or ETD spectrum. Because the CID or ETD process usually causes fragmentation at peptide bonds and different amino acids for the most part yield peaks of different masses, a CID or ETD spectrum alone often provides enough information to determine the presence of the components of the Ras signaling pathway. Suitable mass spectrometer systems for MS/MS include an ion fragmentor and one, two, or more mass spectrometers, such as those described above. Examples of suitable ion fragmentors include, but are not limited to, collision cells (in which ions are fragmented by causing them to collide with neutral gas molecules), photo dissociation cells (in which ions are fragmented by irradiating them with a beam of photons), and surface dissociation fragmentor (in which ions are fragmented by colliding them with a solid or a liquid surface). Suitable mass spectrometer systems can also include ion reflectors.

Prior to mass spectrometry, the sample can be subjected to one or more dimensions of chromatographic separation, for example, one or more dimensions of liquid or size exclusion chromatography. Representative examples of chromatographic separation include paper chromatography, thin layer chromatography (TLC), liquid chromatography, column chromatography, high performance liquid chromatography (HPLC), fast protein liquid chromatography (FPLC), ion exchange chromatography, size exclusion chromatography, affinity chromatography, high performance liquid chromatography (HPLC), nano-reverse phase liquid chromatography (nano-RPLC), polyacrylamide gel electrophoresis (PAGE), capillary electrophoresis (CE), reverse phase high performance liquid chromatography (RP-HPLC) or other suitable chromatographic techniques. Thus, in some embodiments, the mass spectrometric technique is directly or indirectly coupled with a one, two or three dimensional liquid chromatography technique, such as column chromatography, high performance liquid chromatography (HPLC or FPLC), reversed phase, ion exchange chromatography, size exclusion chromatography, affinity chromatography (such as protein or peptide affinity chromatography, immunoaffinity chromatography, lectin affinity chromatography, etc.), or one, two or three dimensional polyacrylamide gel electrophoresis (PAGE), or one or two dimensional capillary electrophoresis (CE) to further resolve the biological sample prior to mass spectrometric analysis.

A variety of mass spectrometry methods, including iTRAQ® and MRM, can be used. In some embodiments, quantitative spectroscopic methods, such as SELDI, are used to analyze protein expression in a sample. In one example, surface-enhanced laser desorption-ionization time-of-flight (SELDI-TOF) mass spectrometry is used to detect protein expression, for example by using the PROTEINCHIP™

(Ciphergen Biosystems, Palo Alto, Calif.). Such methods are well known in the art (for example see U.S. Pat. Nos. 5,719,060; 6,897,072; and 6,881,586). SELDI is a solid phase method for desorption in which the analyte is presented to the energy stream on a surface that enhances analyte capture or desorption.

Briefly, one version of SELDI uses a chromatographic surface with a chemistry that selectively captures analytes of interest, such as one or more proteins of interest. Chromatographic surfaces can be composed of hydrophobic, hydrophilic, ion exchange, immobilized metal, or other chemistries. For example, the surface chemistry can include binding functionalities based on oxygen-dependent, carbon-dependent, sulfur-dependent, and/or nitrogen-dependent means of covalent or noncovalent immobilization of analytes. The activated surfaces are used to covalently immobilize specific "bait" molecules such as antibodies, receptors, or oligonucleotides often used for biomolecular interaction studies such as protein-protein and protein-DNA interactions.

The surface chemistry allows the bound analytes to be retained and unbound materials to be washed away. Subsequently, analytes bound to the surface can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector.

In an additional example, the method may include detection of a protein of interest in a sample using an electrochemical immunoassay method. See, e.g., Yu et al., *J. Am. Chem. Soc.*, 128:11199-11205, 2006; Mani et al., *ACS Nano*, 3:585-594, 2009; Malhotra et al., *Anal. Chem.*, 82:3118-3123, 2010. In this method, an antibody that specifically binds the protein of interest is conjugated to terminally carboxylated single-wall carbon nanotubes (SWNT), multi-wall carbon nanotubes (MWCNT), or gold nanoparticles (AuNP), which are attached to a conductive surface. A sample (such as a blood, plasma or serum sample) is contacted with the SWNTs, MWCNTs, or AuNPs, and protein in the sample binds to the primary antibody. A second antibody conjugated directly or indirectly to a redox enzyme (such as horseradish peroxidase (HRP), cytochrome c, myoglobin, or glucose oxidase) binds to the primary antibody or to the protein (for example, in a "sandwich" assay). In some examples, the second antibody is conjugated to the enzyme. In other examples, the second antibody and the enzyme are both conjugated to a support (such as a magnetic bead). Signals are generated by adding enzyme substrate (e.g. hydrogen peroxide if the enzyme is HRP) to the solution bathing the sensor and measuring the current produced by the catalytic reduction.

In a particular example, the method includes a first antibody that specifically binds the protein of interest attached to an AuNP sensor surface. A sample (such as, but not limited to, a blood, plasma, serum, or urine sample) is contacted with the AuNP sensor including the first antibody. After the protein of interest binds to the first (capture) antibody (Ab1) on the electrode, a horseradish peroxidase (HRP)-labeled second antibody that specifically binds the protein of interest (HRP-Ab2) or beads conjugated to both a second antibody that binds the protein of interest and HRP are incubated with the sensor, allowing the second antibody to bind to the protein of interest. Biocatalytic electrochemical reduction produces a signal via reduction of peroxide activated enzyme following addition of hydrogen peroxide. Use of HRP is advantageous for arrays since immobilization of the electroactive enzyme label on the electrode eliminates electrochemical crosstalk between array elements, which can occur when detecting soluble electroactive product.

In some embodiments, isobaric tags for relative and absolute quantification (iTRAQ®) reagents are utilized to enable simultaneous quantification of multiple samples. The iTRAQ technology utilizes isobaric tags to label the primary amines of peptides and proteins. Multiple samples can be run simultaneously using different iTRAQ® reagents that label the individual samples with different mass identifiers. By way of example, sample one can be labeled with a mass identifier (or mass tag) that has a molecular weight of 114 amu, while sample two mass identifier (or mass tag) can have a molecular weight of 117. When the samples are combined and subjected to mass spectrometric analysis, the reporter ion in the tandem mass spectra of a peptide from sample two will have a predictable mass difference of three amu, compared to the reporter ion from sample one. This relative intensities of different reporter ions can be used for relative quantification of a peptide (and hence the protein from which they were derived).

In multiple reaction monitoring (MRM), tryptic peptides are used as markers for the abundance of specific proteins of interest, such as components of the Ras pathway, such as ERK and AKT. This selection is relatively straightforward if the protein has been identified by MS, such that the peptides are observable in a mass spectrometer (for example an LTQ Orbitrap). The process of establishing an MRM assay for a protein consists of a number of steps: 1) selection of the appropriate peptide(s) unique to the protein of interest and showing high MS signal response (prototypic peptides) which will help maximize the sensitivity of the assay; 2) selection of predominant peptide fragments specific (MS/MS) for the parent peptide (useful MRM transition); 3) for each peptide-fragment pair, optimization of specific MS parameters (for example, the collision energy) to maximize the signal response/sensitivity; 4) validation of the MRM assay to confirm peptide identity, for example by acquiring a full MS2 spectrum of the peptide in the triple quadrupole MS instrument used for MRM; 5) extraction of the final "coordinates" of the MRM assay, including the selected peptide and peptide fragments, the corresponding mass-to-charge ratios, the fragment intensity ratios, the associated collision energy, and the chromatographic elution time to be optionally used in time-constrained MRM analyses. In some examples, isotopically labeled internal peptide standards (with known concentrations determined by amino acid analysis) are used to facilitate absolute quantitation of selected peptides.

The concentration of the protein of interest, such as components of the Ras pathway, such as ERK and AKT, that is detected can be compared to a control, such as a sample from a subject known not to have an HIV infection. In other embodiments, the control is a standard value, such as a value that represents an average concentration of the protein of interest.

B. Methods for Detection of mRNA

Gene expression can be evaluated by detecting mRNA encoding the gene of interest. Thus, the disclosed methods can include evaluating mRNA encoding a component of the Ras pathway, such as EKT and/or ERK. The disclose methods can include evaluating mRNA encoding MORC3, STAU1, Loc710822, ILF3, HERC3, NAA38, PECR, MAP2K, LOC716474, EWSR, MGAT2 and/or NOSIP. Any of the methods disclosed herein can utilize the detection of mRNA.

RNA can be isolated from a sample from a subject, such as blood, serum, plasma, for example peripheral blood mononuclear cells, B cells, T cells and/or monocytes, and tissue samples, such as biopsy samples. Detecting an alteration in the amount of one or more of one or more components of the Ras pathway, such as AKT, ERK, MORC3, STAU1, Loc710822, ILF3, HERC3, NAA38, PECR, MAP2K, LOC716474, EWSR, MGAT2 and/or NOSIP indicates if an immunogenic composition is effective for inducing a protective immune response to HIV. Detecting an alteration in the amount of one or more of one or more components of the Ras pathway, such as AKT, ERK, MORC3, STAU1, Loc710822, ILF3, HERC3, NAA38, PECR, MAP2K, LOC716474, EWSR, MGAT2 and/or NOSIP indicates if an immunogenic composition is effective for preventing or treating an HIV infection.

RNA can also be isolated from a control, such as a subject known not to have an HIV infectino, using methods well known to one skilled in the art, including commercially available kits. General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Biotechniques 6:56-60 (1988), and De Andres et al., Biotechniques 18:42-44 (1995). In one example, RNA isolation can be performed using purification kit, buffer set and protease from commercial manufacturers, such as QIAGEN® (Valencia, Calif.), according to the manufacturer's instructions. For example, total RNA from cells in culture (such as those obtained from a subject) can be isolated using QIAGEN® RNeasy® mini-columns. Other commercially available RNA isolation kits include MASTERPURE® Complete DNA and RNA Purification Kit (EPICENTRE® Madison, Wis.), and Paraffin Block RNA Isolation Kit (Ambion, Inc.). Total RNA from tissue samples can be isolated using RNA Stat-60 (Tel-Test). RNA prepared from a biological sample can be isolated, for example, by cesium chloride density gradient centrifugation.

Methods of gene expression profiling include methods based on hybridization analysis of polynucleotides, methods based on sequencing of polynucleotides, and proteomics-based methods. In some examples, mRNA expression in a sample is quantified using Northern blotting or in situ hybridization (Parker & Barnes, Methods in Molecular Biology 106:247-283, 1999); RNAse protection assays (Hod, Biotechniques 13:852-4, 1992); and PCR-based methods, such as reverse transcription polymerase chain reaction (RT-PCR) (Weis et al., Trends in Genetics 8:263-4, 1992). Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). In one example, RT-PCR can be used to compare mRNA levels in different samples, such as from subject that is undergoing treatment, to characterize patterns of gene expression, to discriminate between closely related mRNAs, and to analyze RNA structure.

Methods for quantitating mRNA are well known in the art. In some examples, the method utilizes RT-PCR. For example, extracted RNA can be reverse-transcribed using a GENEAMP® RNA PCR kit (Perkin Elmer, Calif., USA), following the manufacturer's instructions.

For example, TAQMAN® RT-PCR can be performed using commercially available equipment. The system can include a thermocycler, laser, charge-coupled device (CCD) camera, and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

To minimize errors and the effect of sample-to-sample variation, RT-PCR can be performed using an internal standard. The ideal internal standard is expressed at a constant level among different tissues, and is unaffected by an experimental treatment. RNAs commonly used to normalize patterns of gene expression are mRNAs for the housekeeping genes GAPDH, β-actin, and 18S ribosomal RNA.

A variation of RT-PCR is real time quantitative RT-PCR, which measures PCR product accumulation through a dual-labeled fluorogenic probe (e.g., TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Heid et al., Genome Research 6:986-994, 1996). Quantitative PCR is also described in U.S. Pat. No. 5,538,848. Related probes and quantitative amplification procedures are described in U.S. Pat. Nos. 5,716,784 and 5,723,591. Instruments for carrying out quantitative PCR in microtiter plates are available from PE Applied Bio systems (Foster City, Calif.).

The steps of a representative protocol for quantitating gene expression using fixed, paraffin-embedded tissues as the RNA source, including mRNA isolation, purification, primer extension and amplification are given in various published journal articles (see Godfrey et al., J. Mol. Diag. 2:84 91, 2000; Specht et al., Am. J. Pathol. 158:419-29, 2001). Briefly, a representative process starts with cutting about 10 μm thick sections of paraffin-embedded tissue samples or adjacent non-diseased tissue. The RNA is then extracted, and protein and DNA are removed. Alternatively, RNA is isolated directly from a tissue sample. After analysis of the RNA concentration, RNA repair and/or amplification steps can be included, if necessary, and RNA is reverse transcribed using gene specific promoters followed by RT-PCR.

The primers used for the amplification are selected so as to amplify a unique segment of the gene of interest (such as mRNA encoding component of the Ras signaling pathway, such as AKT and/or ERK). In some embodiments, expression of other genes is also detected. Primers that can be used to amplify mRNAs of interest are commercially available or can be designed and synthesized according to well-known methods.

An alternative quantitative nucleic acid amplification procedure is described in U.S. Pat. No. 5,219,727. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In some examples, gene expression is identified or confirmed using the microarray technique. Thus, the expression profile can be measured in either fresh or paraffin-embedded cells, using microarray technology. In this method, nucleic acid sequences of interest (including cDNAs and oligonucleotides) are plated, or arrayed, on a microchip substrate. The arrayed sequences are then hybridized with isolated nucleic acids (such as cDNA or mRNA) from cells or tissues of interest. Just as in the RT-PCR method, the source of mRNA typically is total RNA isolated from tissue or cells, and optionally from corresponding tissues or cells from a subject known not to have an HIV infection.

In a specific embodiment of the microarray technique, PCR amplified inserts of cDNA clones are applied to a substrate in a dense array. In some examples, the array includes probes specific to Ras signaling pathway components, such as ERK and AKT. In some examples, probes specific for these nucleotide sequences are applied to the substrate, and the array can consist essentially of, or consist of these sequences. The microarrayed nucleic acids are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for genes of interest. Microarray analysis can be performed by commercially available equipment, following manufacturer's protocols, such as are supplied with Affymetrix GENECHIP® technology (Affymetrix, Santa Clara, Calif.), or Agilent's microarray technology (Agilent Technologies, Santa Clara, Calif.).

Serial analysis of gene expression (SAGE) is another method that allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., Science 270:484-7, 1995; and Velculescu et al., Cell 88:243-51, 1997).

In situ hybridization (ISH) is another method for detecting and comparing expression of genes of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as components of the Ras signaling pathway, such as AKT and ERK. Sample cells or tissues are treated to increase their permeability to allow a probe to enter the cells. The probe is added to the treated cells, allowed to hybridize at pertinent temperature, and excess probe is washed away. A complementary probe is labeled so that the probe's location and quantity in the tissue can be determined, for example, using autoradiography, fluorescence microscopy or immunoassay. The sample may be any sample of interest.

In situ PCR is the PCR-based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, $^3$H-CTP or biotin-16-dUTP), which have been incorporated into the PCR products during thermal cycling.

In some embodiments of the detection methods, the expression of one or more "housekeeping" genes or "internal controls" can also be evaluated. These terms include any constitutively or globally expressed gene (or protein) whose presence enables an assessment of gene (or protein) levels. Such an assessment includes a determination of the overall constitutive level of gene transcription and a control for variations in RNA (or protein) recovery. The methods can also evaluate expression of other markers.

The concentration of the mRNA of interest, such as a mRNA corresponding to ERK and AKT, that is detected is compared to a control, such as the concentration of the mRNA in a subject known not to have an HIV infection. In other embodiments, the control is a standard value, such as a value that represents an average concentration of the mRNA of interest expected in a subject who does not have an HIV infection. An increase in the level of one or more components of the Ras pathway indicates that the composition will induce a protective immune response.

EXAMPLES

The RV144 Thai trial is the first HIV vaccine clinical trial that resulted in significant protection from HIV acquisition (Rerks-Ngarm, S. et al., *N. Engl. J. Med.* 361, 2209-2220 (2009)). The vaccine regimen included the canarypox based vector (ALVAC-HIV) and the AIDSVAX HIV Clade B and E gp120 proteins formulated in Alum. Vaccination induced low frequency specific CD4+ T-cell responses and high titer binding antibodies to the HIV-1 envelope proteins (Env) (Rerks-Ngram et al., supra, (2009)). Antibodies directed to the variable regions 1 and 2 (V1/V2) of Env inversely correlated with the risk of HIV-1 infection (Haynes, B. F. et al., *N. Engl. J. Med.* 366, 1275-1286 (2012)). In addition, viral sequencing indicated immunologic pressure on two regions of the V2 variable loop resulting in an acquisition sieve effect that substantiated V2 as an important target for an HIV vaccine (Rolland, M. et al., *Nature* 490, 417-420 (2012)). Monomeric IgA to Env were directly correlated with the risk of HIV-1 infection due to IgA potentially interfering with IgG mediated ADCC (Tomaras, G. D. et al., *Proc. Natl. Acad. Sci. U.S.A* 110, 9019-9024 (2013)). Despite the success of the Thai trial, the efficacy of this vaccine was modest, waned over time and no virologic or clinical benefit was observed in vaccinated HIV infected individuals (Rerks-Ngram et al., op. cit., (2009)).

The primary correlate with a decreased risk of HIV acquisition in the RV144 trial was the titer of antibodies to a V1/V2 scaffold, whereas the secondary correlate was ADCC in the presence of low levels of envelope IgA. Interestingly however, there was a correlate for an increased risk of HIV acquisition and the serum titers of anti-envelope IgA. We used the $SIV_{mac251}$ macaque model of mucosal transmission and demonstrated that a RV144-like vaccine regimen in macaques also significantly decreased the risk of SIV acquisition. Surprisingly, an identical vaccine regimen, whereby the Alum was substituted with the MF59 adjuvant, failed to elicit protection despite the elicitation by the latter of higher antibody and T-cell responses. Interestingly, the two adjuvants elicited significantly different levels of anti envelope IgA, plasmablasts with the α4β7 and CXCR3 homing markers, and antibodies to cyclic V2 at mucosal sites. System biology analyses of pre- and post-vaccination demonstrated the modulation of different pathways in the two vaccine regimens and allow the identification of Ras associated pathways as a correlate for a decreased risk of SIV acquisition only in the vaccine regimen with Alum. Importantly, the modulation of Ras expression pre-vaccination existed and predicted a decrease risk of SIV acquisition. Ras is a central regulatory molecule that affects innate and adaptive immune responses, as well as cell motility and can be activated by several stimuli. Thus, modulation of the Ras pathways can be a predictive biomarker of efficacy with this and other vaccine modalities. In addition, activation of Ras by EGF or other stimuli before, during vaccination, or after vaccination can be used as an adjuvant to increase vaccine protection.

Example 1

ALVAC-SIV/gp120 Immunization Decreases the Risk of $SIV_{mac251}$ Acquisition

ALVAC-SIV/gp120 formulated in Alum induces similar immune responses to ALVAC-HIV/gp120 in humans (Pegu, et al, *Journal of Virology In Press* (2012)). These findings were extended during a study appropriately powered to detect a predicted vaccine efficacy ranging from 25-50%. We vaccinated 27 animals with the identical recombinant ALVAC vector backbone used in the RV144 trial expressing $SIV_{mac251}$ Gag-pro and gp120™ at weeks 0, 4, 12, and 24 (FIG. 1A). Instead of the HIV-1 clade B and E proteins used in the RV144 trial, we boosted twice (12 and 24 weeks) with $SIV_{mac251}$ and SIVsmE660 gp120 proteins formulated in Alum. The genetic diversity between the $SIV_{mac251}$ and $SIV_{smE660}$ envelope protein is 18% is similar to the inter clade diversity HIV clade B and E. A total of 47 controls were included in this study, 24 were concurrent controls, while 23 were historical and were either naïve or given Alum or MF59 adjuvants at weeks 12 and 24. All animals were exposed to weekly intra-rectal low doses of $SIV_{mac251}$ ($TCID_{50}$=120), starting at 4 weeks following the last immunization, for 10 consecutive weeks. ALVAC-SIV/gp120-protein-in-Alum significantly reduced the rate of SIV acquisition compared to unvaccinated controls (Log-rank=0.021), with an estimated efficacy of 40.2% at each mucosal challenge (FIG. 1B). Thus, ALVAC/gp120 vaccines formulated in Alum reduce the risk of HIV acquisition in humans and SIV acquisition in macaques. Furthermore, similar to HIV infected vaccinees in RV144, ALVAC-SIV/gp120 vaccination did not reduce peak or set point SIV viremia or prevent CD4+ T cell loss (FIG. 1C).

Example 2

MF59 Induces Significantly Higher Env Specific Antibodies and CD4+ T-Cell Responses To improve vaccine efficiency, we assessed the immunogenicity and relative efficacy of an ALVACSIV/gp120 vaccine, whereby the Alum adjuvant was substituted with the MF59 adjuvant in an otherwise identical vaccine regimen (FIG. 2A).

Figure 16A:
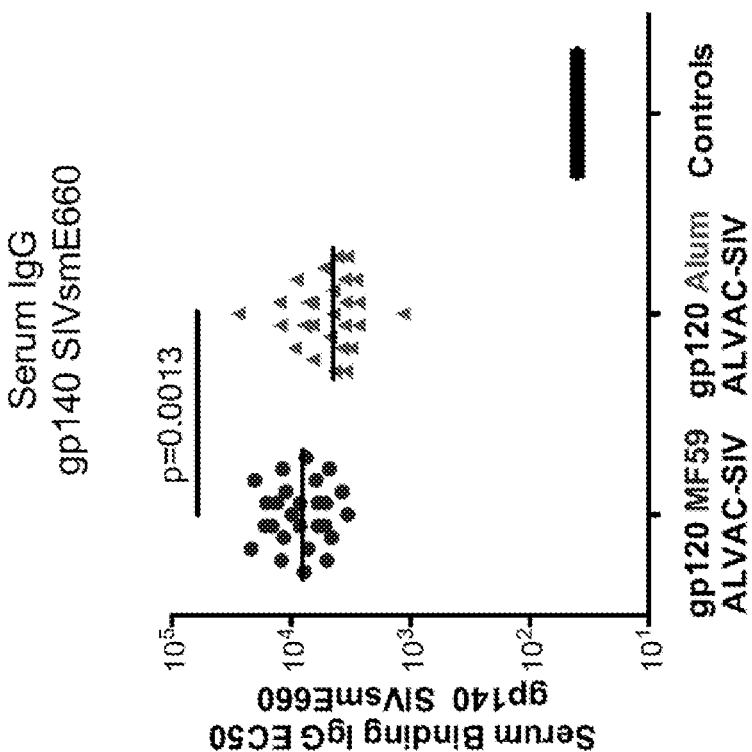
Figure 16B:
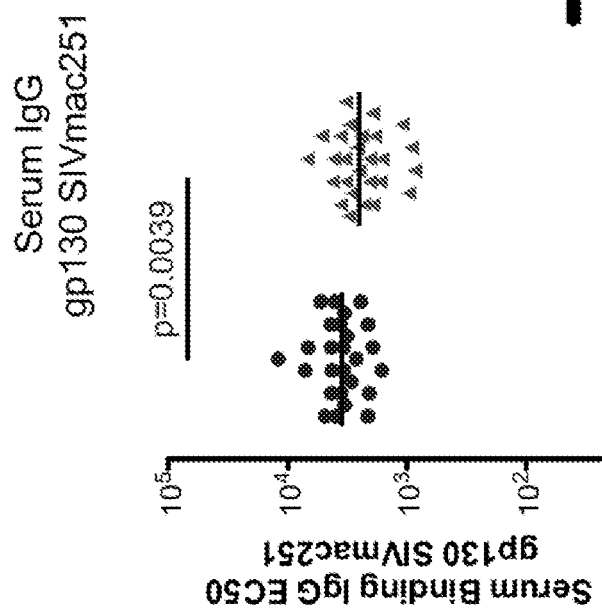
Figure 16D:
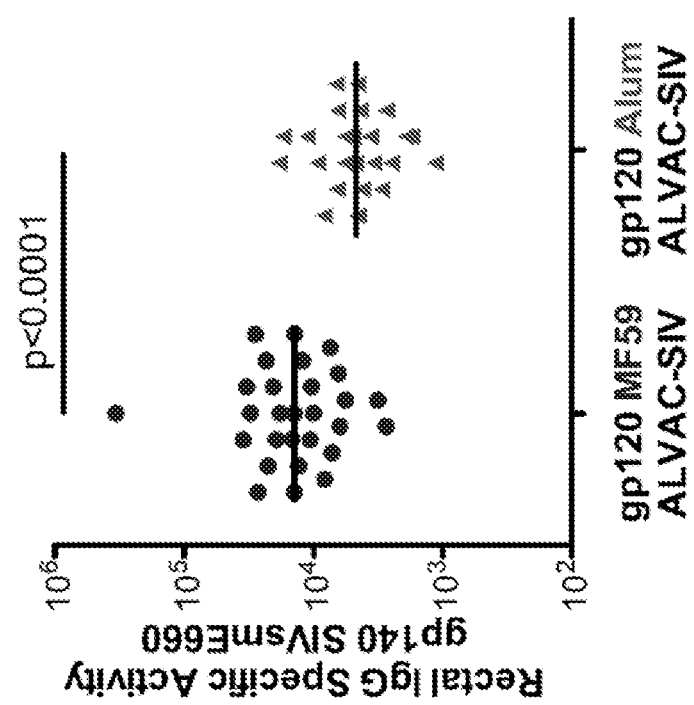
Figure 16C:
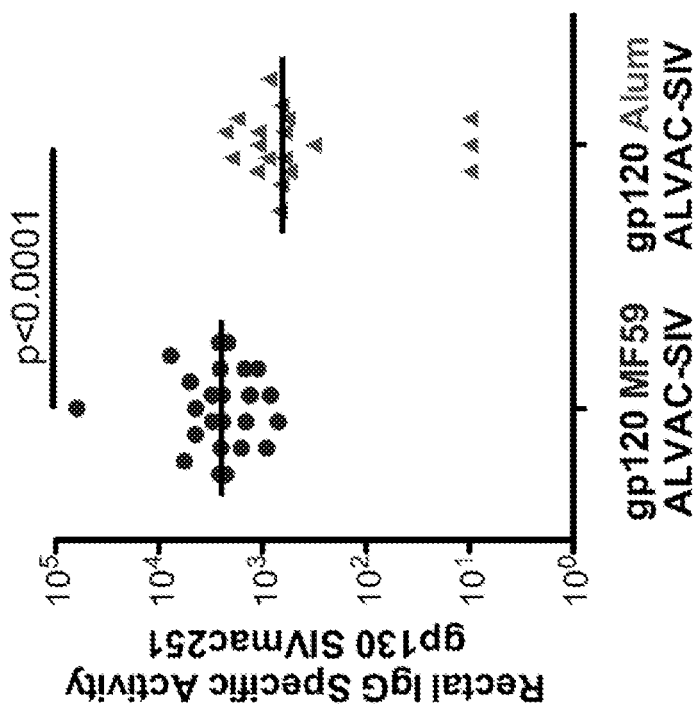
Figure 16E:
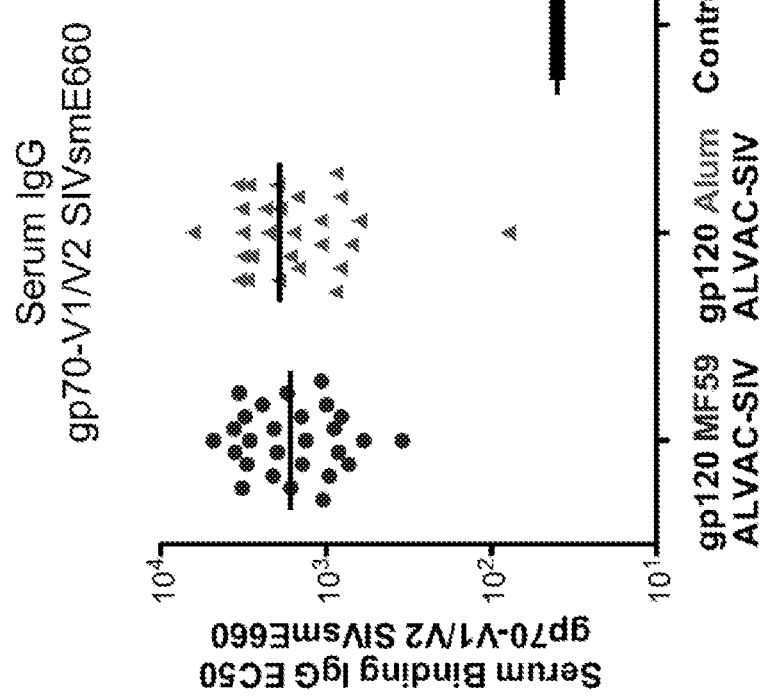
Figure 16F:
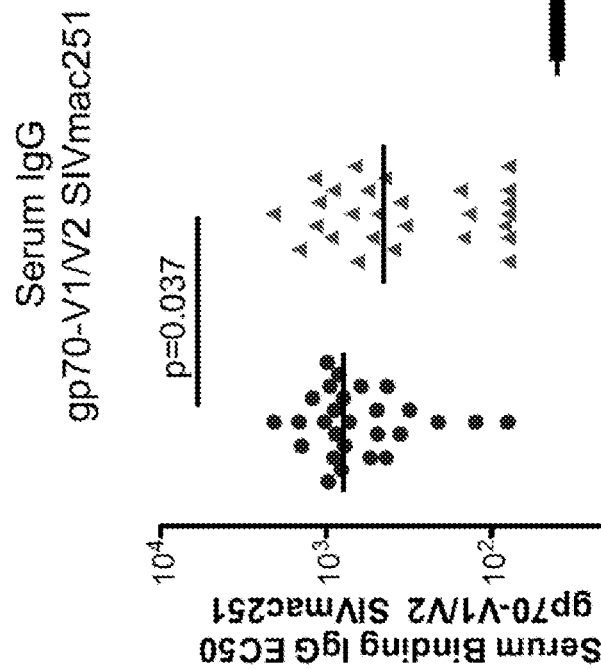
Figure 16H:
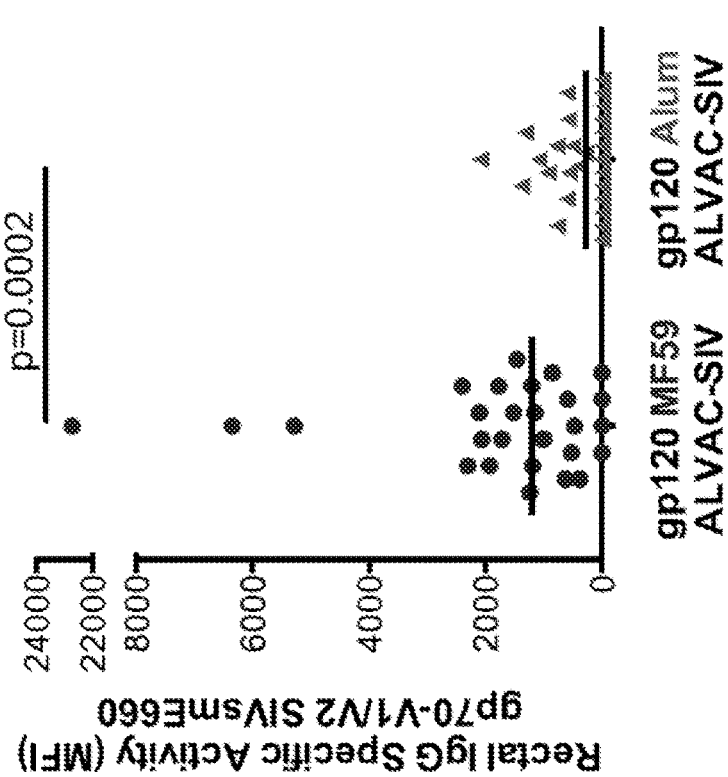
Figure 16G:
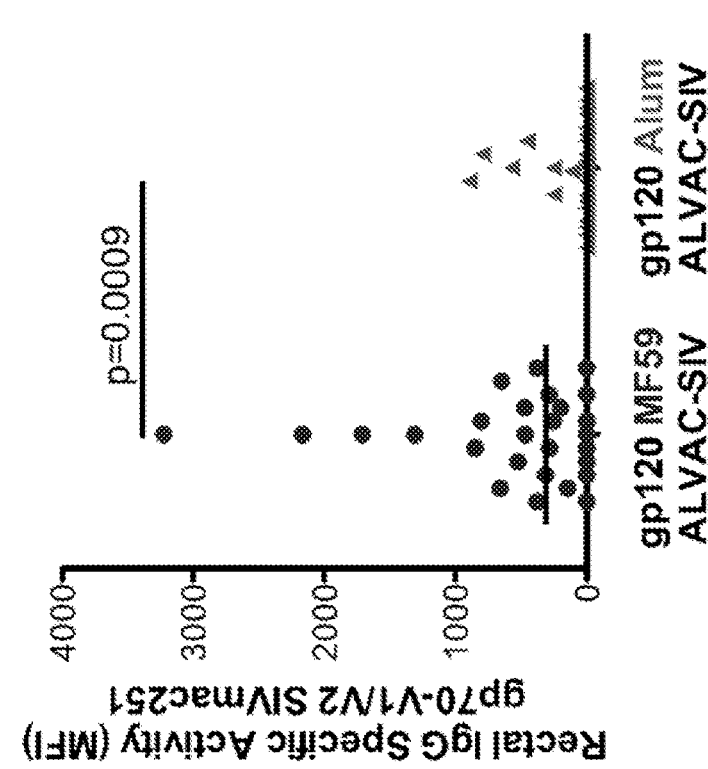
Figure 16I:
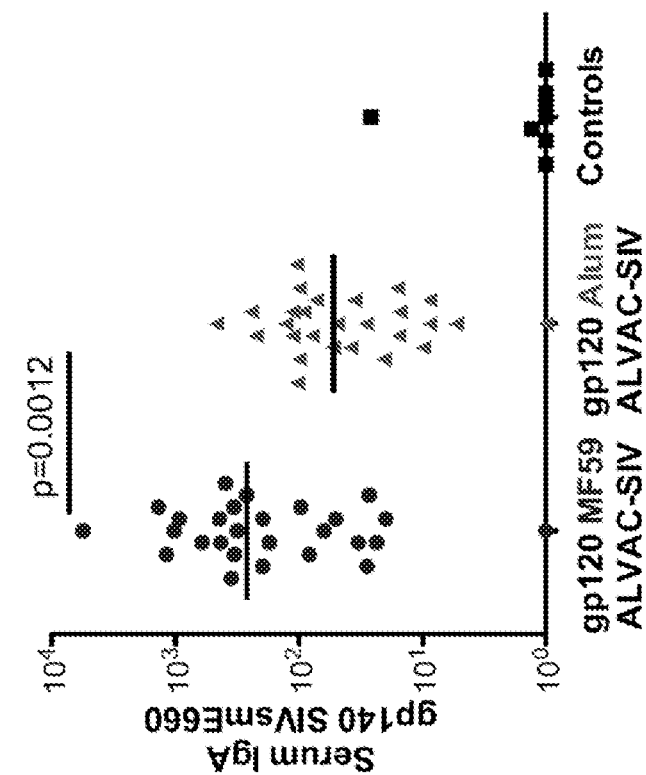
Figure 16J:
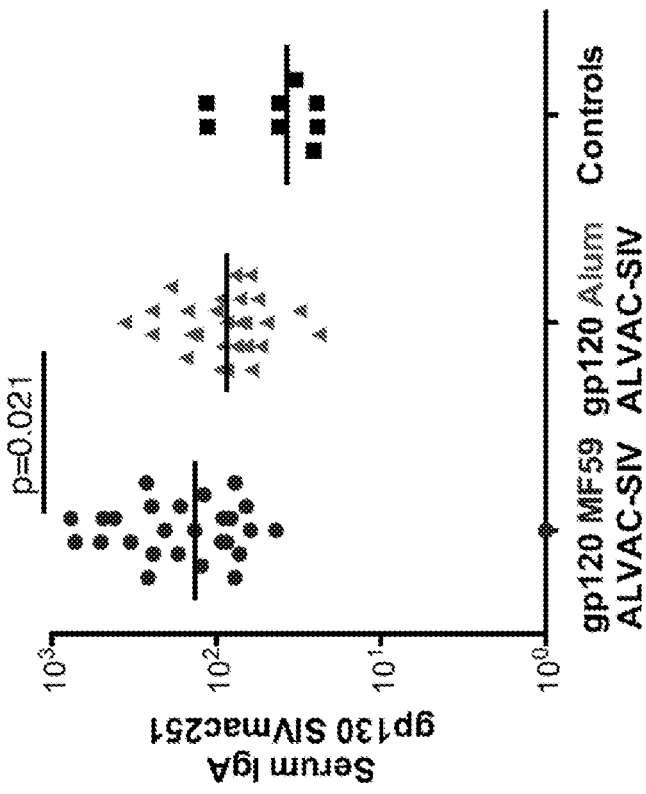
Figure 16M:
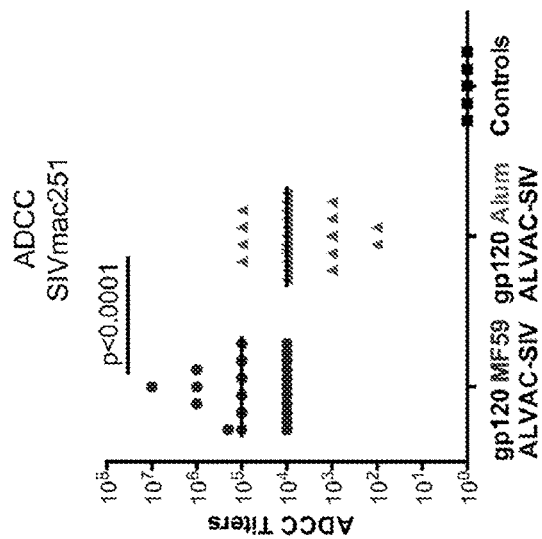
Figure 16L:
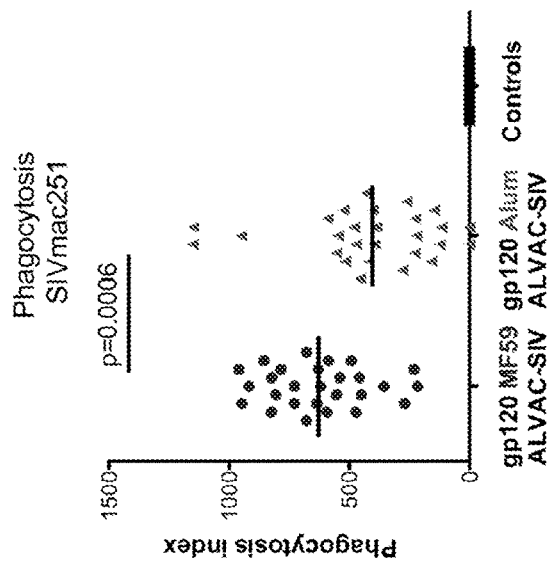
Figure 16K:
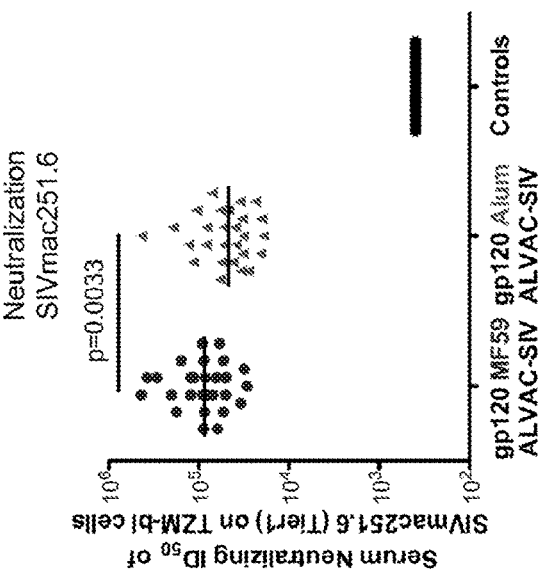

The MF59 regimen induced significantly high titer of binding antibodies to $SIV_{mac251}$ gp120 and $SIV_{smE660}$ gp140 envelopes in serum and in the mucosal secretions (FIGS. 16A-16J) and remarkably, MF59 also improved significantly functional antibody responses to the envelope, such as neutralization (FIG. 16K) phagocytosis (FIG. 16L) and ADCC titer (FIG. 16J). The sera of the animals immunized with the two regimens did not differ in the recognition of linear overlapping envelope peptides including the C1, V1, and V2 regions (FIG. 17B). MF59 significantly increased at antibodies to the scaffold gp70-V1/V2 loop of $SIV_{mac251}$ to the Alum group (FIG. 16E), but not to the gp70-V1/V2 loop of $SIV_{smE660}$ (FIG. 16F). The contribution of V2 to the humoral immunresponse was also tested using cyclic V2 peptides. We found that the MF59 increased significantly the Ab response to cyclic V2 of $SIV_{mac251}$ but not $SIV_{macE660}$.

A summary of immune responses elicited by the two vaccine regimens is provided in Table 1.

TABLE 1

| Differential Immune Responses induced by ALVAC and MF59 | | | |
|---|---|---|---|
|  | MF59 Median ± St. error | Alum Median ± St. error | p value < |
| *Serum Binding IgG | | | |
| Gp130 $SIV_{mac251}$ (EC50) | | | .0064 |
| Gp140 $SIV_{smE660}$ (EC50) | | | .0027 |

TABLE 1-continued

Differential Immune Responses induced by ALVAC and MF59

| | MF59 Median ± St. error | Alum Median ± St. error | p value < |
|---|---|---|---|
| V1/V2 SIV$_{mac251WY}$ (EC50) | | | .0429 |
| V1/V2 SIV$_{smE660BR}$ (EC50) | | | |
| **Cyclic V2 SIV$_{mac251}$ | | | |
| **Cyclic V2 SIV$_{smE543}$ | | | |
| *Serum Neutralizing Ab (TZM-bl cells, ID$_{50}$) | | | |
| SIV$_{mac251}$ stock virus | | | ns |
| SIV$_{mac251.6}$ (Tier1) | | | .0005 |
| SIV$_{mac251.30}$ (Tier2) | nd | nd | ns |
| SIV$_{smE660-CR54-PK-2A5}$ (Tier2) | nd | nd | |
| *ADCC | | | |
| % GranzymeB activity | | | |
| Number of positive animals | | | |
| *Phagocytosis (%) | | | |
| **CD4$^+$ T cell-responses in blood (ICS) | | | |
| SIV$_{mac251}$ env IFNγ | | | .0156 |
| SIV$_{mac251}$ env IL-2 | | | .0284 |
| SIV$_{mac251}$ env TNFα | | | ns |
| SIV$_{mac251}$ gag IFNγ | | | ns |
| SIV$_{mac251}$ gag IL-2 | | | ns |
| SIV$_{mac251}$ gag TNFα | | | ns |
| SIV$_{smE660}$ env IFNγ | | | |
| SIV$_{smE660}$ env IL-2 | | | |
| SIV$_{smE660}$ env TNFα | | | ns |
| SIV$_{smE660}$ env IFNγ | | | ns |
| SIV$_{smE660}$ gag IL-2 | | | ns |
| SIV$_{smE660}$ gag-TNFα | | | ns |

*Week 25
**Week 27
ns: non significant;
nd: non detectable

Figure 2C:
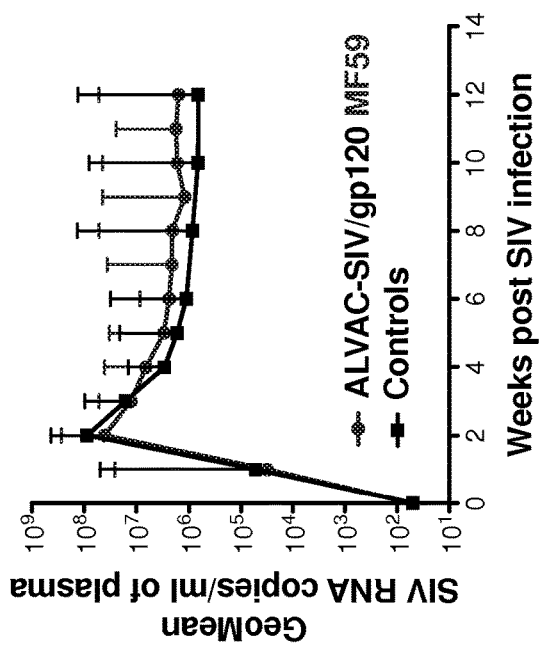
Figure 2B:
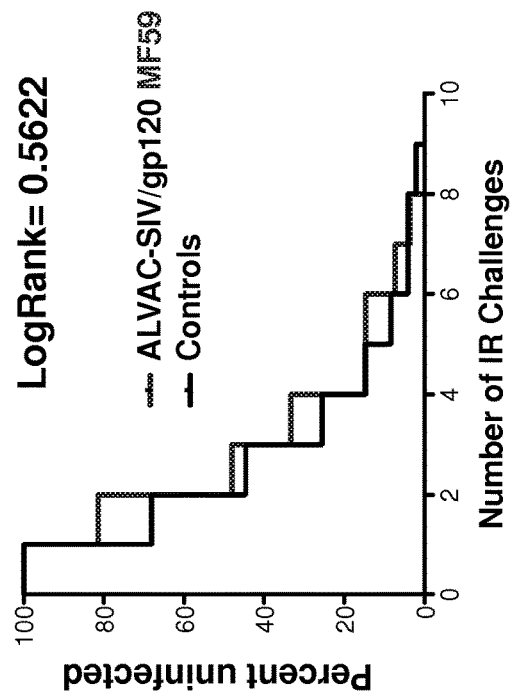
Figure 15A:
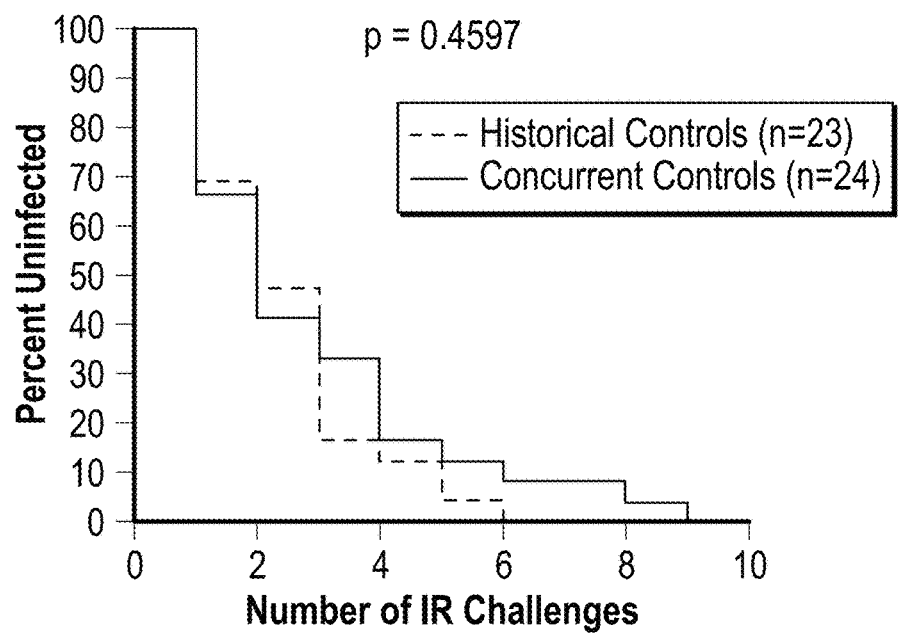
Figure 15B:
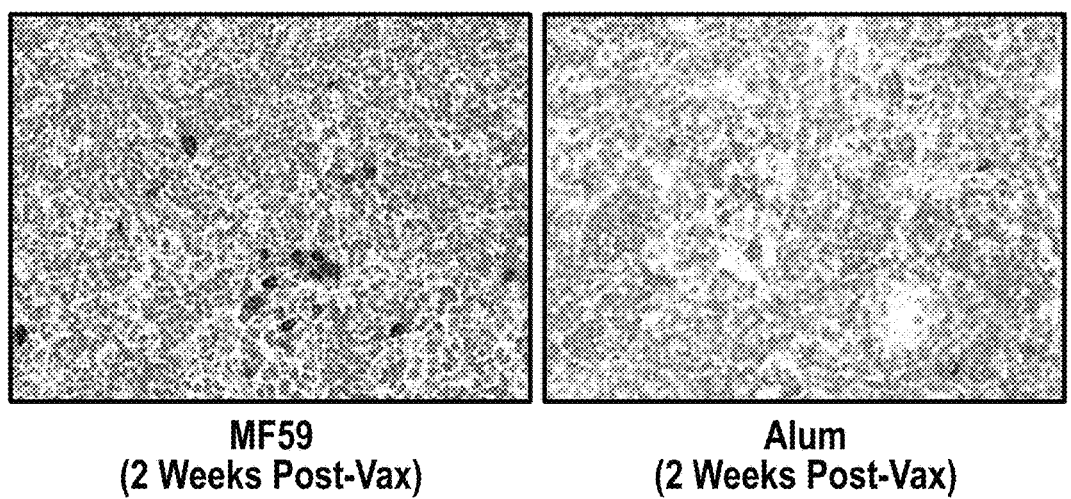
Figure 15C:
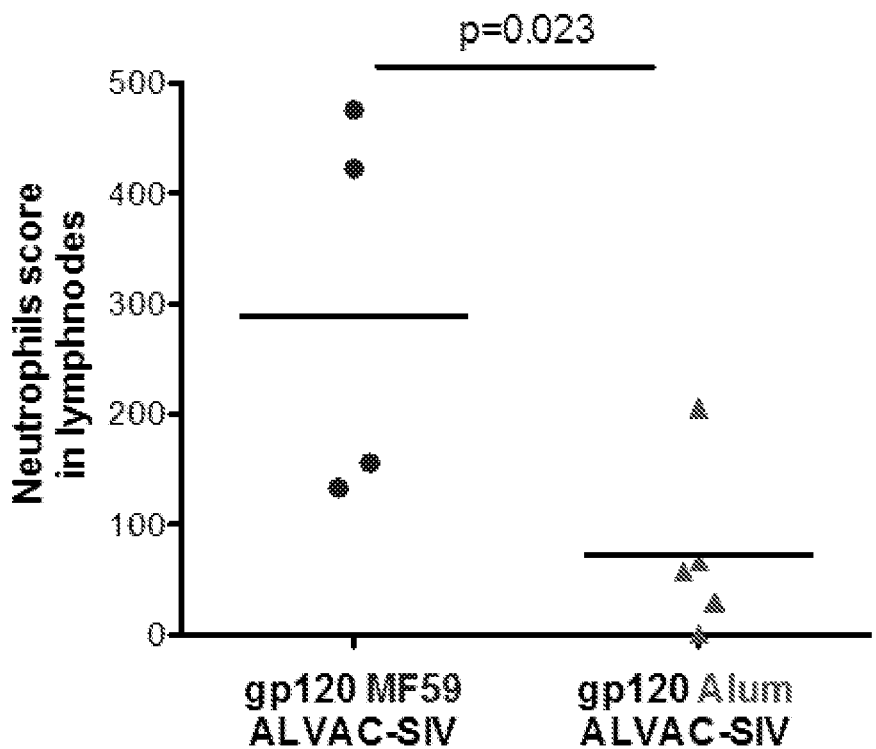
Figure 15D:
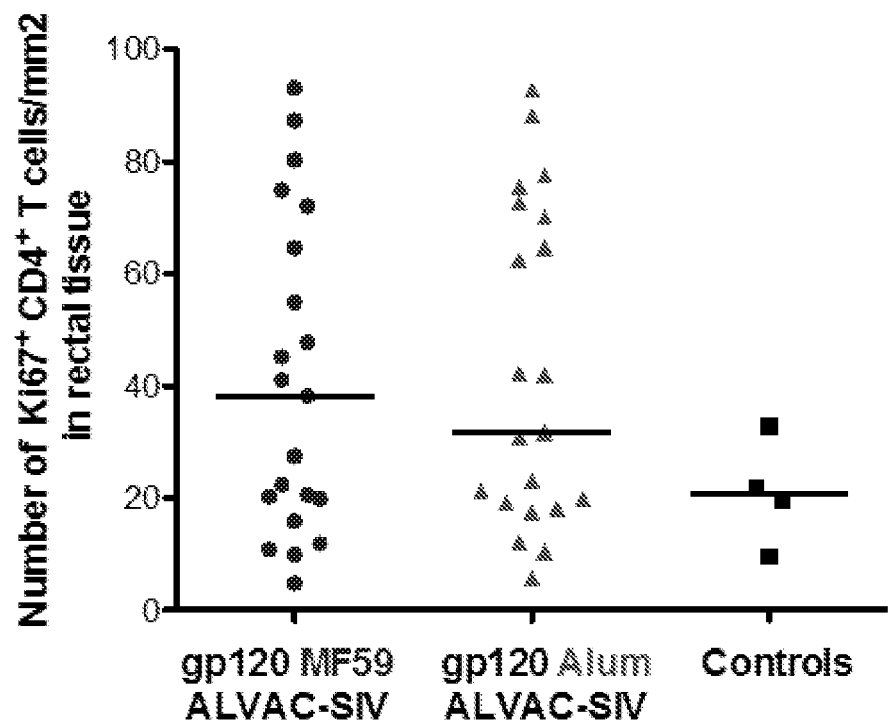
Figure 15E:
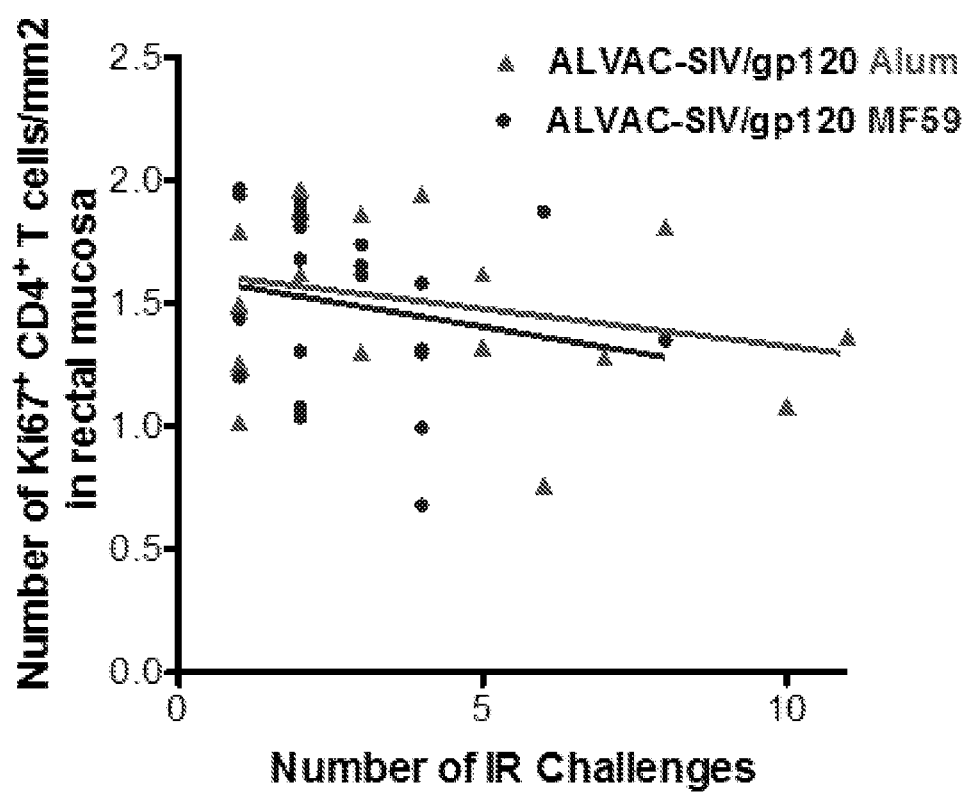

Surprisingly upon challenge exposure of the 27 macaques immunized with MF59, we observed a similar rate of SIV acquisition between vaccinated and control macaques (Log-rank=0.5622) (FIGS. 2A and 2B). As in the case of Alum, MF59 did not ameliorate virus control or CD4 loss following SIV acquisition (FIG. 2C). SIV-DNA levels measured in rectal tissue during the acute phase of infection were similar in all vaccinated animals and controls animals (FIG. 2E). We quantified the number of transmitted viral variants in all vaccinated macaques and found that the overall number of variants did not differ significantly between groups (FIG. 2D). However 33% (9/27) of animals in the MF59 group acquired more than one variant as opposed to 7% (2/27) in the Alum group (FIG. 2D). Because MF59 has been known to induce local inflammation and upregulates IFN-stimulated genes that in turn results in the recruitment of neutrophils and antigen presenting cells to the site of vaccination (Mosca et al., Proc. Natl. Acad. Sci. U.S.A 105, 10501-10506 (2008). Calabro et al., Vaccine 29, 1812-1823 (2011)), we measured the level of CD4$^+$ Ki67$^+$ T-cells at mucosal sites in a portion of the animals. No difference was found between the MF59 and Alum immunized animals (FIG. 15D).

Example 3

MF59 Significantly Increased the Titers of Envelope Specific IgA Responses

The class and subclass of vaccine-induced antibodies can affect their function and, in turn, vaccine efficacy. Increased HIV risk was associated with Env specific IgA in the RV144 trial[2, 4]. High titers of monomeric IgA were also induced by a DNA/Ad5 strategy that failed to protect from HIV acquisition in the HVTN505 trial in humans (Hammer et al., N. Engl. J. Med. 369, 2083-2092 (2013)). The MF59 regimen induced significantly higher IgA responses to the envelope of both SIV$_{mac251}$ and SIV$_{smE660}$ (FIGS. 16I and 16J).

Example 4

Figure 4E:
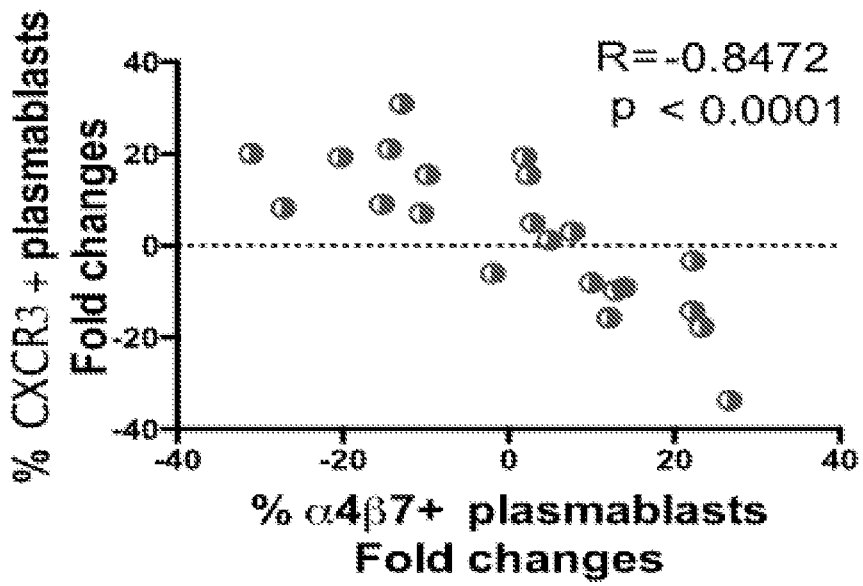
Figure 4F:
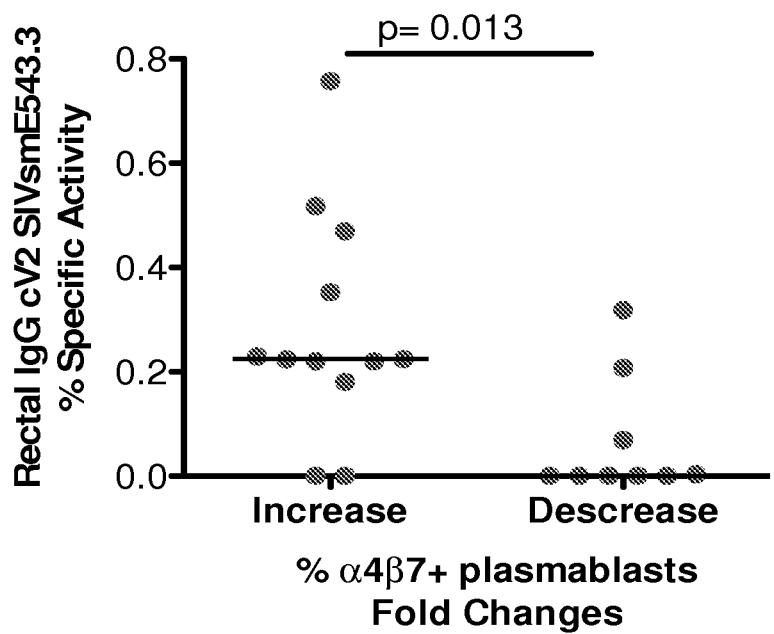
Figures 4G, 4H:
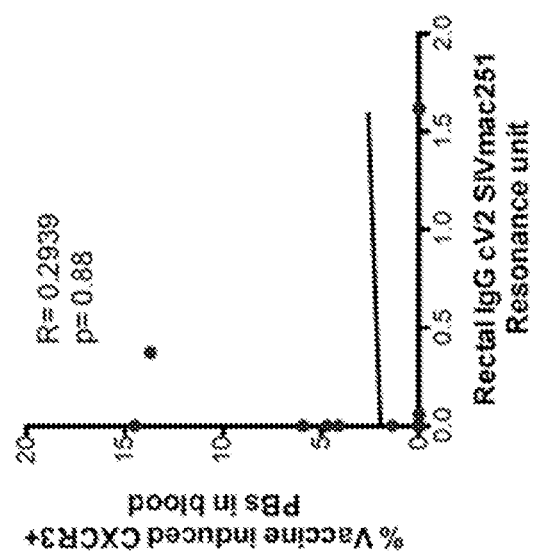

MF59-Regimen Reduces the Frequency of Plasmablasts Homing to the Gut and Mucosal Cyclic V2 Antibodies While a careful characterization of vaccine-induced responses in the blood has been conducted in the RV144 trial, the ability of these responses to home to the site of virus exposure and levels of mucosal immune responses, remain unknown. Thus, we examined the homing potential of antibody secreting cells in the blood at 1 week after the last immunization. Both vaccines induced plasmablasts (PB) but intriguingly, a significantly greater frequency of vaccine-induced PB expressed the mucosal homing integrin α4β7 (FIG. 4A). In contrast, PB induced by the MF59-regimen had a higher expression of the CXCR3 chemokine, associated with homing to inflammatory sites (Coffman et al., Immunity. 33, 492-503 (2010)) (FIG. 4G). We hypothesized that this measurement may be predictive of differences in antibodies specificity and titer at the mucosal sites, and measured antibodies to the linear and cyclic V2 in the rectal mucosa. We observed differences in the antibodies recognizing the first portion of the V2 loop that were present at the mucosal sites and in serum of animals in the MF59 group but not in the Alum-group (V2a-loop, FIGS. 18A-18F). Also, the Alum-group induced significantly greater activity to the cyclic V2 than the MF59 group (FIG. 4B). Mucosal cyclic V2 was directly correlated with the frequency of α4β7$^+$ PB induced by the Alum regimen but not by the MF59-regimen (FIG. 4C) and animals with an increase in vaccine-induced α4β7$^+$ PB in the alum-group had higher cyclic V2 activity the mucosal sites (FIG. 4F). Also in this group an increase of α4β7$^+$ PB corresponded to a decrease in CXCR3$^+$ PB (FIG. 4E).

Figure 4I:
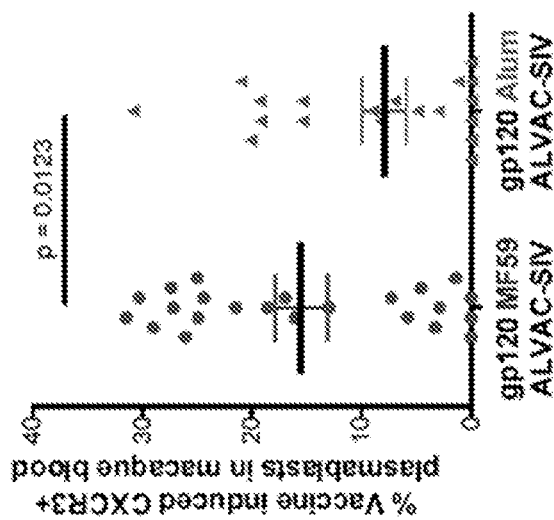

To confirm these findings were relevant in humans, we measured the frequency of vaccine-induced α4β7$^+$ and CXCR3$^+$ PB in the blood of vaccinees enrolled in the RV132 and RV135 studies two weeks after the last vaccination. As observed in macaques, the RV135 (ALVAC-HIV/gp 120 Alum group) favored the generation of α4β7$^+$ PB (FIG. 4D) while CXCR3$^+$ PB were similar in the two groups (FIG. 4I), possibly because these samples were collected at two weeks post the last immunization.

Example 5

Differences in Gene Modulations Between the Two Immunization Regimens and Correlates of Protection Defined by System Biology We studied by microarray analysis the transcriptome of 54 rhesus monkeys that were randomized into two treatment groups (ALVAC+MF59 and ALVAC+Alum). Samples were taken pre-vaccination (vax), after 1$^{st}$ immunization with ALVAC-SIV alone and after the 3$^{rd}$ that included a protein/adjuvant immunization together with recombinant ALVAC-SIV. All samples were taken prior to SIV challenge.

Figure 5:
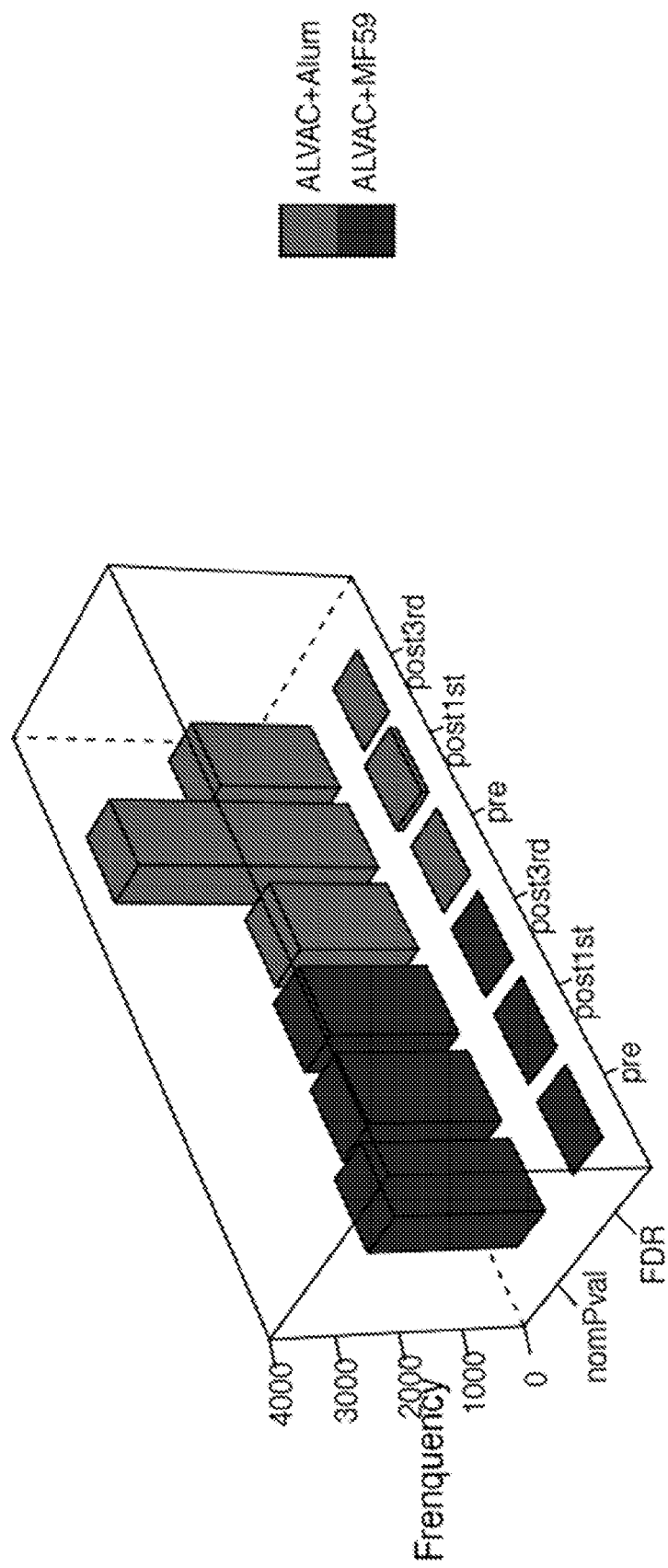

Differential expression analysis identified several transcripts differently expressed between post-vax (post-$1^{st}$ and post-$3^{rd}$) and pre-vax treatment (FIG. 5). However, no statistically significant difference in term of gene-expression between vaccine groups was observed.

Transcripts univariately associate with protection (i.e. number of SIV challenge to infection) were identified by fitting a linear model between the expression levels of specific transcript and the number of SIV challenge to infection. A moderated t-test was used to assess the statistical importance of this association. No transcripts were significantly associated with protection at the univariate level.

Figure 6:
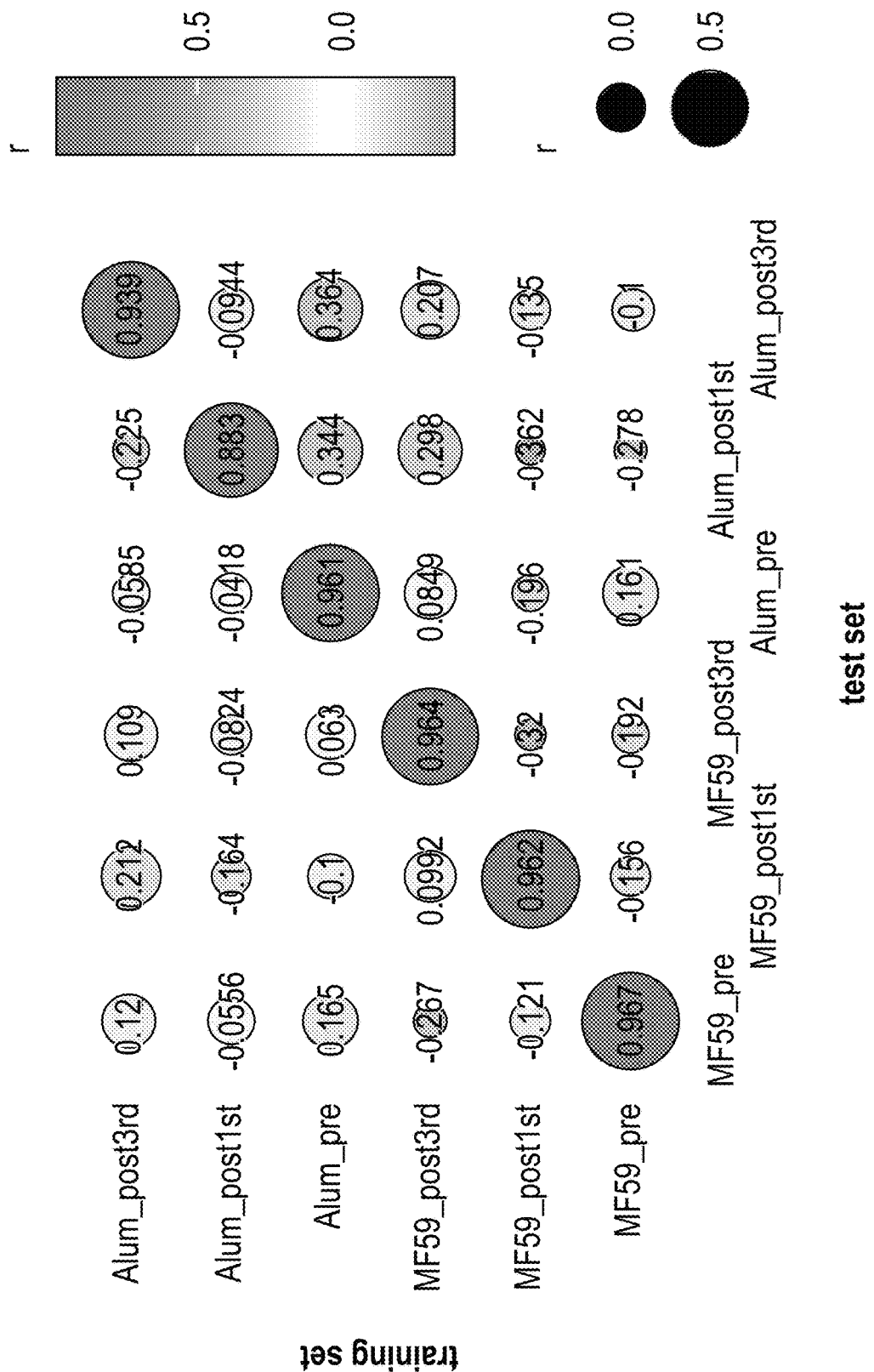

To determine whether transcripts associated with protection were shared between immunization steps or between vaccines, linear predictor of protections based on the top 50 best univariate transcripts (ordered by their t-statistic) were built for every vaccine (ALVAC+MF59 or ALVAC+Alum)× immunization step (pre-vax, post-$1^{st}$ or post-$3^{rd}$) combination and tested on the remaining samples. The statistical significance of the prediction was assessed by a t-test. Predictors of protection identified in one vaccine×immunization step combination didn't harbor any statistically significant prediction on the remaining samples suggesting that transcripts associated with protection were not shared between immunization steps or vaccines (FIG. 6).

Figure 7:
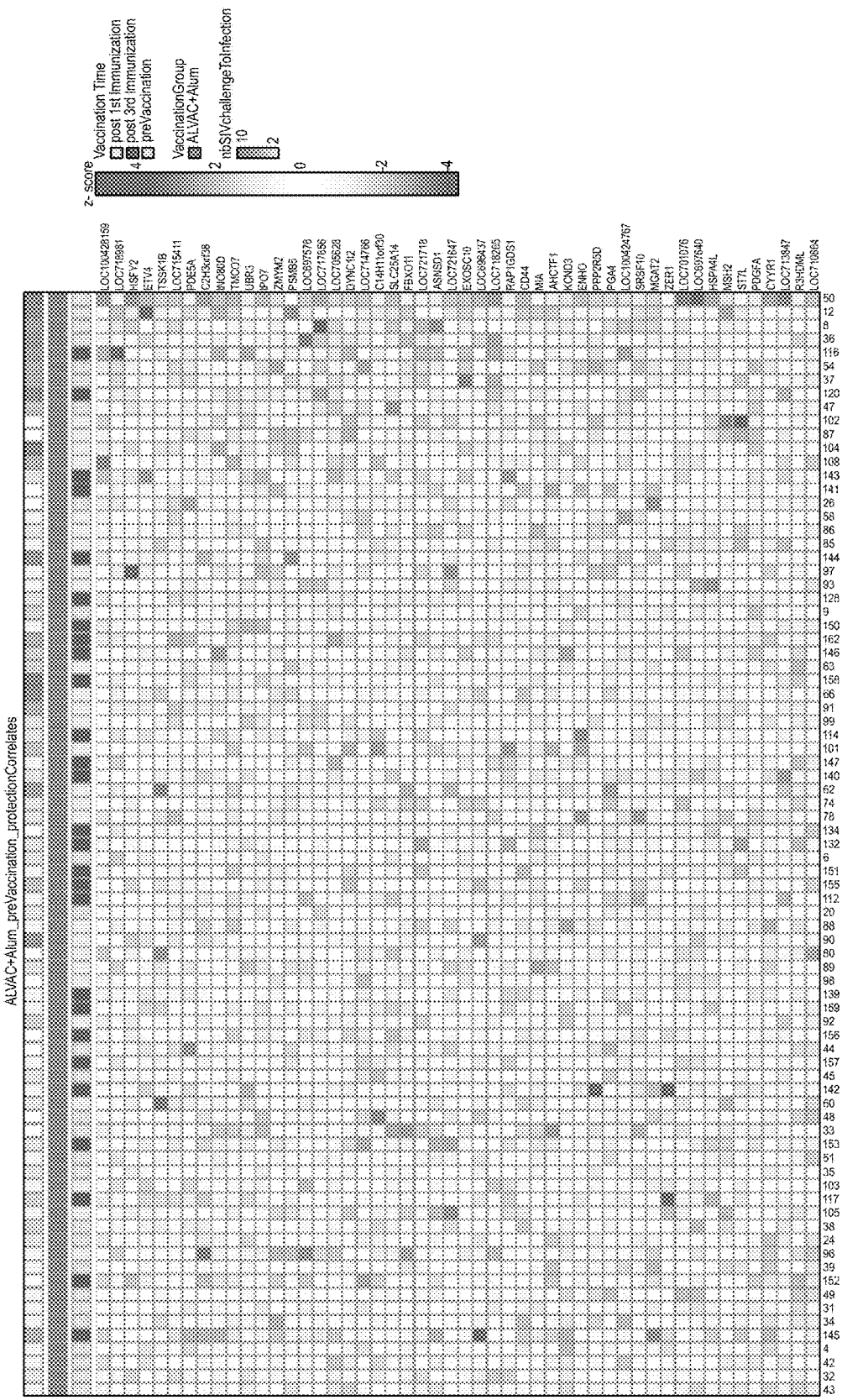

The only exception was that transcripts correlated to protection of ALVAC+Alum identified pre-vax maintained a significant predictive power when tested on post-vax samples (FIG. 7) suggesting that the state of monkeys prior to vaccination dictated (at least partially) which animal will be protected by the vaccine.

Figure 8A:
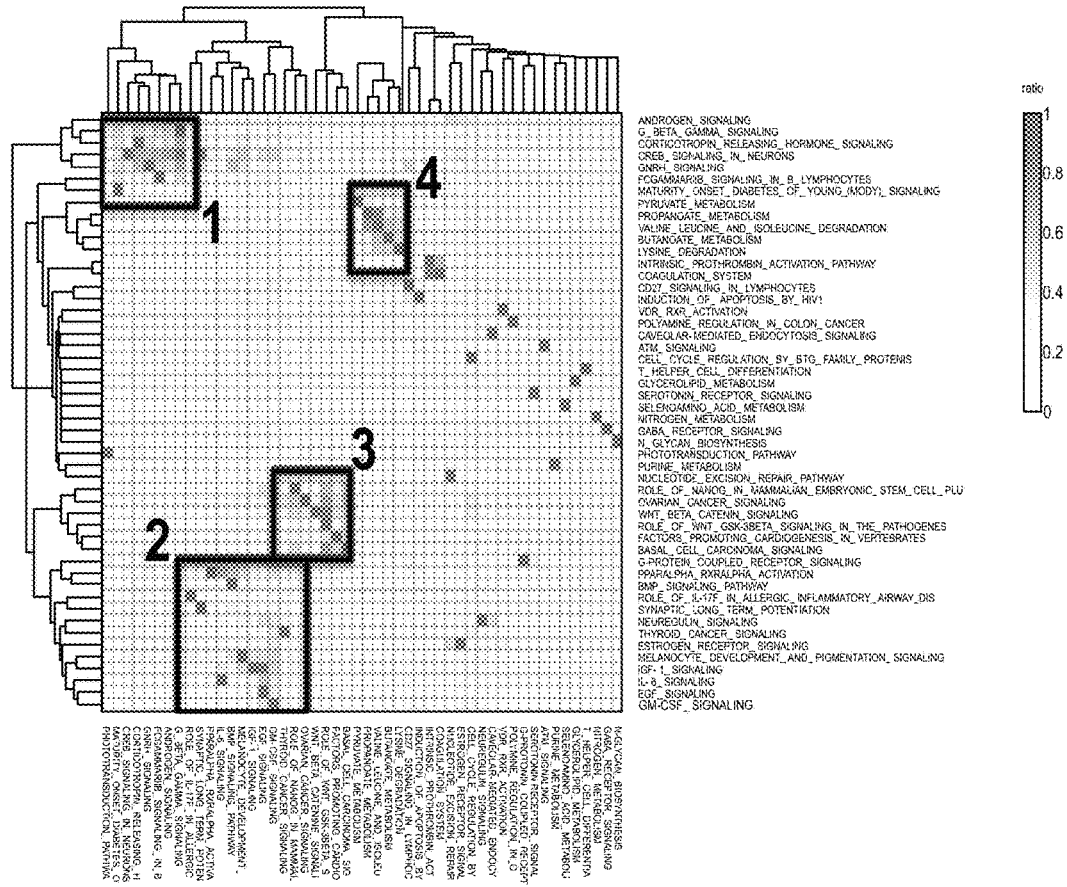
Figure 8B:
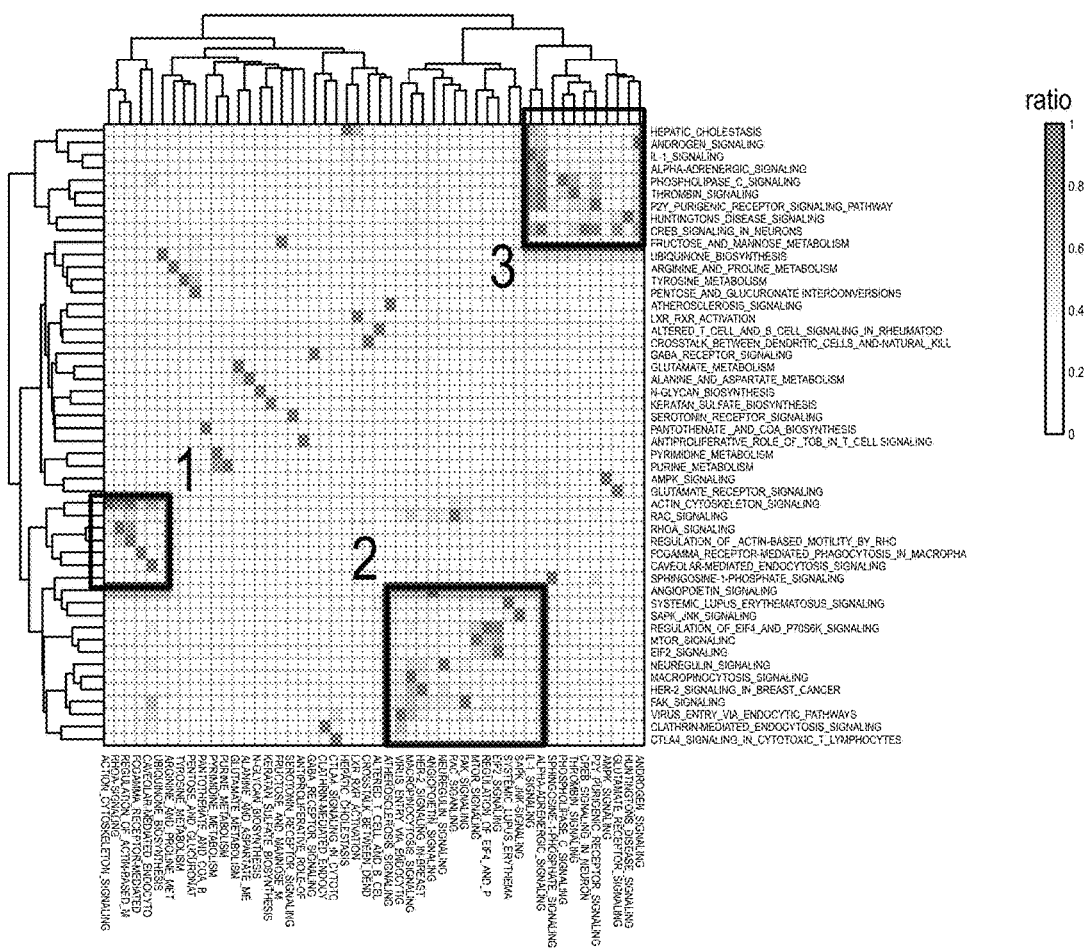
Figure 9:
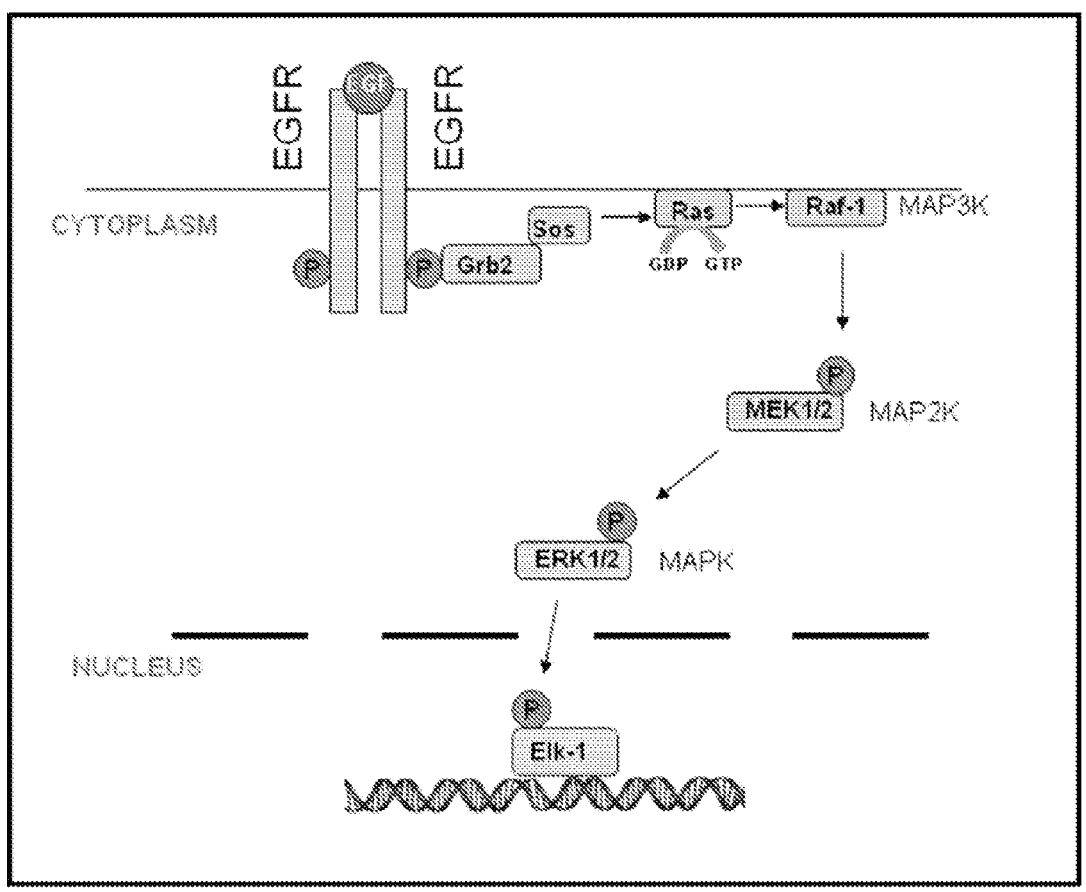
Figure 10:
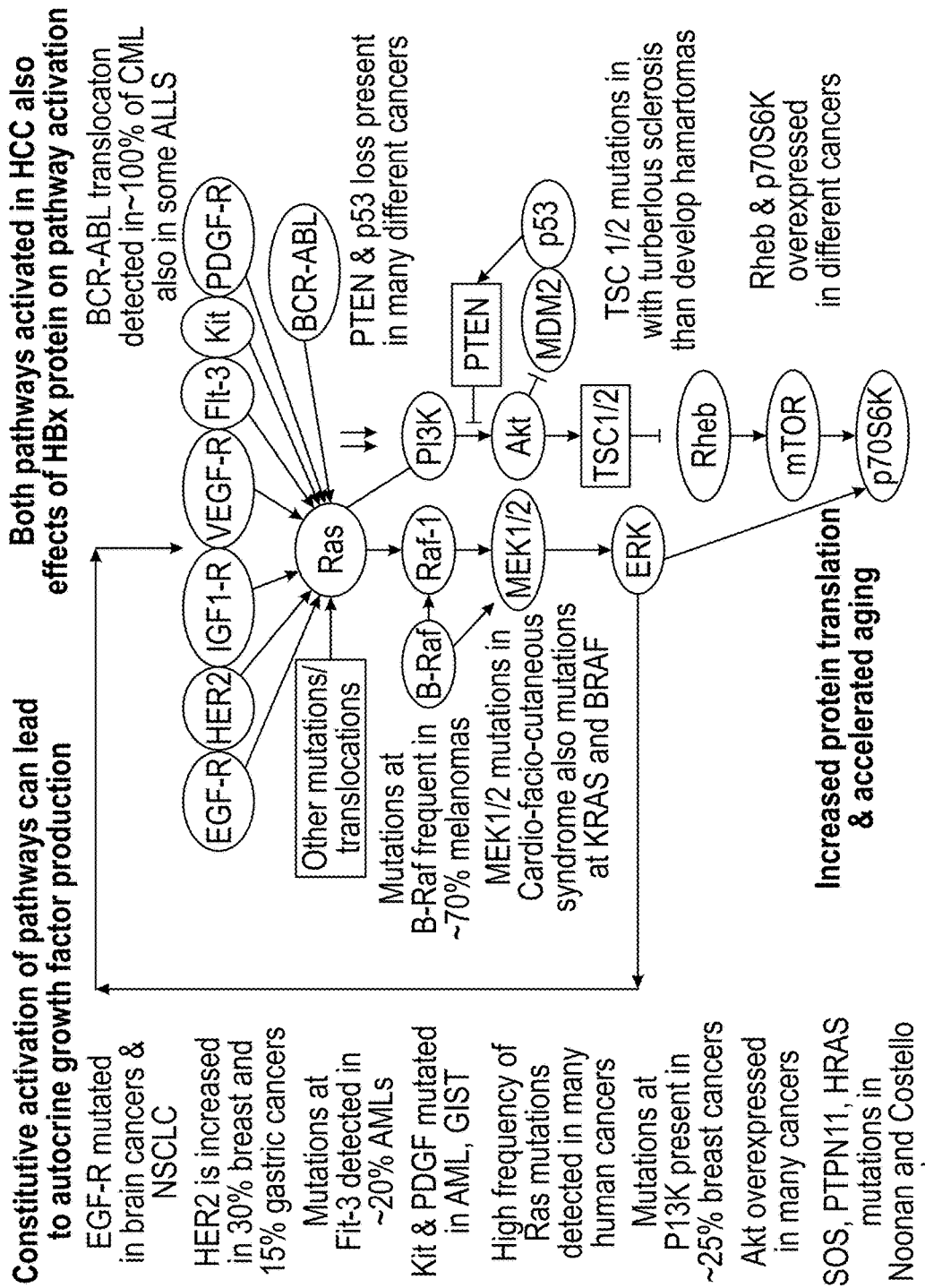
Figure 11:
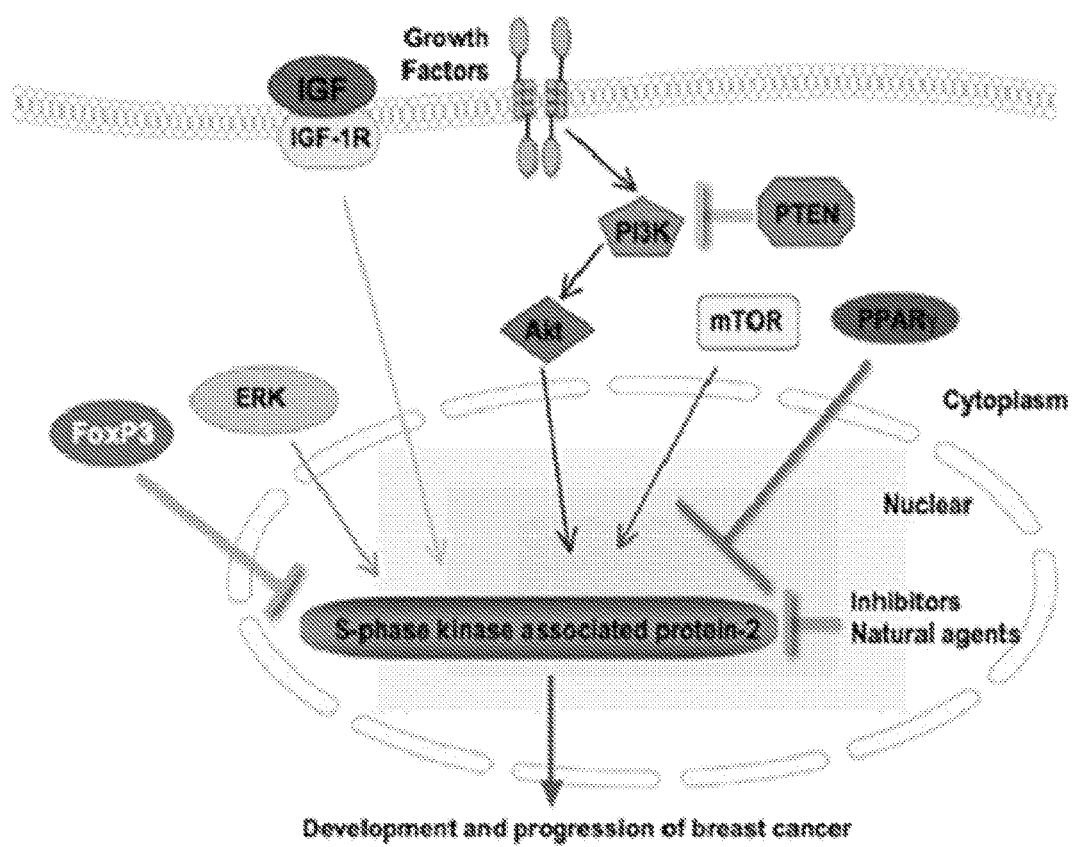
Figure 12:
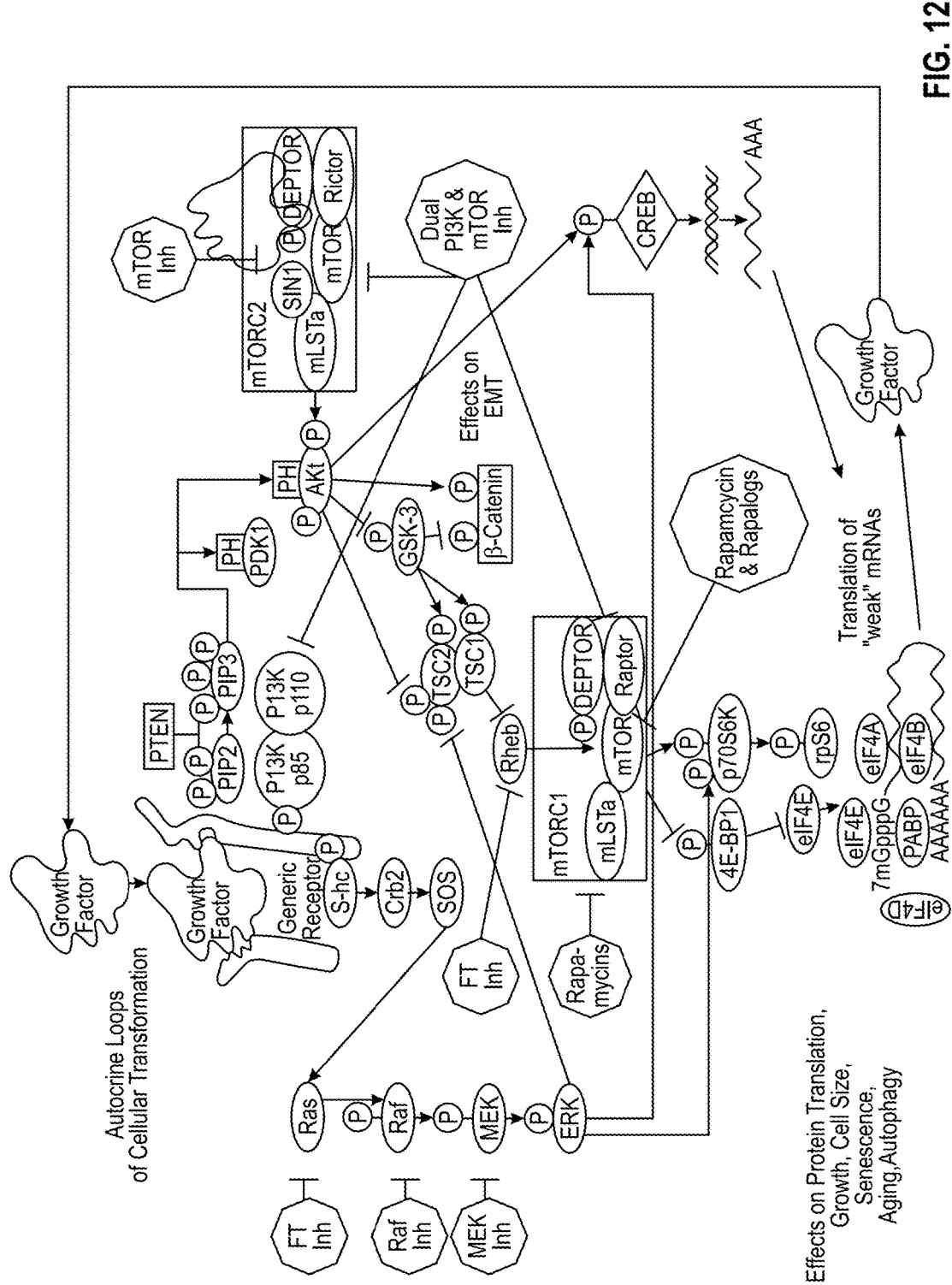

Gene Set Enrichment Analysis (GSEA) was performed in order to identify pathway associated with protection. Briefly, for every vaccine (ALVAC+MF59 or ALVAC+Alum)×immunization step (pre-vax, post-$1^{st}$ or post-$3^{rd}$) combination, transcripts were ordered by their corresponding t-statistic and enrichment of a priori build genesets (Ingenuity canonical pathway) among top transcripts correlated to protection was assess by weighted Kolmogorov-Smirnov test. Top enriched pathways were regrouped into modules based on the amount of correlated transcripts they share (as measured by the Jaccard index). RAS-related pathways were shared between top pathways associated with protection by ALVAC+Alum both pre-vax and post-vax (FIG. 8).

The SIV$_{mac251}$ model has been highly predictive of all the HIV efficacy trials conducted in humans. As disclosed herein, a similar vaccine regimen as used in the RV144 Thai trial, but expressing SIV genes, significantly reduced the risk of SIV$_{mac251}$ acquisition. In stark contrast, the same vaccine with the bivalent gp120 proteins formulated in MF59, demonstrated no protective efficacy. To understand the mechanisms of the lack of protection observed in the MF59 group, the immune responses induced by a vaccine that failed with one that significantly delayed SIV acquisition was compared. The MF59 strategy increased CD4$^+$ T-cell responses, multiple measures of antibody function and binding antibody titers including serum cyclic V2 responses. Surprisingly, despite higher serum V2 responses, we observed significantly lower mucosal V2 responses in the MF59 group compared to Alum. This suggests altered homing of antibodies directed to this critical target. Indeed, we observed that the Alum regimen generated higher frequency α4β7$^+$ PB that were correlated with mucosal cyclic V2 IgG and IgA. V2 can be detected on the surface of virions or infected cells and anti-V2 antibodies could interfere with virus-coreceptor engagement or participate in virus opsonization or ADCC. MF59 also altered the isotype of immunoglobulins induced by ALVAC-SIV/gp120 vaccines. Unexpectedly, MF59 boosted the titers of monomeric IgGA to the Env, a direct correlate of risk in the RV144 trial[2]. We found similarities in human samples from the RV135 and RV132 studies, suggesting that the MF59 may induce similar immune responses in humans.

System biology was used to identify Ras modulation pathways that were associated with a decreased risk of SIV acquisition. Ras is a central molecule in the innate and adaptive immune responses is found in exosomes and may represent a key component that bridges cross talk between B-cells, T-cells and antigen presenting cells. Its modulation can be a biomarker of vaccine efficacy and activators of the Ras pathway can be used to improve vaccine efficacy against HIV.

Example 6

Materials and Methods for Examples 1-5

Animals, Treatments, and SIV$_{mac251}$ Challenge:

All animals used in this study were colony-bred Rhesus macaques (*Macaca mulatta*), obtained from Covance Research Products (Alice, Tex.). The animals were housed and handled in accordance with the standards of the Association for the Assessment and Accreditation of Laboratory Animal Care International. A total of 54 macaques were immunized at weeks 0, 4, 12 and 24 with intramuscular inoculations of 10$^8$ PFU of recombinants ALVAC, expressing SIV$_{mac251}$ Gag-pro and gp120™. Twenty-seven macaques were boosted twice (12 and 24 weeks) with 200 microgram each of SIV$_{mac251}$- and SIV$_{smE660}$-gp120 proteins formulated in Alum and the other 27 animals were given 100 microgram each of the same proteins formulated in MF59. Of the 24 concurrent controls, 6 were given Alum, 12 were given MF59, and 6 were naïve. Of the 23 historical controls, 11 were given Alum and 12 did not receive neither Alum nor MF59. All macaques were challenged intrarectally with 10 low repeated doses of pathogenic SIV$_{mac251}$, given weekly starting at 4 weeks from the last immunization (week 28).

Measurement of Viral RNA:

SIV$_{mac251}$ in plasma was quantified by nucleic acid sequence-based amplification (Mooij, P. et al., *J. Virol.* 78, 3333-3342 (2004); Sumida et al., *J. Virol.* 78, 2666-2673 (2004); Malkevitch et al., *J. Immunol.* 170, 4281-4289 (2003); Pinto et al., *J. Immunol.* 171, 6774-6779 (2003)), as previously described (Vaccari et al., *Mucosal Immunol.* 1, 497-507 (2008)). Total RNA was extracted from isolated cells using the guanidium thiocyanate-phenol-chloroform method modified for TRIZOL® (Invitrogen, Carlsbad, Calif.). RNA (1 µg) was reverse-transcribed into first-strand cDNA using random hexanucleotide primers, oligo dT, and Moloney murine leukemia virus reverse transcriptase (Promega, Madison, Wis.). cDNA quantification was performed by real-time PCR, conducted with the ABI Prism 7900HT (Applied Biosystems, Foster City, Calif.). All reactions were performed using a SYBR green PCR mix (Qiagen, Valencia, Calif.), according to the following thermal profile: denaturation at 95° C. for 15 sec, annealing at 60° C. for 15 sec, extension at 72° C. for 15 sec (data collection was performed during the extension step). Primer sequences were as follows:

| | (SEQ ID NO: 13) |
|---|---|
| GAPDH forward | 5-GTCTGGAAAAACCTGCCAAG-3, |
| | (SEQ ID NO: 14) |
| GAPDH reverse | 5-ACCTGGTGCTCAGTGTAGCC-3; |
| | (SEQ ID NO: 15) |
| SIVgag forward | 5-GCAGAGGAGGAAATTACCCAGTAC-3, |
| | (SEQ ID NO: 16) |
| SIVgag reverse | 5-CAATTTTACCCAGGCATTTAATGTT-3. |

Intracellular Cytokine Staining Assay:

PBMCs ($2\times10^6$ cells) were stimulated with 2 µg/ml of the cognate peptides for 6 h in RPMI containing 10% human serum in the presence of 5 µg/ml of Brefeldin A (Sigma-Aldrich). Non-stimulated cells, as well as cells stimulated with super antigen SEM (SEA (staphylococcal enterotoxin A)+SEB (staphylococcal enterotoxin B) (Sigma-Aldrich)), were used as controls. These cells were then stained with the following surface-markers' specific antibodies for 15 min at 4° C.: CD4 (clone L200-PerCP-Cy5.5, BD Biosciences), CD8 (CD8-PE-Texas Red (ECD), Cedarlane), CD95 (clone DX2-PE-Cy5, BD Biosciences), CD28 (clone CD28.2-Pacific Blue, custom made, BD Biosciences), CCR7 (clone 3D12-PE-Cy7, BD Biosciences), PD-1 (clone MIH4-FITC, BD Biosciences). Cells were then fixed for 10 minutes in 100 µl 2% paraformaldehyde at room temperature (25° C.). To stain cells with antibodies specific for intracellular cytokines (IFN-γ-Alexa-700, IL-2-APC, TNF-α-PE; BD Biosciences), we incubated the cells with antibodies in 0.25% saponin (Sigma-Aldrich) for 30 minutes at 25° C. and analyzed them using the BD LSRII flow cytometer. Between 250,000 and $1\times10^6$ events were acquired for each condition. Data were then analyzed using DIVA software (BD Biosciences).

Serum Binding Antibodies:

IgG and IgA binding antibodies were measured by binding antibody multiplex assay as previously described (Tomaras et al., J. Virol. 82, 12449-12463 (2008); Bolton et al., Mucosal. Immunol. 5, 41-52 (2012)) and Surface Plasmon Resonance (SPR), as previously described (Flynn et al., Proc. Natl. Acad. Sci. U.S.A 108, 7131-7136 (2011)). Antibodies were eluted from rectal Wecks in cold elution buffer (1× protease inhibitor cocktail (Calbiochem), 0.25% BSA) by spinning 2× at 16,000×g for 15-20 min at 4° C. Total and SIV specific immunoglobulin were measured by ELISA according to manufacturer's instructions (Monkey IgG ELISA, Monkey IgA ELISA, Alpha Diagnostics (San Antonio, Tex.) and expressed as µg/ml to calculate specific activity for the binding responses. The SIV antigens utilized in both the multiplex binding antibody assay and SPR ar: $SIV_{mac239}$ p55 Gag (Protein Sciences), SIV p27 Gag (ImmunoDiagnostics, Woburn, Mass.), rgp41 (Immunodiagnostics), $SIV_{mac251}$ rgp130 (ImmunoDiagnostics, Woburn, Mass.) and SIV gp140 (provided by Dr. Bing Chen, Harvard). For analysis of SIV specific IgG by multiplex binding antibody assay: SIV proteins were coupled to microspheres (Bio-Rad), incubated with serial dilutions of samples and specific antibody binding detected by biotinylated anti-monkey IgG (Rockland) by mean fluorescent intensity (with background and blank bead subtracted). Positive and negative monkey sera controls were used in each assay and the midpoint titer (EC50) of each sample was calculated using 4 PL fit. Avidity of antibody binding was measured on a BIAcore 4000 instrument (BIAcore/GE Healthcare) using the multiplex array format (1×16) in which samples were flowed over duplicate spots of 8 different antigen surfaces on a series S CM5 chip (BIAcore/GE Healthcare). Proteins (pFB SIV gp140 and recombinant gp130 SIV $Mac_{251}$) were immobilized to about 5-10,000 RU and peptides were immobilized to about 1-3,000 RU. The following peptides were also used in this study—$SIV_{mac251}$ V2 linear, $SIV_{mac251}$ V2 S—S, cyclic DLV $SIV_{mac251}$, $SIV_{mac251}$ LDV gp41, cyclic LDV. Antigen surface activity was monitored using DBM5 IgG, HIVIG and serum samples as positive controls, and Synagis mAb as negative control. DBM5 IgG was titrated (0-100 ug/mL) to generate a standard curve for calculating weck sample IgG concentration. All weck extraction samples were run undiluted and injected over each of the flow cells with replicate spots (2×) at 10 uL/min for an association time of 120 s and a dissociation time of 450 s. Following each binding cycle, surfaces were regenerated with a short injection (20 s) of Glycine, pH2.0. Each surface activity was monitored by including DBM5 IgG (100 ug/mL) injection at regular interval of every 20 cycles. Bulk effect from a buffer injection was subtracted from each IgG sample binding data. Data analyses were performed with BIAevaluation 4000 and BIAevaluation 4.1 software (BIAcore/GE Healthcare). Kinetic binding responses were measured by averaging post-injection response unit (RU) over a 10 s window and dissociation rate constant, kd (s-1) was measured during the post-injection/buffer wash phase (after the first 30 s to allow stabilization of signal) following curve fitting to a Langmuir dissociation equation. A relative avidity binding score was calculated for each IgG sample as follows, Avidity score (RU.s)=Binding Response (RU)/kd, s-1, with higher binding responses and slower kd as an indicator of higher affinity interaction. For normalized responses, binding responses of a DBM5 IgG titration at known concentrations on an anti-monkey IgG chip surface were plotted to generate a calibration curve. Equivalent IgG concentration for each weck sample was calculated using the slope of the standard curve. Weck samples with binding responses above the highest DBM5 concentration of 100 µg/mL were reported as 150 µg/mL. Kinetic binding responses were normalized according to calculated concentrations.

Neutralizing Antibody:

Neutralization was measured as a reduction in luciferase reporter gene expression after a single round of infection in either TZM-bl or 5.25.EGFP.Luc.M7 (M7-Luc) cells as described previously (Andersson et al., J. Infect. Dis. 174, 977-985 (1996)). TZM-bl cells were obtained from the NIH AIDS Research and Reference Reagent Program. For the TZM-bl assay, 200 $TCID_{50}$ of virus were incubated with serial 3-fold dilutions of test sample in duplicate, in a total volume of 150 µl for 1 h out of 18 h at 37° C., as indicated, in 96-well flat-bottom culture plates. Freshly trypsinized cells (10,000 cells in 100 µl of growth medium containing 75 µg/ml DEAE-dextran) were added to each well. One set of control wells received cells and virus (virus control), and another set received cells only (background control). After the 48 h incubation, 100 µl of cells was transferred to 96-well black solid plates (Costar) for measurements of luminescence using the Britelite luminescence reporter gene assay system (PerkinElmer Life Sciences). Neutralization titers are the dilution at which relative luminescence units (RLU) were reduced by 50% compared to that in virus control wells after subtraction of background RLUs.

M7-Luc cells were maintained in RPMI 1640 containing 12% heat-inactivated fetal bovine serum, 50 µg gentamicin/ml, 0.5 µg puromycin/ml, 300 µg G418/ml, and 200 µg hygromycin/ml to preserve CCR5 and reporter gene plasmids. This is a CEMx174 cell clone that was produced by retroviral vector transduction to express CCR5 (CD4 and CXCR4 are expressed naturally) and transfection to contain Tat-responsive Luc and green fluorescence protein (GFP) reporter genes. For neutralization assays, 500 TCID50 of virus were incubated with serial dilutions of serum samples in triplicate, in a total volume of 150 µl for 1 h at 37° C. in 96-well flat-bottom culture plates. M7-Luc cells were suspended at a density of $5 \times 10^5$/ml in growth medium containing DEAE-dextran (10 µg/ml) but lacking puromycin, G418, and hygromycin. Cells (100 µl) were added to each well. One set of control wells received cells and virus (virus control), and another set received cells only (background control). Assay plates were incubated until approximately 10% of cells, in virus control wells, were positive for GFP expression by fluorescence microscopy (approximately 3 days). At this time, a 100-µl suspension of cells was transferred to a 96-well black solid plate (Costar) for measurements of luciferase activity as described above. Neutralization titers are the serum dilution at which the number of RLUs was reduced by 50% compared to virus control wells after subtraction of background RLUs.

Assay stocks of molecularly cloned Env-pseudotyped viruses ($SIV_{mac251}$ CS.41, $SIV_{mac239}$ 0.23, $SIV_{mac251}$ WY:30) were prepared by transfection in 293T-cells and were titrated in TZM-bl cells as previously described (Montefiori, Curr. Protoc. Immunol. Chapter 12, Unit (2005)). Assay stocks of uncloned TCLA-$SIV_{mac251}$ and $SIV_{mac251}$ CS/2002 letvin were produced in H9 and human PBMCs, respectively, and were titrated in M7-Luc and TZM-bl cells, respectively.

ADCC:

Antibody-dependent cell-mediated cytotoxic (ADCC) activity in serum samples collected at week xx was measured using the RFADCC assay as previously described[31]. Briefly, $SIV_{mac251}$ gp120 protein (Advanced Bioscience Laboratories Inc., Rockville, Md.) was used to coat CEM.NKr target cells which were then co-cultured with human PBMC effectors at an E:T ratio of 50:1. Serial dilutions of macaque sera were tested for ADCC activity in a 4 h assay and the ADCC titer was defined as the highest 10-fold serum dilution that generated ADCC activity above the background cutoff (mean ADCC activity over a dilution series of a pool of macaque negative sera plus 3 standard deviations). ADCC-mediated maximum percent killing of target cells (% ADCC Max killing) was defined for each positive sample as the highest percent killing mediated at any of the dilutions tested. Sera with percent killing below the cutoff value were scored negative.

Plasmablasts:

Twenty three macaques vaccinated with ALVAC-SIV/gDgp120 in MF59 and 22 animals vaccinated with ALVAC-SIV/gDgp120 adjuvanted in ALUM were bled before vaccination, as well 7 days after last immunization. PBMCs were prepared from peripheral blood using density gradient centrifugation and isolation with Ficoll-Paque (STEMCELL Technologies). Cells were then stained directly and then permeabilized and stained intracellularly with the Cytofix/Cytoperm (BD Biosciences). Acquisition was performed on a Becton Dickinson LSRII (BD Biosciences) and data were analyzed with FlowJo software (TreeStar). We defined plasmablasts those cells belonging to the B cells family repertoire (CD3−, CD14−, CD16−, CD56−, CD20+CD19+, CD20−CD19+, CD20+CD19−), not naïve (CD21−) highly proliferating (Ki67+/++), highly activated (CD38+/++), expressing the specific plasmablast's surface marker CD39. Human blood was stained with a similar panel; B cells were detected as CD20+/CD19+./CD27+.

Cyclic V2 in Rectal Swabs, ELISA for Cyclic SIV Peptides:

Briefly, 96-well Immunlon 2U-bottom ELISA plates were coated overnight at 4° C. with 100 µl of 2 µg/ml Streptavidin (Sigma-Aldrich) in bicarbonate buffer, pH 9.6 followed by 100 µl of 1 µg/ml of biotinylated cyclic V2 peptide (synthesized by JPT peptide Technologies, GmbH, Berlin, Germany) for 1 hr at 37° C. and then blocked with blocking buffer (0.5% milk in 1×PBS, 0.1% Tween 20, pH 7.4) overnight at 4° C. The contents were then dumped and 100 µl of serum samples diluted in blocking buffer were added. Serum was initially diluted 1:100 in blocking buffer and then serial 2-fold dilutions were performed and added to wells for 1 hr at room temperature. Wells were washed four times with wash buffer (PBS with 0.1% Tween 20, pH 7.4) using an automatic plate washer (BioStack washer, Biotech Instruments) and HRP-conjugated affinity purified goat anti-monkey IgG or IgA (1:1,000 in blocking buffer; The Binding Site) was added to wells for 1 hr at room temperature. Plates were washed four times with wash buffer and 100 µl/well of ABTS substrate was added, and color was allowed to develop at room temperature for 1 h in the dark. Plates were read at A405 nm using an ELISA reader Spectramax Plus, Molecular Devices. The data are expressed as end point titers, with the titers being defined as the reciprocal of the highest dilution that yielded an absorbance value above twice the background value (wells that did not contain peptides).

SIV V2 peptide was synthesized by JPT Peptide Technologies GmbH, Berlin, Germany. The peptide was allowed to fold and cyclize under thermodynamic control at high dilution, and the purity was determined to be greater than 90% by high performance liquid chromatography and mass spectrometry. The amino acid sequence of the SIV V2 peptide is based on the SIVsmE543-3 V2 domain from GENBANK® accession number U72748. The SIV V2 peptide sequence contains an N-terminal biotin tag and the sequence is as follows:

```
GF SIVsmE543
                                          (SEQ ID NO: 17)
CIKNNSCAGLEQEPMIGCKFNMTGLKRDKKIEYNETWYSRDLICEQPANG

SESKCY.

GF SIVmac251 full
                                          (SEQ ID NO: 18)
CIAQNNCTGLEQEQMISCKFNMTGLKRDKTKEYNETWYSTDLVCEQGNST

DNESRCY
```

Reagents and Surface Plasmon Resonance:

CM5 chips and the Biacore amine coupling kit were purchased from GE Healthcare, Piscataway, N.J., USA. Streptavidin was purchased from Invitrogen, Grand Island, N.Y. Affinity purified goat anti-monkey IgG and IgA (gamma chain or alpha chain-specific) antibody was purchased from Rockland Immunochemicals, Gilbertsville, Pa.

Surface plasmon resonance (SPR) measurements were conducted with a Biacore T200 using the CM5 chip as described previously (Pegu, P. et al., Journal of Virology In Press (2012)). Streptavidin was immobilized onto the chip using the amine coupling kit as directed by the immobilization wizard packaged within the T200 control software. 6700 RU of 1 uM streptavidin in 20 mM sodium formate, pH 4.2 (10 min. contact time, 10 uL/min flow rate) was immobilized. The biotinylated peptide was prepared at a concentration of 1 µM in 20 mM TRIS, pH 7.4 and allowed to flow (at 10 uL/min.) over the streptavidin coated surface of flow cell 4, until 3500 RU of SIV V2 peptide was captured.

The mucosal swabs were thawed on ice and centrifuged at 16,100 rcf, 4° C., for 5 min. The supernatant was diluted tenfold in TBS, pH 7.4, and then analyzed on the Biacore. The diluted mucosal samples were passed over the chip surface at a flow rate of 30 µL/min for 3 min followed by a 5 min dissociation period. At the end of the 5 min. period, a 20 ug/mL solution of affinity-purified gamma chain-specific goat anti-monkey IgG or IgA antibody was passed over the peptide coated-Ig bound surface for 2 min at a flow rate of 10 µL/min. After a 70 s dissociation period, the chip surface was regenerated and data analyzed as previously described using the BIAevaluation 4.1 software (Pegu et al., 2013). The reported response units (RU) for the IgG or IgA-specific values are the difference between the average value of a 5 second window taken 60 seconds after the end of the anti-IgG or anti-IgA injection and the average value of a 5 second window taken 10 seconds before the beginning of the anti-IgG or anti-IgA injection. The data (RU) are presented as dot plots for individual mucosal samples.

For determining the total IgG antibodies in the mucosal samples, anti-IgG immobilization on a CM5 chip was performed using 100 nM unconjugated gamma chain specific goat anti-monkey IgG (Rockland Inc., Gilbertsville, Pa.) in 20 mM sodium acetate, pH 4.2, with a 5 min contact time and 10 uL/min flow rate resulting in the immobilization of 9100 RU. Centrifuged mucosal samples (diluted 1:10) were passed over the chip surface at a flow rate of 30 µL/min for 3 min. followed by a 5 min. dissociation period. The relative amount of monkey IgG was determined using the same secondary injection and analysis strategy described above.

The peptide-specific IgG or IgA* in the mucosal samples was normalized and the data expressed as cyclic V2/total IgG or IgA.

Chemstrips were used to determine the blood contamination in mucosal samples. 10 uL of the mucosal supernatant sample was spotted onto a Chemstrip 5 OB Urine Test Strip (Roche, ref#11893467-160). After 60 s, any change in color was recorded for comparison to the manufacturer's color chart.

Microarray Analysis:

Microarray-analysis was conducted using biotinylated cRNA hybridized to HumanHT-12 version 4 BeadChips (Illumina). The arrays were scanned using Illumina's iSCAN and quantified using Genome Studio (Illumina). Analysis of the GenomeStudio output data was conducted using R/Bioconductor software packages (24). Quantile normalization was applied, followed by a log 2 transformation. The LIMMA package was used to fit a linear model to each probe and to perform (moderated) t-tests or F-tests on the compared groups (25). To control the expected proportions of false positives, the FDR for each unadjusted P value was calculated using the Benjamini and Hochberg method implemented in LIMMA. Principal component analysis was used as a dimensionality reduction method in R to generate plots for evaluation of similarities or dissimilarities between data sets. Gene Set Enrichment Analysis was used to annotate genes and rank canonical pathways (26).

Example 7

Mucosal Antibodies to V2 and RAS Activation in Vaccine Protection from $SIV_{mac251}$ Acquisition The HIV-Canarypox/gp120/alum regimen evaluated in the RV144 efficacy trial was the first vaccine to decrease the risk of HIV acquisition. We demonstrate here that a similar vaccine modality protected macaques from $SIV_{mac251}$ acquisition and further allowed for a more in-depth analysis of correlates of risk across multiple immune compartments. Specifically, mucosal IgG to cyclic V2 peptide was associated with lower risk of $SIV_{mac251}$ acquisition, and composite biophysical and functional profiles of SIV-specific antibodies in protected animals proved to be predictive of acquisition, highlighting possible mechanisms of protection from infection. Furthermore, transcriptional profile analysis pointed to a critical role for activation of the RAS pathway that facilitates cross talk among B-cells and T-cells and is associated with vaccine efficacy. These data underscore the importance of functional mucosal antibodies to V2 in protection from $SIV_{mac251}$ acquisition, and suggest that activation of RAS improves vaccine efficacy against HIV.

The RV144 HIV-vaccine trial, which combined a canarypox-based vector (ALVAC-HIV) and AIDSVAX HIV B/E gp120 proteins formulated in alum, resulted in modest protection from HIV acquisition. Serum IgG antibodies against the envelope (Env) variable regions 1 and 2 (V1/V2) inversely correlated with the risk of HIV-1 infection (Haynes et al., *N. Engl. J. Med.* 366, 1275 (Apr. 5, 2012)), and sieve analysis demonstrated genetic markers of immunologic pressure at positions 169 and 181 of V2 underscoring the critical importance of humoral immune responses directed at this region of the virus for protection from infection among vaccinees (Rolland et al., *Nature* 490, 417 (Oct. 18, 2012)). Monomeric serum IgA to HIV-Env positively correlated with the risk of HIV-1 acquisition (decreased vaccine efficacy) and demonstrated inhibition of IgG-mediated antibody-dependent cellular cytotoxicity (ADCC) (Tomaras et al., *Proc. Natl. Acad. Sci. U.S.A* 110, 9019 (May 28, 2013)). The macaque studies demonstrated ALVAC-SIV-induced protection from $SIV_{mac251}$ acquisition in a low dose neonatal challenge model, but not in adult high dose challenge models (Franchini et al., *Expert. Rev. Vaccines.* 3 Suppl 1:S75-88., S75 (August, 2004)). As disclosed herein, we immunized adult macaques with ALVAC-SIV/gp120/alum in a study powered to replicate RV144 and permit the systematic dissection of immune correlates and mechanisms of protection (FIG. 16A). We challenged animals intrarectally with 10 repeated low doses of $SIV_{mac251}$ starting 4 weeks after the last immunization. The time of challenge was chosen with the intent to model early exposure after vaccination, given that high-risk volunteers in HIV vaccine trials may be exposed to the virus soon after vaccination.

Vaccination with ALVAC-SIV/gp120/alum reduced the risk of $SIV_{mac251}$ acquisition as compared to unvaccinated controls (Log-rank test: p=0.0205), with an estimated vaccine efficacy of 44% at each challenge (FIG. 1B) (6). As reported for RV144, no post acquisition viral load effect was observed among vaccine recipient animals in the blood (FIG. 1C) and rectal mucosa (FIG. 2E), exhibited equivalent number of transmitted virus variants (FIG. 2D), and were not protected from CD4+ T-cell loss (FIG. 2F).

To assess the quantitative and qualitative features of immune responses that led to protection from SIV$_{mac251}$ acquisition, we studied humoral and cellular vaccine-induced immune responses. Vaccination induced serum and rectal IgG to the entire Env (FIGS. 16A-16D, to gp70-V1/V2 scaffolds (FIGS. 16E-16H), as well as serum IgA (FIGS. 16I-16J) recognizing both SIV$_{mac251}$ and SIV$_{smE660}$ strains, serum neutralizing antibodies of the tier 1 SIV$_{mac251.6}$ strain, phagocytosis and ADCC (FIGS. 21K-21M). No neutralizing antibodies to the SIV$_{mac251}$ challenge stock were detected.

Figure 3A:
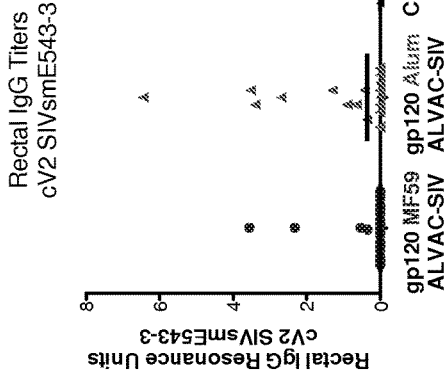
Figure 3B:
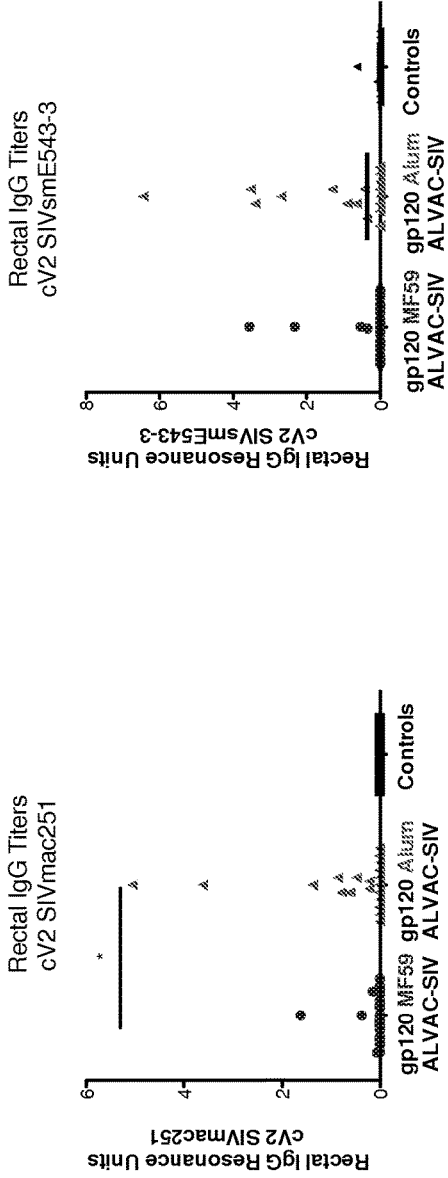
Figure 3C:
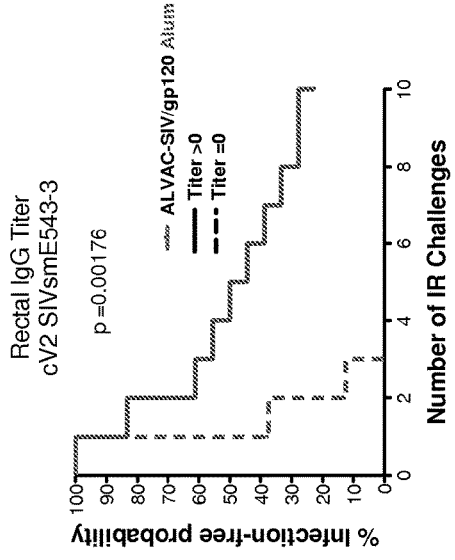
Figure 3D:
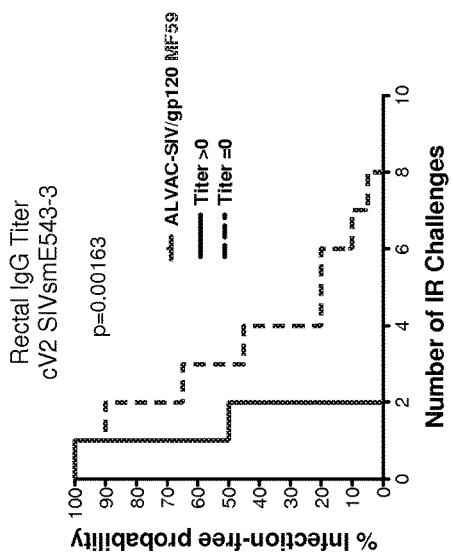

The magnitude of the T-cell and of the antibody responses depicted in (FIG. 16) did not correlate with the risk of SIV$_{mac251}$ acquisition. Therefore, we investigated possible differences in the Env epitope specificity in serum and mucosal secretions. Antibodies against SIV$_{mac251}$ gp130 and SIV$_{smE660}$ gp140 were detected in rectal mucosa secretions of vaccinated animals (FIGS. 16C and 16D). Recognition of gp120 linear overlapping peptides by serum (FIG. 17B) and mucosal (FIG. 17J) IgG revealed negligible levels of antibodies to V1, part of C1, and C3 in mucosal secretion. The presence of IgG that recognized linear V2 in the mucosa and serum did not correlate with SIV$_{mac251}$ acquisition. As antibodies to conformational epitopes of V2 were a correlate of decreased risk of HIV acquisition in RV144 (Haynes et al., *N. Engl. J. Med.* 366, 1275 (Apr. 5, 2012)), we next quantified antibody responses to the SIV$_{mac251}$ and SIV$_{smE543.3}$ gp70-V1/V2 scaffolds and cyclic V2 peptides in rectal secretions (FIGS. 16G, 16H, 3A and 3B). Cyclic V2 post-vaccination were considered as samples collected pre-vaccination had a high background both in control and vaccinated animals. Surprisingly only the percentage of specific activity to cyclic V2 of SIV$_{smE660}$ at mucosal sites correlated with a decreased risk of SIV$_{mac251}$ acquisition (Log-rank test: p=0.0019) (FIGS. 3C and 3D). Altogether, these results suggest that distinct antibody specificities are found in the blood and mucosa, and that responses against linear and conformational V2 have a differential impact on the risk of SIV$_{mac251}$ acquisition.

The association of cyclic V2-specific IgG at mucosal sites with protection prompted us to investigate the mucosal homing markers on plasmablasts/Antibody-secreting cells (ASC). We found that alum did not alter the overall frequency of total blood ASC expressing the mucosal homing integrin α4β7 or CXCR3 that targets plasmablasts to LN, however, while frequencies of ASCs per se did not correlate with protection, animals that had higher frequency of α4β7+ ASC in blood (FIG. 4E) had lower levels of CXCR3+ ASC and higher rectal IgG to cyclic V2 (FIGS. 4C and 4F).

There was a negative correlation between the frequency of α4β7+ ASC and serum Env IgG, a positive correlation between the α4β7+ ASC frequency and the level of rectal IgA to cyclic V2, and a positive correlation between CXCR3+ ASC and serum IgA to the gp70-V1/V2 scaffold.

Figure 13A:
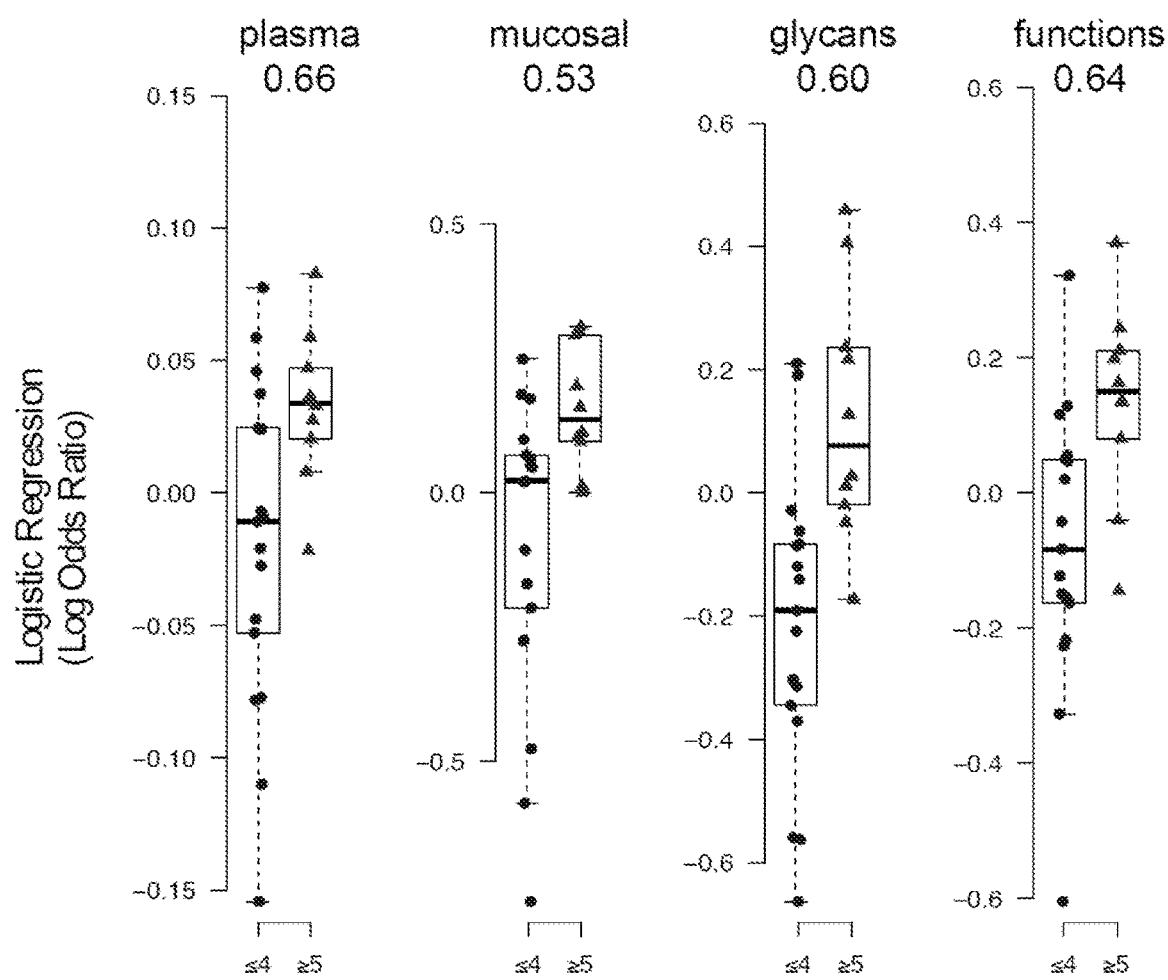
Figure 13B:
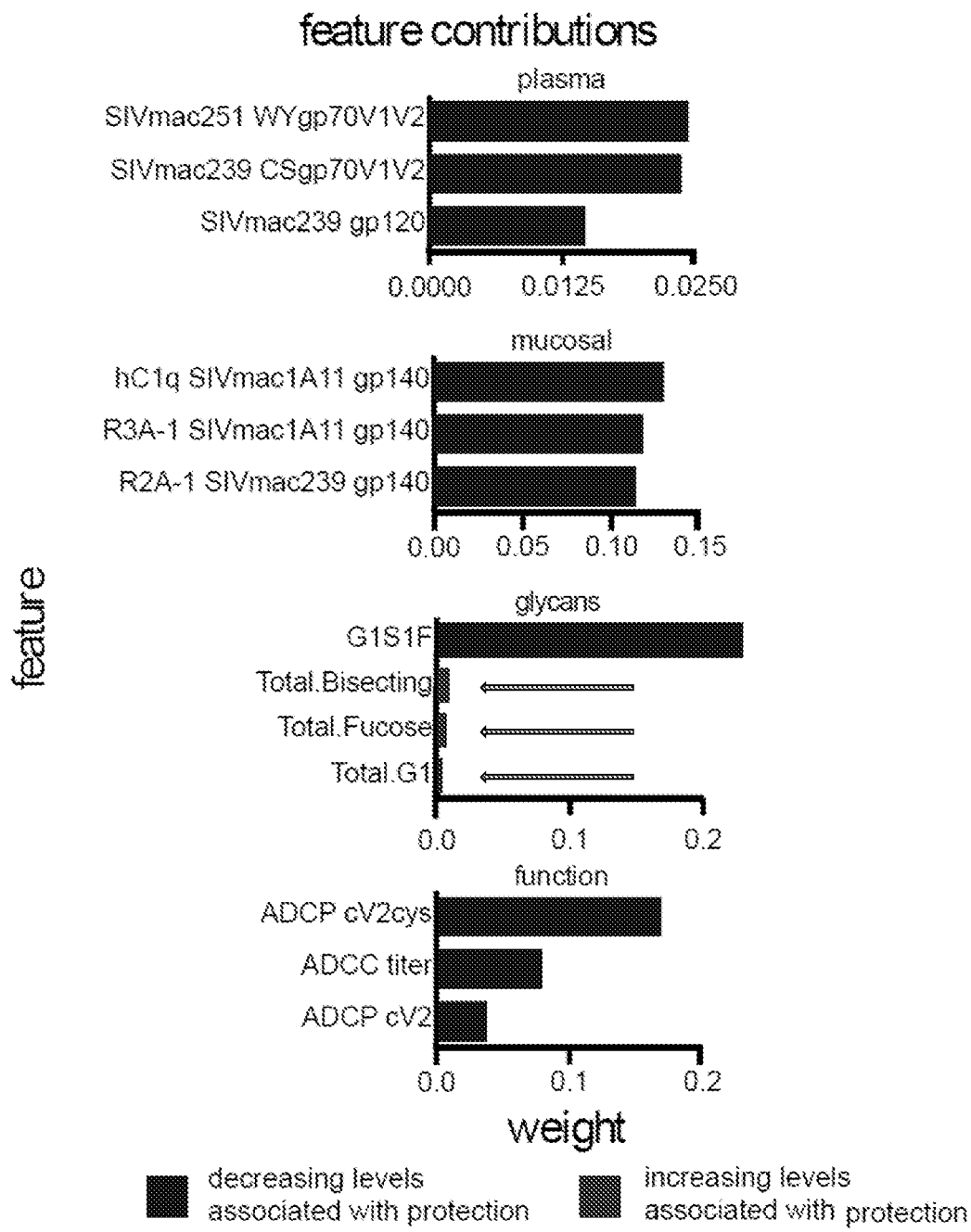

To provide further resolution of immune correlates, composite humoral profiles associated with protection were defined using logistic regression analyses of macaques that were infected following four or fewer challenges (≤4) or five or more challenges (≥5). Data was split according to plasma assessments, mucosal assessments, and assays of functional antibody activity. The ability of each data subset to train a classifier is presented, and the robustness of each model was assessed via cross-validation (FIG. 13A). Each data set exhibited the ability to resolve macaques according to the number of the challenges required to establish infection. The contributions of individual immune assessments supporting each prediction is presented in FIG. 13B—identifying V2-specific responses in plasma, Fc receptor ligation of SIV-specific antibodies in the mucosa, and ADCC and V2-specific phagocytosis as defining characteristics supporting discrimination between relatively more or less protected animals. Correlations between mucosal SIV-specific antibody assessments and challenge data is presented in FIG. 18C, and these continuous correlative relationships appear consistent with the classification models. Collectively, these data identify key specificities and functional activities associated with varying degrees of protection.

Figure 14A:
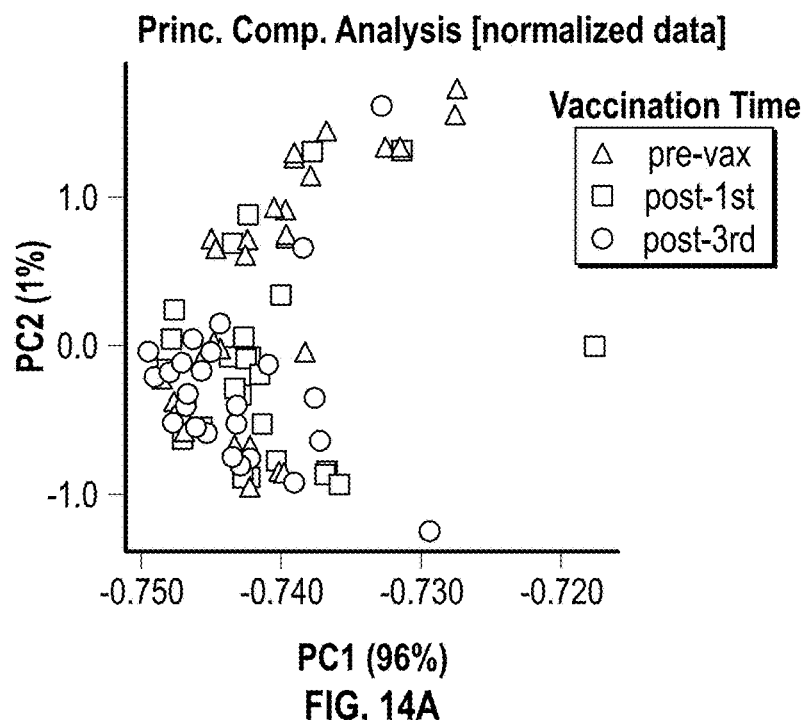
Figure 21:
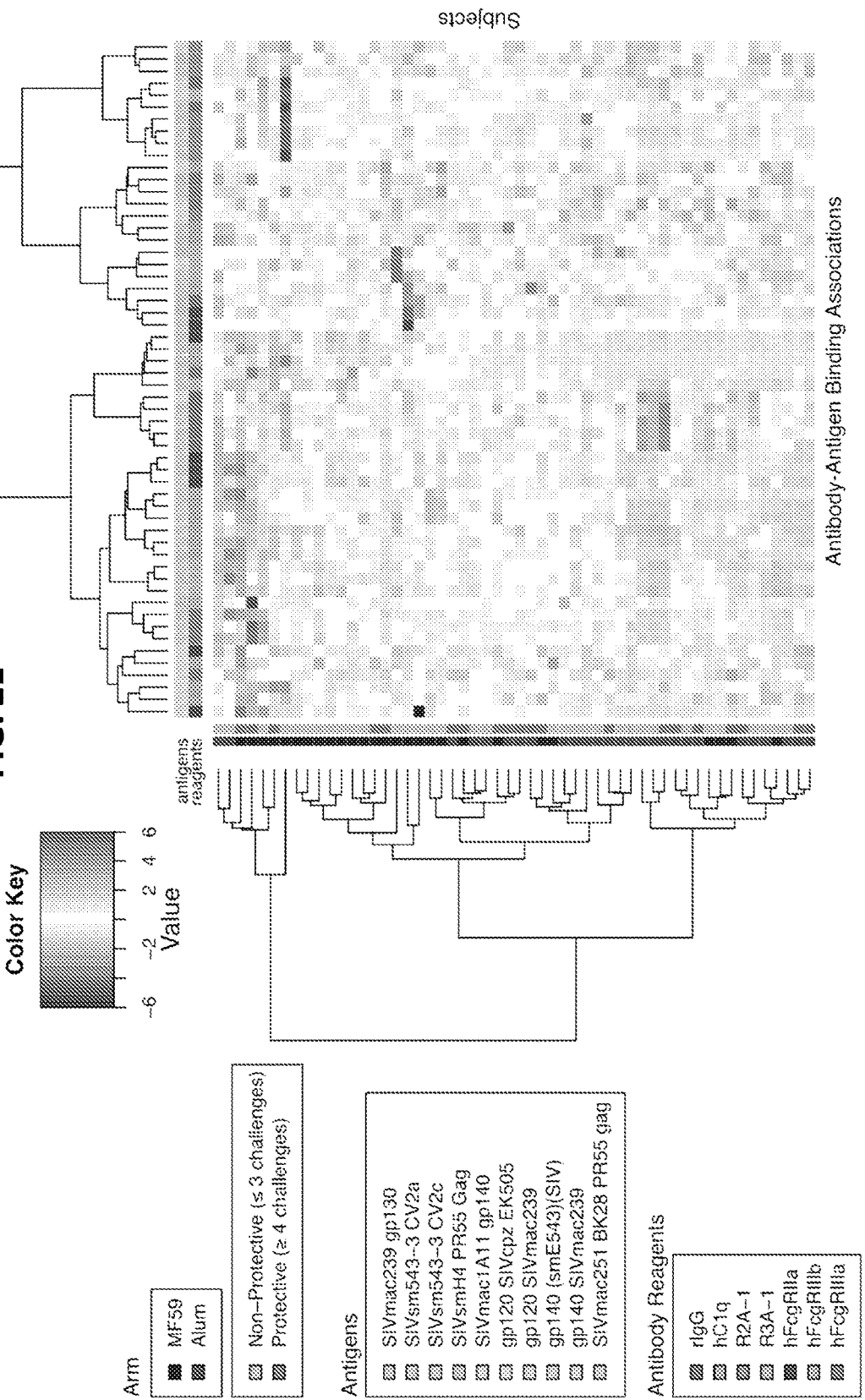

Microarray analysis of the transcriptome pre-vaccination, after the 1$^{st}$ immunization (post-1$^{st}$) and after the 3$^{rd}$ immunization (post-3$^{rd}$), was performed on blood of all twenty-seven immunized macaques. Vaccination status (pre-vax vs. post-vax) was the biggest driver of gene expression (96% of overall variance) (FIG. 14A and FIG. 21). Differential expression analysis was performed to identify genes differently expressed between the pre- and post-3$^{rd}$ vaccinations conditions. For a false-discovery rate of 5%, we identified 810 genes significantly differentially-expressed between the post-3$^{rd}$ vaccinations compare to the pre-vaccination conditions. Gene Set Enrichment Analysis (GSEA) was performed in order to identify pathways associated with response to vaccine. Briefly, transcripts were ordered by their probability of being differentially-expressed and enrichment of canonical pathways from the Ingenuity database was tested. Top enriched pathways were regrouped into modules based on the number of correlated transcripts shared by those pathways. The top enriched pathway contains genes associated with cell migration. Genes in this pathway were significantly associated with CXCR3+ ABC, as described in FIG. 34. This observation suggests that alum promotes cell migration to mucosal tissues (i.e infection sites such as rectal mucosa).

Figure 14B:
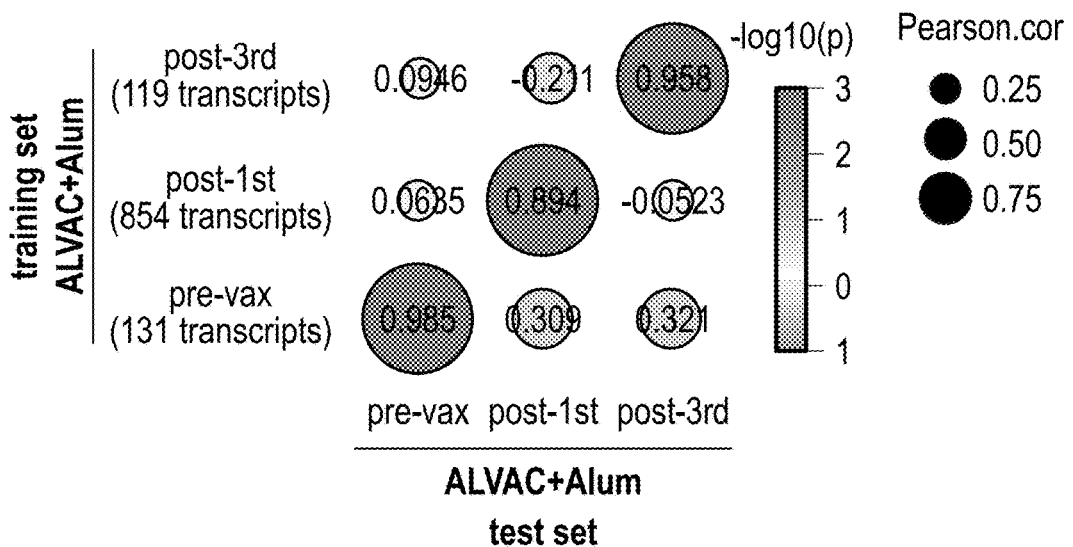
Figure 14C:
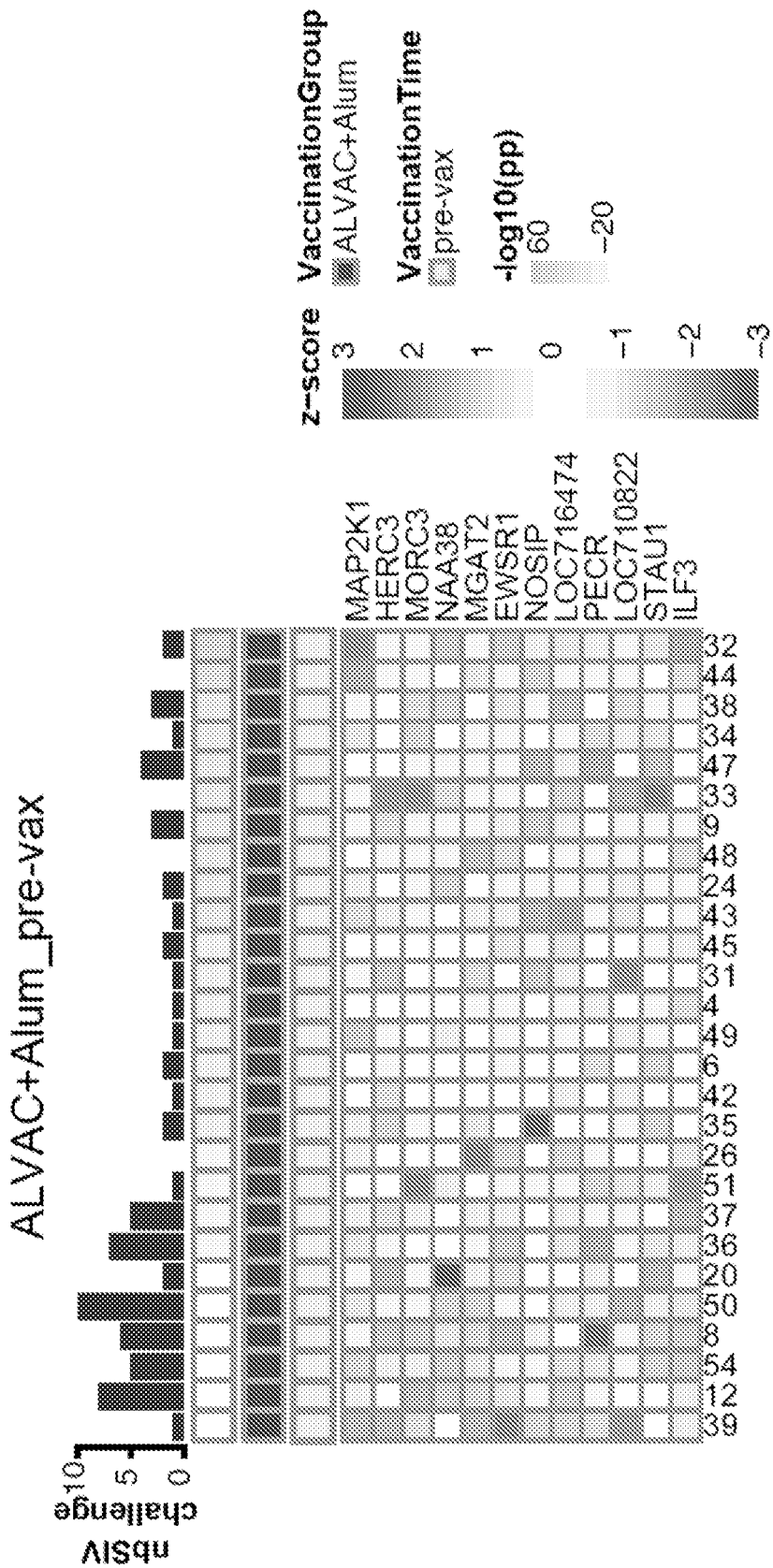
Figure 14D:
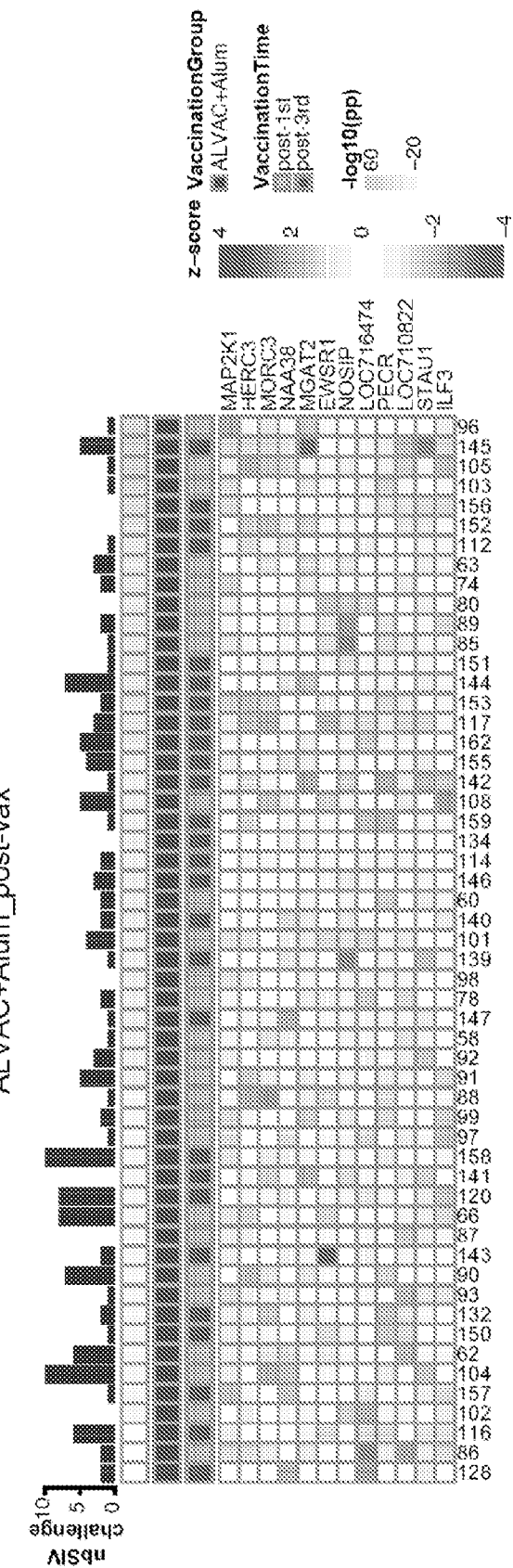

We assessed whether the changes in transcriptional profiles were associated with risk of SIV$_{mac251}$ acquisition. No transcripts were significantly associated with protection at the univariate level for the pre-vaccination and post-3$^{rd}$ immunization conditions (FIG. 22). Predictors of protection identified after immunization did not harbor any statistically significant prediction on the remaining samples, suggesting that transcripts associated with protection were not shared between immunization steps (FIG. 14B). The only exception was that pre-vaccination protective transcripts maintained significant predictive power when tested post-vaccination (1$^{st}$ and 3$^{rd}$ immunization), suggesting that the status of macaques prior to vaccination dictates (at least partially) which animals will be protected by this vaccine (FIG. 14B, FIGS. 26 and 27). A naïve Bayes classifier was built using the transcripts correlated to protection identified pre-vaccination, and this classifier was optimized by cross-validation (FIG. 28). Only 12 out of the initial 131 transcripts (FIG. 25) were required to predict the protection in vaccinated macaques (FIG. 14C). This 12-gene signature predicted time to acquisition in macaques treated by alum with 65% accuracy (FIG. 14D).

TABLE

Contributions of individual humoral assessments to logistic regression models trained to classify animals according to the number of challenges required to achieve infection within alum, MF59, or among both study arms.

| | Alum | | MF59 | | Both | |
|---|---|---|---|---|---|---|
| data | feature | coefficient | feature | coefficient | feature | coefficient |
| all | EC50.V1V2.1 | −0.19 | | | | |
| | p.R2A.1.SIVmac251.BK28.PR55.gag | −0.13 | p.hC1q.SIVmac251.BK28.PR55.gag | 0.25 | p.R2A.1.SIVmac251.BK28.PR55.gag | −0.41 |
| | (Intercept) | −0.08 | cV1V2cysIFNg. | −0.11 | cV1V2cysIFNg. | −0.35 |
| | | | (Intercept) | 0.00 | p.hC1q.SIVmac251.BK28.PR55.gag | 0.19 |
| | | | | | EC50.V1V2 | −0.18 |
| | | | | | (Intercept) | −0.15 |
| | | | | | p.rIgG.gp120.SIVmac239 | −0.13 |
| | | | | | Plasma.IgA.SIVmac251 | −0.11 |
| | | | | | p.hC1q.SIVmac1A11.gp140 | 0.11 |
| | | | | | Phagocytosis | −0.10 |
| | | | | | ADCCtiters | −0.06 |
| | | | | | p.R3A.1.SIVsmH4.PR55.Gag | −0.06 |
| | | | | | cV1V2fullIFNg. | −0.05 |
| fcfunc | gp120ADCD | 3.36 | | | m.R2A.1.SIVmac239.gp130 | 0.03 |
| | gp120CD107a. | −2.26 | cV1V2cysIFNg. | −2.82 | cV1V2cysIFNg. | −0.20 |
| | ADCCMaxkilling | −2.19 | gp120ADCD | −2.36 | (Intercept) | −0.02 |
| | cV22cysADCP | −2.05 | PBs.CXCR3.delta | −2.31 | | |
| | (Intercept) | 1.87 | gp120MIP1B. | 1.28 | | |
| | gp120IFNg. | 1.20 | Phagocytosis | −1.13 | | |
| | cV1V2cysCD107a. | −1.06 | (Intercept) | 1.05 | | |
| | cV1V2fullIFNg. | 1.02 | cV1V2cysCD107a. | −1.04 | | |
| | PBs.CXCR3.delta | 0.98 | cV1V2cysMIP1B. | 0.87 | | |
| | gp120ADCP | 0.94 | ADCCMaxkilling | 0.55 | | |
| | PBs.A4B7.delta | 0.59 | cV2fullADCP | 0.53 | | |
| | cV1V2fullMIP1B. | −0.40 | gp120ADCP | −0.36 | | |
| | Phagocytosis | −0.30 | cV22cysADCP | 0.28 | | |
| | cV1V2fullCD107a. | −0.25 | | | | |
| v2 | cV2fullADCP | −0.32 | | | | |
| | m.rIgG.SIVsm543.3.CV2a | 0.19 | cV1V2cysIFNg. | −0.25 | cV1V2cysIFNg. | −0.20 |
| | m.R2A.1.SIVsm543.3.CV2a | −0.12 | cV1V2fullIFNg. | −0.05 | (Intercept) | −0.02 |
| | (Intercept) | −0.11 | (Intercept) | −0.04 | | |
| | cV22cysADCP | −0.10 | | | | |
| | cV1V2cysIFNg. | −0.09 | | | | |
| | cV1V2cysCD107a. | −0.05 | | | | |
| plasma | p.R2A.1.SIVmac251.BK28.PR55.gag | −0.21 | | | | |
| | p.rIgG.gp120.SIVmac239 | −0.13 | p.hC1q.SIVmac251.BK28.PR55.gag | 0.28 | p.R2A.1.SIVmac251.BK28.PR55.gag | −0.29 |
| | (Intercept) | −0.08 | (Intercept) | 0.01 | p.rIgG.gp120.SIVmac239 | −0.16 |
| | | | | | p.hC1q.SIVmac251.BK28.PR55.gag | 0.15 |
| | | | | | (Intercept) | −0.06 |
| mucosal | m.R2A.1.gp140.SIVmac239 | −1.02 | | | p.hC1q.SIVmac1A11.gp140 | 0.00 |
| | m.R3A.1.gp120.SIVmac239 | 0.55 | m.R3A.1.SIVsm543.3.CV2c | −0.76 | m.R2A.1.gp140.SIVmac239 | −5.70 |
| | m.hC1q.SIVmac1A11.gp140 | −0.20 | m.rIgG.aRhesusIgG | −0.71 | m.hC1q.SIVsmH4.PR55.Gag | 3.56 |
| | (Intercept) | −0.16 | m.R2A.1.aRhesusIgG | 0.65 | m.R3A.1.gp120.SIVcpz.EK505 | −1.98 |
| | m.R2A.1.SIVmac239.gp130 | 0.08 | m.R2A.1.SIVsmH4.PR55.Gag | −0.55 | m.R3A.1.SIVsm543.3.CV2a | −1.78 |
| | | | m.hC1q.SIVsmH4.PR55.Gag | 0.39 | (Intercept) | −1.77 |
| | | | (Intercept) | −0.29 | m.hC1q.SIVmac1A11.gp140 | −1.66 |
| | | | m.rIgG.SIVsmH4.PR55.Gag | 0.26 | m.R2A.1.aRhesusIgG | 1.46 |
| | | | m.R3A.1.SIVmac239.gp130 | −0.18 | m.R2A.1.SIVmac239.gp130 | 1.39 |
| | | | m.rIgG.SIVmac1A11.gp140 | −0.07 | m.R2A.1.SIVsm543.3.CV2a | 1.18 |

TABLE-continued

Contributions of individual humoral assessments to logistic regression models trained to classify animals according to the number of challenges required to achieve infection within alum, MF59, or among both study arms.

| data | Alum | | MF59 | | Both | |
|---|---|---|---|---|---|---|
| | feature | coefficient | feature | coefficient | feature | coefficient |
| | | | m.R2A.1.SIVmac239.gp130 | 0.06 | m.rIgG.aRhesusIgG | −1.11 |
| | | | | | m.R3A.1.gp140.SIVmac239 | 0.93 |
| | | | | | m.hC1q.gp140..smE543..SIV. | −0.70 |
| | | | | | m.R3A.1.SIVsm543.3.CV2c | −0.60 |
| | | | | | m.hC1q.SIVsm543.3.CV2a | 0.59 |
| | | | | | m.R3A.1.SIVmac239.gp130 | 0.54 |
| | | | | | m.R2A.1.SIVmac1A11.gp140 | −0.48 |
| | | | | | m.rIgG.SIVsmH4.PR55.Gag | 0.46 |
| | | | | | m.rIgG.SIVsm543.3.CV2a | 0.43 |
| | | | | | m.rIgG.SIVsm543.3.CV2c | −0.41 |
| | | | | | m.hC1q.aRhesusIgG | −0.33 |
| | | | | | m.R2A.1.gp120.SIVmac239 | −0.30 |
| | | | | | m.R2A.1.SIVsmH4.PR55.Gag | −0.28 |
| | | | | | m.rIgG.SIVmac1A11.gp140 | −0.18 |
| | | | | | m.rIgG.gp120.SIVcpz.EK505 | −0.15 |
| | | | | | m.hC1q.gp120.SIVmac239 | 0.14 |
| | | | | | m.hC1q.SIVsm543.3.CV2c | 0.06 |
| | | | | | m.R3A.1.aRhesusIgG | 0.05 |

Figure 13C:
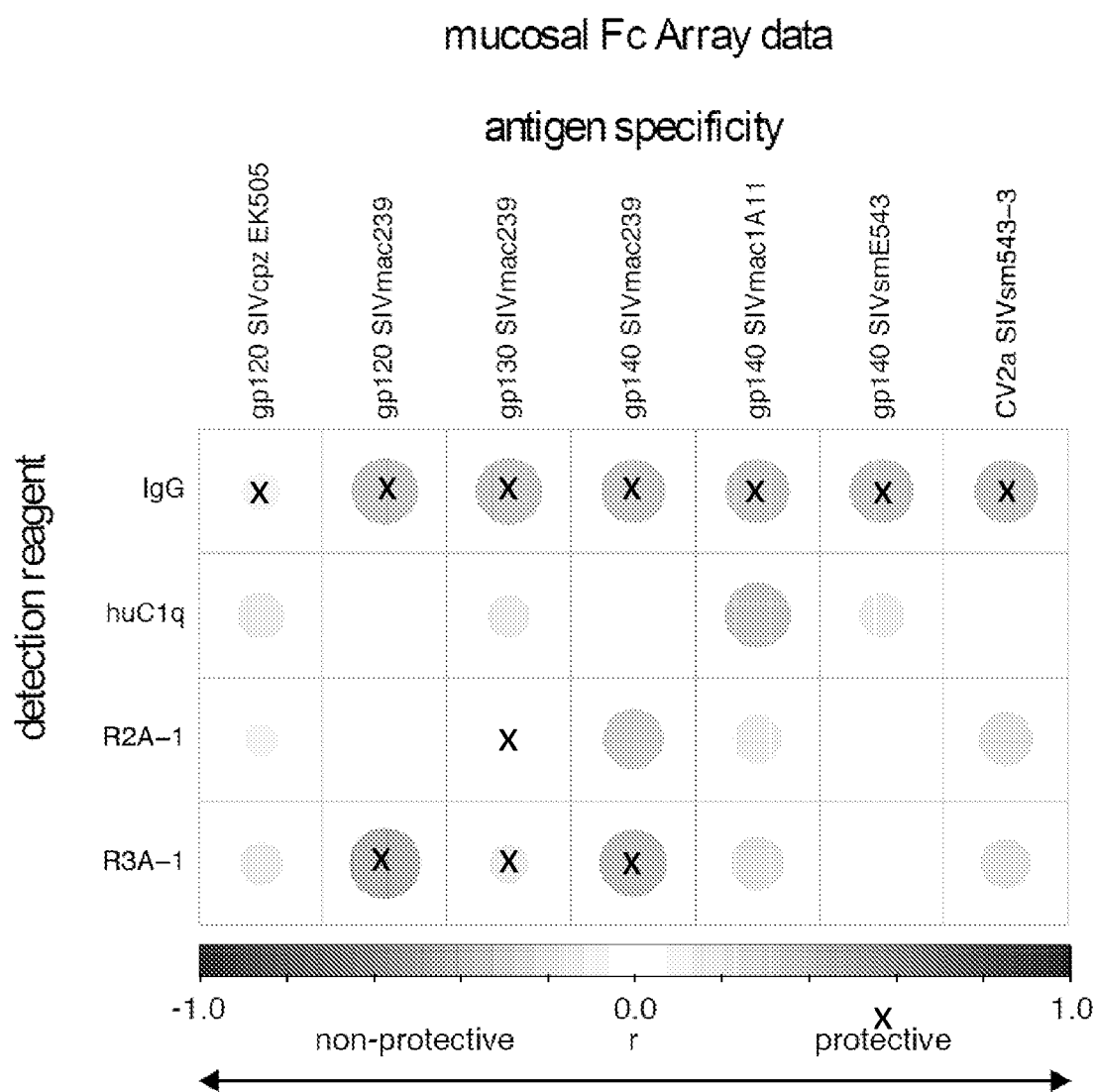
Figure 14E:
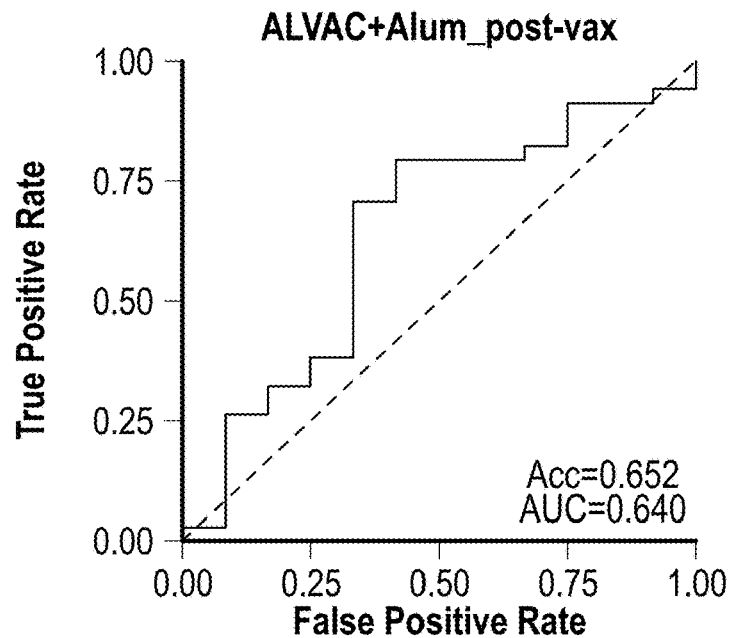
Figure 14F:
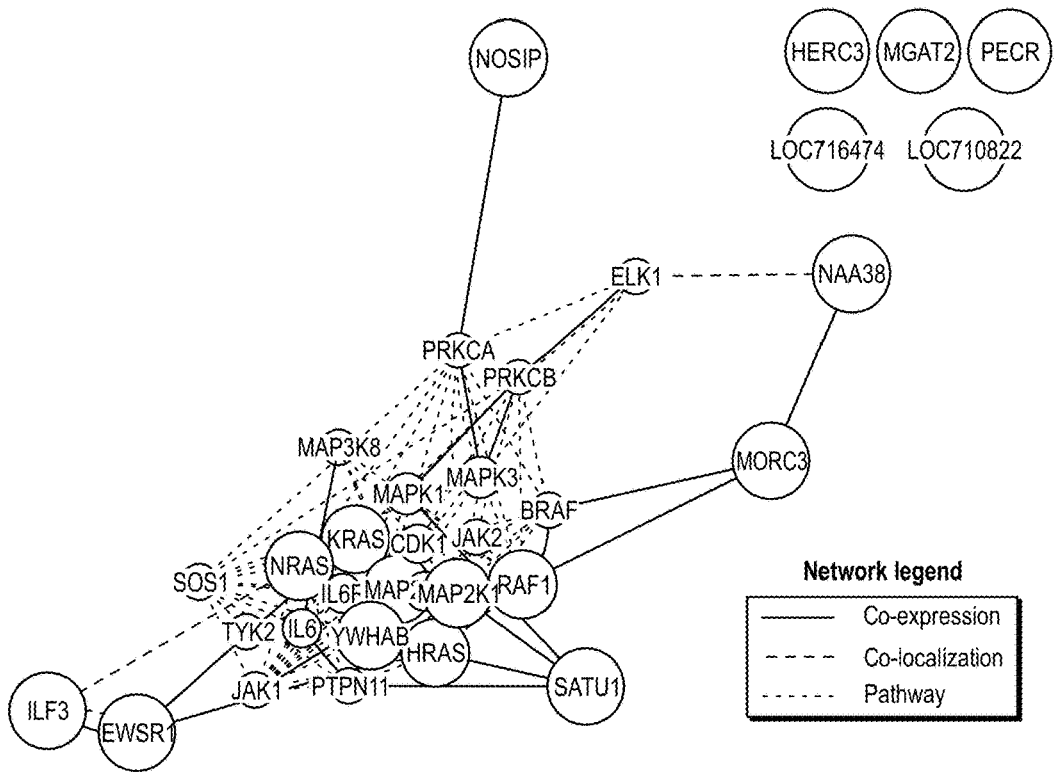
Figure 14G:
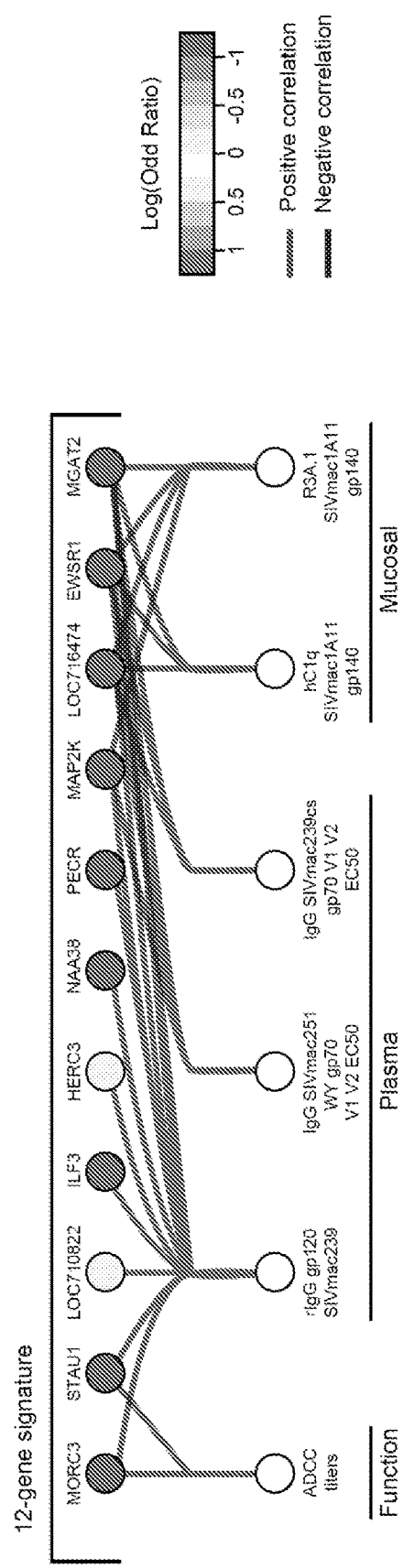

Gene Set Enrichment Analysis (GSEA) was performed in order to identify pathways associated with protection by alum, for both the pre- and post-3$^{rd}$ vaccination conditions. Top enriched pathways were regrouped into modules based on the number of correlated transcripts shared by those pathways. A RAS-related module was associated with protection by alum both pre-vaccination and post-vaccination (FIG. 29 and FIG. 30). In addition, network analysis revealed that RAS was directly or indirectly linked to the members of the 12-gene signature (FIG. 14E). In addition, the 12 genes predictive of protection by the vaccine were significantly correlated to humoral markers associated with protection identified in FIG. 13 (see also FIG. 14F).

In this study we recapitulated the results of the RV144 AIDS vaccine trial in humans in the SIV$_{mac251}$ model. These results provide not only a benchmark for the evaluation of novel vaccine candidates in NHP but also highlight the value of applying an integrated systems biology approach to both transcriptional and humoral immune profiling data that identified to parse out immune correlates of protection. This integrated systems analysis points to the importance of mucosal V2-specific humoral immune responses and the RAS signaling pathway in protection from virus acquisition, which is known to be essential for NK and T-cell function (Kortum et al., *Trends in Immunology* 34, 259 (June, 2013); Lee et al., Journal of Immunology 183, 7931 (Dec. 15, 2009)). Interestingly, RAS appears to be incorporated in exosomes and mediate immunological functions (Johnson and Chen., Current opinion in pharmacology 12, 458 (August, 2012); Rak and Guha, BioEssays: news and reviews in molecular, cellular and developmental biology 34, 489 (June, 2012)).

Collectively, our findings are consistent with a model, whereby ALVAC vaccination induces both type I-IFN and IL-1β (Barouch, *Journal of Virology*, (20101027 DCOM-20110124, 2014). Similarly, alum, via activation of the NALP3—inflammasome (Eisenbarth et al., *Nature*, (20080619 DCOM-20080730, 2008); Shaft et al., *Proc Natl Acad Sci USA*, (20090121 DCOM-20090205, 2009)) (although a dispensable step), (Flach et al., *Nat Med*, (20110408 DCOM-20110602, 2011) also induces IL-1β, as demonstrated by our microarray data. IL-1β induces prostaglandins that block production of IFN-γ (Keyel, LID—51043-4666(14)00075-1 [pii] LID—10.1016/j.cyto.2014.03.007 [doi]. *Cytokine and Growth Factor Reviews*, (20140421, 2014; van de Veerdonk et al., *Trends Immunol.*, (20110307 DCOM-20110425, 2011)). Maintaining low levels of IFN-γ favors Th17 differentiation (Aguado et al., (20020614 DCOM-20020715)), inhibits the IFN-γ-mediated upregulation of CXCR3 on plasmablasts (Kunkel et al., 20031002 DCOM-20031118, 2003)) and therefore can contribute to the generation of a greater number of α4β7$^+$ plasmablasts that home to mucosal sites (FIG. 4). Additionally, IL-1 induces ERK activation, a major downstream effector of RAS activation (Fischer et al., *Immunity*, (20051017 DCOM-20051122, 2005); Sharp et al., *Immunity*, (20051017 DCOM-20051122, 2005)). IL-1β also affects B cell activation (Falkoff et al., *J Immunol* 131, 801 (August, 1983)). As V2-cyclic peptide responses were associated with protection from infection in RV144, a linked transcriptomic analysis highlights the unique effects of alum in driving enhanced ASC trafficking to mucosal sites to produce these protective V2-cyclic peptide antibodies in a potentially RAS-dependent manner.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. An immunogenic composition comprising:

(i) an effective amount of human immunodeficiency virus (HIV) immunogen, or a nucleic acid encoding the immunogen; and (ii) an effective amount of an agent that stimulates the Ras pathway, wherein the agent comprises (a) epidermal growth factor or a functional fragment or variant thereof; (b) insulin like growth factor or a functional fragment or variant thereof; or (c) a combination of (a) and (b).

2. The immunogenic composition of claim 1, wherein the HIV immunogen is gp120, gp41 or gp160, or an immunogenic fragment thereof.

3. The immunogenic composition of claim 1, wherein the HIV immunogen comprises the V1V2 domain of gp120.

4. The immunogenic composition of claim 2, additionally comprising an aluminum salt.

5. The immunogenic composition of claim 1, comprising the nucleic acid encoding the immunogen.

6. The immunogenic composition of claim 5, comprising a vector, wherein the vector comprises the nucleic acid encoding the immunogen.

7. The immunogenic composition of claim 6, wherein the vector is a poxviral vector.

8. A method of inducing an immune response to a human immunodeficiency virus (HIV) in a subject, comprising administering an effective amount of the immunogenic composition of claim 1 to the subject, thereby inducing the immune response to the HIV.

9. The method of claim 8, wherein the agent comprises (a) epidermal growth factor or a functional fragment or variant hereof; (b) insulin like growth factor or a functional fragment or variant thereof; or (c) a combination thereof.

10. The method of claim 8, wherein the HIV immunogen, or the nucleic acid encoding the immunogen, and the agent that stimulates the Ras pathway are administered simultaneously.

11. The method of claim 8, wherein the HIV immunogen, or the nucleic acid encoding the immunogen, and the agent that stimulates the Ras pathway are administered sequentially.

12. The method of claim 8, wherein the HIV immunogen is gp120, gp41 or gp160, or an immunogenic fragment thereof.

13. The method of claim 12, wherein the immunogenic fragment comprises the V1V2 domain of gp120.

14. The method of claim 8, further comprising administering the HIV immunogen with an aluminum salt.

15. The method of claim 8, comprising administering the nucleic acid encoding the immunogen to the subject.

16. The method of claim 15, comprising administering a vector comprising the nucleic acid encoding the immunogen to the subject.

17. The method of claim 16, wherein the vector is a poxviral vector.

18. The method of claim 8, wherein the subject is a human subject.

19. The method of claim 18, wherein the human subject has a human immunodeficiency virus infection.

20. The method of claim 18, wherein the human subject has been exposed to HIV.

21. The method of claim 8, further comprising administering to the subject a therapeutically effective amount of an anti-retroviral agent to the subject.

22. The composition of claim 4, wherein the agent comprises a) the insulin like growth factor; or b) the epidermal growth factor.

23. The composition of claim 22, wherein the agent comprises a) the insulin like growth factor.

24. A method of inducing an immune response to a human immunodeficiency virus (HIV) in a subject, comprising administering an effective amount of the immunogenic composition of claim 22 to the subject, thereby inducing the immune response to the HIV.

25. A method of inducing an immune response to a human immunodeficiency virus (HIV) in a subject, comprising administering an effective amount of the immunogenic composition of claim 23 to the subject, thereby inducing the immune response to the HIV.

* * * * *

SEQUENCE LISTING

```
<160> NUMBER OF SEQ ID NOS: 34

<210> SEQ ID NO 1
<211> LENGTH: 53
<212> TYPE: PRT
<213> ORGANISM: Macaca mulatta

<400> SEQUENCE: 1

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 2
<211> LENGTH: 53
<212> TYPE: PRT
<213> ORGANISM: Homo sapiens

<400> SEQUENCE: 2

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 3
<211> LENGTH: 158
<212> TYPE: PRT
<213> ORGANISM: Homo sapiens

<400> SEQUENCE: 3

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125
```

Met Pro Lys Thr Gln Lys Tyr Gln Pro Pro Ser Thr Asn Lys Asn Thr
            130                 135                 140

Lys Ser Gln Arg Arg Lys Gly Ser Thr Phe Glu Glu Arg Lys
145                 150                 155

<210> SEQ ID NO 4
<211> LENGTH: 138
<212> TYPE: PRT
<213> ORGANISM: Homo sapiens

<400> SEQUENCE: 4

Met Ile Thr Pro Thr Val Lys Met His Thr Met Ser Ser His Leu
1               5                   10                  15

Phe Tyr Leu Ala Leu Cys Leu Leu Thr Phe Thr Ser Ser Ala Thr Ala
                20                  25                  30

Gly Pro Glu Thr Leu Cys Gly Ala Glu Leu Val Asp Ala Leu Gln Phe
                35                  40                  45

Val Cys Gly Asp Arg Gly Phe Tyr Phe Asn Lys Pro Thr Gly Tyr Gly
            50                  55                  60

Ser Ser Ser Arg Arg Ala Pro Gln Thr Gly Ile Val Asp Glu Cys Cys
65                  70                  75                  80

Phe Leu Ser Cys Asp Leu Arg Arg Leu Glu Met Tyr Cys Ala Pro Leu
                85                  90                  95

Lys Pro Ala Lys Ser Ala Arg Ser Val Arg Ala Gln Arg His Thr Asp
                100                 105                 110

Met Pro Lys Thr Gln Lys Glu Val His Leu Lys Asn Ala Ser Arg Gly
            115                 120                 125

Ser Ala Gly Asn Lys Asn Tyr Arg Met Leu
        130                 135

<210> SEQ ID NO 5
<211> LENGTH: 137
<212> TYPE: PRT
<213> ORGANISM: Homo sapiens

<400> SEQUENCE: 5

Met Ile Thr Pro Thr Val Lys Met His Thr Met Ser Ser His Leu
1               5                   10                  15

Phe Tyr Leu Ala Leu Cys Leu Leu Thr Phe Thr Ser Ser Ala Thr Ala
                20                  25                  30

Gly Pro Glu Thr Leu Cys Gly Ala Glu Leu Val Asp Ala Leu Gln Phe
                35                  40                  45

Val Cys Gly Asp Arg Gly Phe Tyr Phe Asn Lys Pro Thr Gly Tyr Gly
            50                  55                  60

Ser Ser Ser Arg Arg Ala Pro Gln Thr Gly Ile Val Asp Glu Cys Cys
65                  70                  75                  80

Phe Arg Ser Cys Asp Leu Arg Arg Leu Glu Met Tyr Cys Ala Pro Leu
                85                  90                  95

Lys Pro Ala Lys Ser Ala Arg Ser Val Arg Ala Gln Arg His Thr Asp
                100                 105                 110

Met Pro Lys Thr Gln Lys Glu Val His Leu Lys Asn Ala Ser Arg Gly
            115                 120                 125

Ser Ala Gly Asn Lys Asn Tyr Arg Met
        130                 135

<210> SEQ ID NO 6

```
<211> LENGTH: 195
<212> TYPE: PRT
<213> ORGANISM: Homo sapiens

<400> SEQUENCE: 6

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Tyr Gln Pro Pro Ser Thr Asn Lys Asn Thr
130                 135                 140

Lys Ser Gln Arg Arg Lys Gly Trp Pro Lys Thr His Pro Gly Gly Glu
145                 150                 155                 160

Gln Lys Glu Gly Thr Glu Ala Ser Leu Gln Ile Arg Gly Lys Lys
                165                 170                 175

Glu Gln Arg Arg Glu Ile Gly Ser Arg Asn Ala Glu Cys Arg Gly Lys
            180                 185                 190

Lys Gly Lys
        195

<210> SEQ ID NO 7
<211> LENGTH: 153
<212> TYPE: PRT
<213> ORGANISM: Homo sapiens

<400> SEQUENCE: 7

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
130                 135                 140
```

-continued

Ser Ala Gly Asn Lys Asn Tyr Arg Met
145                 150

<210> SEQ ID NO 8
<211> LENGTH: 138
<212> TYPE: PRT
<213> ORGANISM: Homo sapiens

<400> SEQUENCE: 8

Met Ile Thr Pro Thr Val Lys Met His Thr Met Ser Ser His Leu
1               5                   10                  15

Phe Tyr Leu Ala Leu Cys Leu Leu Thr Phe Thr Ser Ser Ala Thr Ala
                20                  25                  30

Gly Pro Glu Thr Leu Cys Gly Ala Glu Leu Val Asp Ala Leu Gln Phe
            35                  40                  45

Val Cys Gly Asp Arg Gly Phe Tyr Phe Asn Lys Pro Thr Gly Tyr Gly
50                  55                  60

Ser Ser Ser Arg Arg Ala Pro Gln Thr Gly Ile Val Asp Glu Cys Cys
65                  70                  75                  80

Phe Leu Ser Cys Asp Leu Arg Arg Leu Glu Met Tyr Cys Ala Pro Leu
                85                  90                  95

Lys Pro Ala Lys Ser Ala Arg Ser Val Arg Ala Gln Arg His Thr Asp
            100                 105                 110

Met Pro Lys Thr Gln Lys Glu Val His Leu Lys Asn Ala Ser Arg Gly
        115                 120                 125

Ser Ala Gly Asn Lys Asn Tyr Arg Met Asp
    130                 135

<210> SEQ ID NO 9
<211> LENGTH: 196
<212> TYPE: PRT
<213> ORGANISM: Homo sapiens

<400> SEQUENCE: 9

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
                20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Tyr Gln Pro Pro Ser Thr Asn Lys Asn Thr
    130                 135                 140

Lys Ser Gln Arg Arg Lys Gly Trp Pro Lys Thr His Pro Gly Gly Glu
145                 150                 155                 160

Gln Lys Glu Gly Thr Glu Ala Ser Leu Gln Ile Arg Gly Lys Lys Lys
                165                 170                 175

Glu Gln Arg Arg Glu Ile Gly Ser Arg Asn Ala Glu Cys Arg Gly Lys
            180                 185                 190

Lys Gly Lys Leu
        195

<210> SEQ ID NO 10
<211> LENGTH: 137
<212> TYPE: PRT
<213> ORGANISM: Homo sapiens

<400> SEQUENCE: 10

Met Ile Thr Pro Thr Val Lys Met His Thr Met Ser Ser His Leu
1               5                   10                  15

Phe Tyr Leu Ala Leu Cys Leu Leu Thr Phe Thr Ser Ser Ala Thr Ala
                20                  25                  30

Gly Pro Glu Thr Leu Cys Gly Ala Glu Leu Val Asp Ala Leu Gln Phe
            35                  40                  45

Val Cys Gly Asp Arg Gly Phe Tyr Phe Asn Lys Pro Thr Gly Tyr Gly
50                  55                  60

Ser Ser Ser Arg Arg Ala Pro Gln Thr Gly Ile Val Asp Glu Cys Cys
65                  70                  75                  80

Phe Leu Ser Cys Asp Leu Arg Arg Leu Glu Met Tyr Cys Ala Pro Leu
                85                  90                  95

Lys Pro Ala Lys Ser Ala Arg Ser Val Arg Ala Gln Arg His Thr Asp
            100                 105                 110

Met Pro Lys Thr Gln Lys Glu Val His Leu Lys Asn Ala Ser Arg Gly
        115                 120                 125

Ser Ala Gly Asn Lys Asn Tyr Arg Met
    130                 135

<210> SEQ ID NO 11
<211> LENGTH: 153
<212> TYPE: PRT
<213> ORGANISM: Macaca mulatta

<400> SEQUENCE: 11

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser His Leu
                20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150

<210> SEQ ID NO 12
<211> LENGTH: 151
<212> TYPE: PRT
<213> ORGANISM: Homo sapiens

<400> SEQUENCE: 12

Met Gly Lys Ile Ser Ser Leu Pro Thr Gly Leu Phe Lys Cys Cys Phe
1               5                   10                  15

Cys Asp Phe Leu Lys Val Lys Met His Thr Met Ser Ser His Phe
            20                  25                  30

Tyr Leu Ala Leu Cys Leu Leu Thr Phe Thr Ser Ser Ala Thr Ala Gly
        35                  40                  45

Pro Glu Thr Leu Cys Gly Ala Glu Leu Val Asp Ala Leu Gln Phe Val
    50                  55                  60

Cys Gly Asp Arg Gly Phe Tyr Phe Asn Lys Pro Thr Gly Tyr Gly Ser
65                  70                  75                  80

Ser Arg Arg Ala Pro Gln Thr Gly Ile Val Asp Glu Cys Cys Phe Arg
                85                  90                  95

Ser Cys Asp Leu Arg Arg Leu Glu Met Tyr Cys Ala Pro Leu Lys Pro
            100                 105                 110

Ala Lys Ser Ala Arg Ser Val Arg Ala Gln Arg His Thr Asp Met Pro
        115                 120                 125

Lys Thr Gln Lys Glu Val His Leu Lys Asn Ala Ser Arg Gly Ser Ala
    130                 135                 140

Gly Asn Lys Asn Tyr Arg Met
145                 150

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gtctggaaaa acctgccaag                                          20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
acctggtgct cagtgtagcc                                          20

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
gcagaggagg aaattaccca gtac                                     24

<210> SEQ ID NO 16
<211> LENGTH: 25
<212> TYPE: DNA

<210> SEQ ID NO 17
<211> LENGTH: 56
<212> TYPE: PRT
<213> ORGANISM: Simian immunodeficiency virus

<400> SEQUENCE: 17

Cys Ile Lys Asn Asn Ser Cys Ala Gly Leu Glu Gln Glu Pro Met Ile
1               5                   10                  15

Gly Cys Lys Phe Asn Met Thr Gly Leu Lys Arg Asp Lys Lys Ile Glu
            20                  25                  30

Tyr Asn Glu Thr Trp Tyr Ser Arg Asp Leu Ile Cys Glu Gln Pro Ala
        35                  40                  45

Asn Gly Ser Glu Ser Lys Cys Tyr
    50                  55

<210> SEQ ID NO 18
<211> LENGTH: 57
<212> TYPE: PRT
<213> ORGANISM: Simian immunodeficiency virus

<400> SEQUENCE: 18

Cys Ile Ala Gln Asn Asn Cys Thr Gly Leu Glu Gln Glu Gln Met Ile
1               5                   10                  15

Ser Cys Lys Phe Asn Met Thr Gly Leu Lys Arg Asp Lys Thr Lys Glu
            20                  25                  30

Tyr Asn Glu Thr Trp Tyr Ser Thr Asp Leu Val Cys Glu Gln Gly Asn
        35                  40                  45

Ser Thr Asp Asn Glu Ser Arg Cys Tyr
    50                  55

<210> SEQ ID NO 19
<211> LENGTH: 68
<212> TYPE: PRT
<213> ORGANISM: Simian immunodeficiency virus

<400> SEQUENCE: 19

Asn Glu Thr Ser Ser Cys Ile Ala Gln Asn Asn Cys Thr Gly Leu Glu
1               5                   10                  15

Gln Glu Gln Met Ile Ser Cys Lys Phe Thr Met Thr Gly Leu Lys Arg
            20                  25                  30

Asp Lys Thr Lys Glu Tyr Asn Glu Thr Trp Tyr Ser Thr Asp Leu Val
        35                  40                  45

Cys Glu Gln Gly Asn Ser Thr Asp Asn Glu Ser Arg Cys Tyr Met Asn
    50                  55                  60

His Cys Asn Thr
65

<210> SEQ ID NO 20
<211> LENGTH: 20
<212> TYPE: PRT
<213> ORGANISM: Simian immunodeficiency virus

<400> SEQUENCE: 20

Asn Glu Thr Ser Ser Cys Ile Ala Gln Asn Asn Cys Thr Gly Leu Glu
1               5                   10                  15

Gln Glu Gln Met
            20

<210> SEQ ID NO 21
<211> LENGTH: 20
<212> TYPE: PRT
<213> ORGANISM: Simian immunodeficiency virus

<400> SEQUENCE: 21

Ile Ala Gln Asn Asn Cys Thr Gly Leu Glu Gln Glu Gln Met Ile Ser
1               5                   10                  15

Cys Lys Phe Thr
            20

<210> SEQ ID NO 22
<211> LENGTH: 20
<212> TYPE: PRT
<213> ORGANISM: Simian immunodeficiency virus

<400> SEQUENCE: 22

Thr Gly Leu Glu Gln Glu Gln Met Ile Ser Cys Lys Phe Thr Met Thr
1               5                   10                  15

Gly Leu Lys Arg
            20

<210> SEQ ID NO 23
<211> LENGTH: 20
<212> TYPE: PRT
<213> ORGANISM: Simian immunodeficiency virus

<400> SEQUENCE: 23

Gln Met Ile Ser Cys Lys Phe Thr Met Thr Gly Leu Lys Arg Asp Lys
1               5                   10                  15

Thr Lys Glu Tyr
            20

<210> SEQ ID NO 24
<211> LENGTH: 20
<212> TYPE: PRT
<213> ORGANISM: Simian immunodeficiency virus

<400> SEQUENCE: 24

Phe Thr Met Thr Gly Leu Lys Arg Asp Lys Thr Lys Glu Tyr Asn Glu
1               5                   10                  15

Thr Trp Tyr Ser
            20

<210> SEQ ID NO 25
<211> LENGTH: 20
<212> TYPE: PRT
<213> ORGANISM: Simian immunodeficiency virus

<400> SEQUENCE: 25

Lys Arg Asp Lys Thr Lys Glu Tyr Asn Glu Thr Trp Tyr Ser Thr Asp
1               5                   10                  15

Leu Val Cys Glu
            20

<210> SEQ ID NO 26
<211> LENGTH: 67

```
<212> TYPE: PRT
<213> ORGANISM: Simian immunodeficiency virus

<400> SEQUENCE: 26

Asn Glu Thr Ser Ser Cys Ile Ala Gln Asp Asn Thr Gly Leu Glu Gln
1               5                   10                  15

Glu Gln Met Ile Ser Cys Lys Phe Asn Met Thr Gly Leu Lys Arg Asp
            20                  25                  30

Lys Lys Lys Glu Tyr Asn Glu Thr Trp Tyr Ser Ala Asp Leu Val Cys
        35                  40                  45

Glu Gln Gly Asn Asn Thr Gly Asn Glu Ser Arg Cys Tyr Met Asn His
    50                  55                  60

Cys Asn Thr
65

<210> SEQ ID NO 27
<211> LENGTH: 14
<212> TYPE: PRT
<213> ORGANISM: Simian immunodeficiency virus

<400> SEQUENCE: 27

Ser Ser Cys Ile Ala Gln Asp Asn Cys Thr Gly Leu Glu Gln
1               5                   10

<210> SEQ ID NO 28
<211> LENGTH: 15
<212> TYPE: PRT
<213> ORGANISM: Simian immunodeficiency virus

<400> SEQUENCE: 28

Cys Ile Ala Gln Asp Asn Cys Thr Gly Leu Glu Gln Glu Gln Met
1               5                   10                  15

<210> SEQ ID NO 29
<211> LENGTH: 15
<212> TYPE: PRT
<213> ORGANISM: Simian immunodeficiency virus

<400> SEQUENCE: 29

Gln Asp Asn Cys Thr Gly Leu Glu Gln Glu Gln Met Ile Ser Cys
1               5                   10                  15

<210> SEQ ID NO 30
<211> LENGTH: 15
<212> TYPE: PRT
<213> ORGANISM: Simian immunodeficiency virus

<400> SEQUENCE: 30

Ile Ser Cys Lys Phe Asn Met Thr Gly Leu Lys Arg Asp Lys Lys
1               5                   10                  15

<210> SEQ ID NO 31
<211> LENGTH: 15
<212> TYPE: PRT
<213> ORGANISM: Simian immunodeficiency virus

<400> SEQUENCE: 31

Ile Ser Cys Lys Phe Asn Met Thr Gly Leu Lys Arg Asp Lys Lys
1               5                   10                  15

<210> SEQ ID NO 32
<211> LENGTH: 15
<212> TYPE: PRT
```

-continued

```
<213> ORGANISM: Simian immunodeficiency virus

<400> SEQUENCE: 32

Met Thr Gly Leu Lys Arg Asp Lys Lys Lys Glu Tyr Asn Glu Thr
1               5                   10                  15

<210> SEQ ID NO 33
<211> LENGTH: 15
<212> TYPE: PRT
<213> ORGANISM: Simian immunodeficiency virus

<400> SEQUENCE: 33

Leu Lys Arg Asp Lys Lys Lys Glu Tyr Asn Glu Thr Trp Tyr Ser
1               5                   10                  15

<210> SEQ ID NO 34
<211> LENGTH: 15
<212> TYPE: PRT
<213> ORGANISM: Simian immunodeficiency virus

<400> SEQUENCE: 34

Asp Lys Lys Lys Glu Tyr Asn Glu Thr Trp Tyr Ser Ala Asp Leu
1               5                   10                  15
```